(12) United States Patent
Austin et al.

(10) Patent No.: US 6,806,273 B1
(45) Date of Patent: Oct. 19, 2004

(54) COMPOUNDS

(75) Inventors: Rupert Austin, Leics (GB); Andrew Baxter, Leics (GB); Roger Bonnert, Hoton (GB); Fraser Hunt, Nottingham (GB); Elizabeth Kinchin, Leics (GB); Paul Willis, Nottingham (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/403,392
(22) PCT Filed: Aug. 3, 1999
(86) PCT No.: PCT/SE99/01333
§ 371 (c)(1), (2), (4) Date: Oct. 21, 2001
(87) PCT Pub. No.: WO00/09511
PCT Pub. Date: Feb. 24, 2000

(30) Foreign Application Priority Data

Aug. 13, 1998 (SE) ............................................. 9802729

(51) Int. Cl.$^7$ ...................... A61K 31/519; A01N 43/90; C07D 487/00
(52) U.S. Cl. .................................... 514/260.1; 544/280
(58) Field of Search ........................ 514/260.1; 544/280

(56) References Cited

U.S. PATENT DOCUMENTS 2,772,164 A  11/1956  Allen et al. .................... 96/109
5,202,328 A  * 4/1993  de Laszlo et al. ........ 514/263.3
6,107,294 A  * 8/2000  Beck ........................... 514/241

OTHER PUBLICATIONS

Maggiolo et al, "Studies on Condensed Pyrimidine Systems . . . ," J. Amer. Chem. Soc., vol. 73, pp. 4226–4228 (1951).
Baker et al, "Synthesis of Derivatives of Thiazolo . . . ," J. Chem. Soc. , pp. 2478–2484 (1970).
STN Int'l, File CAPLUS, CAPLUS accession No. 1996–243961, Gewald et al, New Synthesis of substituted . . . , (1996).
STN Int'l, File CAPLUS, CAPLUS accession No. 1990–235252, Ahluwalia et al, "One–step Synthesis of thiazolo . . . ," (1989).
STN Int'l, File CAPLUS, CAPLUS accession No. 1990:158124, Pawar et al, "Studies on the Vilsmeier–Haak reaction . . . ," (1989).
Takahashi et al, "Studies on Pyrimidine Derivatives . . . ," Chem. Pharm. Bull., vol. 6, pp. 334–338 (1958).

* cited by examiner

Primary Examiner—Richard L. Raymond
Assistant Examiner—Tamthom N. Truong
(74) Attorney, Agent, or Firm—Nixon & Vanderhye

(57) ABSTRACT

The invention provides certain thiazolopyrimidine compounds, processes and intermediates used in their preparation, pharmaceutical compositions containing them and their use in therapy.

37 Claims, No Drawings

COMPOUNDS

The present invention relates to certain thiazolopyrimidine compounds, processes and intermediates used in their preparation, pharmaceutical compositions containing them and their use in therapy.

The compound 2,7-diamino-5-methylmercapto-thiazolo[4,5-d]pyrimidine is known from J. Amer. Chem. Soc., 73, 4226–4227 (1951).

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

In accordance with the present invention, there is therefore provided a compound of general formula

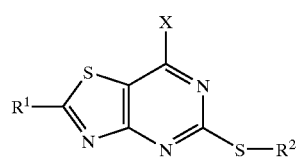

(I)

wherein $R^1$ represents a hydrogen atom, or a group $-NR^3R^4$;

$R^3$ and $R^4$ each independently represent a hydrogen atom, or a 4-piperidinyl, $C_3-C_6$ to cycloalkyl or $C_1-C_8$ alkyl group, which latter two groups may be optionally substituted by one or more substituent groups independently selected from halogen atoms and $-NR^5R^6$, $-CONR^5R^6$, $-OR^7$, $-COOR^7$, $-NR^8COR^9$, $-SR^{10}$, $-SO_2R^{10}$, $-SO_2NR^5R^6$, $-NR^8SO_2R^9$, morpholinyl, $C_1-C_4$ alkyl, $C_3-C_6$ cycloalkyl, tetrahydrofuranyl and aryl groups, wherein an aryl substituent group may be a phenyl, naphthyl, thienyl, pyridinyl, imidazolyl or indolyl group, each of which may be optionally substituted by one or more substituents independently selected from halogen atoms and cyano, nitro, $-NR^5R^6$, $-CONR^5R^6$, $-OR^7$, $-NR^8COR^9$, $-SO_2NR^5R^6$, $-NR^8SO_2R^9$, $C_1-C_6$ alkyl and trifluoromethyl groups, or $R^3$ and $R^4$ together with the nitrogen atom to which they are attached form a 4- to 7-membered saturated heterocyclic ring system, which ring system may be optionally substituted by one or more substituent groups independently selected from

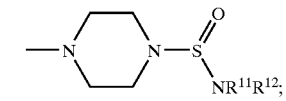

$-NR^5R^6$, $-CONR^5R^6$, $-OR^7$, $-COOR^{10}$, $-NR^8COR^9$, and $C_1-C_6$ alkyl optionally substituted by one or more substituents independently selected from halogen atoms and $-NR^{11}R^{12}$ and $-OR^7$ groups;

X represents a group $-OH$ or $-NR^{13}R^{14}$;

$R^{13}$ and $R^{14}$ each independently represent a hydrogen atom, a 4-piperidinyl group optionally substituted by a $C_1-C_4$ alkylphenyl substituent group, or a $C_3-C_7$ carbocyclic, $C_1-C_8$ alkyl, $C_2-C_6$ alkenyl or $C_2-C_6$ alkynyl group, which latter four groups may be optionally substituted by one or more substituent groups independently selected from halogen atoms and $-NR^5R^6$, $-CONR^5R^6$, $-OR^7$, $-COOR^7$, $-NR^8COR^9$, $-SR^{10}$, $-SO_2R^{10}$, $-SO_2NR^5R^6$, $-NR^8SO_2R^9$, morpholinyl, $C_1-C_4$ alkyl, $C_3-C_6$ cycloalkyl and aryl groups, wherein an aryl substituent group may be a phenyl, naphthyl, thienyl, pyridinyl, imidazolyl or indolyl group, each of which may be optionally substituted by one or more substituents independently selected from halogen atoms and cyano, nitro, $-NR^5R^6$, $-CONR^5R^6$, $-OR^7$, $-NR^8COR^9$, $-SO_2NR^5R^6$, $NR^8S_2R^9$, $C_1-C_6$ alkyl and trifluoromethyl groups, or $R^{13}$ and $R^{14}$ together with the nitrogen atom to which they are attached form a 4- to 7-membered saturated heterocyclic ring system, which ring system may be optionally substituted by one or more substituent groups independently selected from $-NR^5R^6$, $-CONR^5R^6$, $-OR^7$, $-COOR^7$, $-NR^8COR^9$, and $C_1-C_6$ alkyl optionally substituted by one or more substituents independently selected from halogen atoms and phenyl, $-NR^{11}R^{12}$ and $-OR^7$ groups;

$R^2$ represents a $C_1-C_6$ alkyl or $C_2-C_6$ alkenyl group optionally substituted by a phenyl or phenoxy group, wherein the phenyl or phenoxy group may itself be optionally substituted by one or more substituents independently selected from halogen atoms and nitro, $C_1-C_6$ alkyl, trifluoromethyl, $-OR^7$, $-C(O)R^7$, $-SR^{10}$, $-NR^{15}R^{16}$ and phenyl groups;

$R^5$ and $R^6$ each independently represent a hydrogen atom or a $C_1-C_6$ alkyl or phenyl group, each of which may be optionally substituted by one or more substituent groups independently selected from halogen atoms, phenyl, $-OR^{17}$ and $-NR^{15}R^{16}$, or $R^5$ and $R^6$ together with the nitrogen atom to which they are attached form a 4- to 7-membered saturated heterocyclic ring system optionally comprising a further heteroatom selected from oxygen and nitrogen atoms, which ring system may be optionally substituted by one or more substituent groups independently selected from phenyl, $-OR^{17}$, $-COOR^{17}$, $-NR^{15}R^{16}$, $-CONR^{15}R^{16}$, $-NR^{15}COR^{16}$, $-SONR^{15}R^{16}$, and $C_1-C_6$ alkyl optionally substituted by one or more substituents independently selected from halogen atoms and $-NR^{15}R^{16}$ and $-OR^{17}$ groups;

$R^7$ and $R^9$ each independently represent a hydrogen atom or a $C_1$–$C_6$, particularly $C_1$–$C_4$, alkyl (e.g. methyl, ethyl, propyl, butyl, pentyl or hexyl) or phenyl group, each of which may be optionally substituted by one or more (e.g. one, two, three or four) substituent groups independently selected from halogen atoms (e.g. fluorine, chlorine, bromine or iodine), phenyl, —$OR^{17}$ and —$NR^{15}R^{16}$; and each of $R^8$, $R^{10}$, $R^{11}$, $R^{12}$, $R^{15}$, $R^{16}$ and $R^{17}$ independently represents a hydrogen atom or a $C_1$–$C_6$, particularly $C_1$–$C_4$, alkyl (e.g. methyl, ethyl, propyl, butyl, pentyl or hexyl) or phenyl group; with the proviso that when $R^1$ and X both represent —$NH_2$, then $R^2$ does not represent a methyl group;

or a pharmaceutically acceptable salt or solvate thereof.

In the context of the present specification, unless otherwise indicated, an alkyl or alkenyl group or an alkyl or alkenyl moiety in a substituent group may be linear or branched. Where a substituent in an alkenyl group is a phenoxy group, the phenoxy group is not attached to an unsaturated carbon atom. A carbocyclic group is a saturated hydrocarbyl group that may be monocyclic or polycyclic (e.g. bicyclic). Similarly, a saturated heterocyclic ring system may be monocyclic or polycyclic (e.g. bicyclic).

In formula (I) above, the group $R^1$ represents a hydrogen atom, or a group —$NR^3R^4$. Particularly advantageous compounds of formula (I) are those in which $R^1$ represents a group —$NR^3R^4$.

Preferably, $R^3$ and $R^4$ each independently represent a hydrogen atom, or a 4-piperidinyl, $C_3$–$C_6$ cycloalkyl (i.e. cyclopropyl, cyclobutyl, cyclopentyl or cyclohexyl) or $C_1$–$C_8$, particularly $C_1$–$C_6$, alkyl group (e.g. methyl, ethyl, propyl, isopropyl, butyl, isobutyl, t-butyl, pentyl, hexyl, heptyl or octyl), which latter two groups may be optionally substituted by one, two, three or four substituent groups independently selected from halogen atoms (e.g. fluorine, chlorine, bromine or iodine) and —$NR^5R^6$, —$CONR^5R^6$, —$OR^7$, —$COOR^7$, —$NR^8COR^9$, —$SR^{10}$, —$SO_2R^{10}$, —$SO_2NR^5R^6$, —$NR^8SO_2R^9$, morpholinyl, $C_1$–$C_4$ alkyl (e.g. methyl, ethyl, propyl, isopropyl, butyl or t-butyl), $C_3$–$C_6$ cycloalkyl (i.e. cyclopropyl, cyclobutyl, cyclopentyl or cyclohexyl), tetrahydrofuranyl and aryl groups, wherein an aryl substituent group may be a phenyl, naphthyl, thienyl, pyridinyl, imidazolyl or indolyl group, each of which may be optionally substituted by one, two, three or four substituents independently selected from halogen atoms (e.g. fluorine, chlorine, bromine or iodine) and cyano, nitro, —$NR^5R^6$, $CONR^5R^6$, —$OR^7$, —$NR^8COR^9$, —$SO_2NR^5R^6$, —$NR^8SO_2R^9$, $C_1$–$C_6$, particularly $C_1$–$C_4$, alkyl (e.g. methyl, ethyl, propyl, butyl, pentyl or hexyl) and trifluoromethyl groups, or $R^3$ and $R^4$ together with the nitrogen atom to which they are attached form a 4- to 7-membered saturated heterocyclic ring system, which ring system may be optionally substituted by one, two or three substituent groups independently selected from

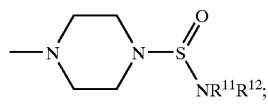

—$NR^5R^6$, —$CONR^5R^6$, —$OR^7$, —$COOR^{10}$, —$NR^8COR^9$, and $C_1$–$C_6$, particularly $C_1$–$C_4$, alkyl (e.g. methyl, ethyl, propyl, butyl, pentyl or hexyl) optionally substituted by one, two or three substituents independently selected from halogen atoms (e.g. fluorine, chlorine, bromine or iodine) and —$NR^{11}R^{12}$ and —$OR^7$ groups.

Particularly advantageous compounds of formula (I) are those in which $R^3$ and $R^4$ each independently represent a hydrogen atom, or a $C_1$–$C_6$ alkyl group substituted by a —$CONR^5R^6$ or imidazolyl (e.g. 1H-imidazol-4-yl) group.

Preferably, $R^2$ represents a $C_1$–$C_6$ alkyl or $C_2$–$C_6$ alkenyl group optionally substituted by a phenyl or phenoxy group, wherein the phenyl or phenoxy group may itself be optionally substituted by one, two, three or four substituents independently selected from halogen atoms (e.g. fluorine, chlorine, bromine or iodine) and nitro, $C_1$–$C_6$, particularly $C_1$–$C_4$, alkyl (e.g. methyl, ethyl, propyl, butyl, pentyl or hexyl), trifluoromethyl, —$OR^7$, —$C(O)R^7$, —$SR^{10}$, —$NR^{15}R^{16}$ and phenyl groups.

Particularly advantageous compounds of formula (I) are those in which $R^2$ represents a $C_1$–$C_6$ alkyl group optionally substituted by a phenyl, halophenyl (e.g. 2,3-difluorophenyl) or —$OR^7$ (e.g. phenoxy) group.

Preferably, $R^5$ and $R^6$ each independently represent a hydrogen atom or a $C_1$–$C_6$, particularly $C_1$–$C_4$, alkyl or phenyl group, each of which may be optionally substituted by dione, two, three or four substituent groups independently selected from halogen atoms (e.g. fluorine, chlorine, bromine or iodine), phenyl, —$OR^7$ and —$NR^{15}R^{16}$, or $R^5$ and $R^6$ together with the nitrogen atom to which they are attached form a 4- to 7-membered saturated heterocyclic ring system optionally comprising a further heteroatom selected from oxygen and nitrogen atoms (e.g. one or two oxygen and/or nitrogen atoms), which ring system may be optionally substituted by one, two or three substituent groups independently selected from phenyl, —$OR^{17}$, —$COOR^{17}$, —$NR^{15}R^{16}$, —$CONR^{15}R^{16}$, —$NR^{15}COR^{16}$, —$SONR^{15}R^{16}$, and $C_1$–$C_6$, particularly $C_1$–$C_4$, alkyl (e.g. methyl, ethyl, propyl, butyl, pentyl or hexyl) optionally substituted by one, two or three substituents independently selected from halogen atoms (e.g. fluorine, chlorine, bromine or iodine) and —$NR^{15}R^{16}$ and —$OR^{17}$ groups.

Preferably, $R^{13}$ and $R^{14}$ each independently represent a hydrogen atom, a 4-piperidinyl group optionally substituted by a $C_1$–$C_4$ alkylphenyl substituent group, or a $C_3$–$C_7$ carbocyclic, $C_1$–$C_8$, particularly $C_1$–$C_6$, alkyl (e.g. methyl, ethyl, propyl, isopropyl, butyl, isobutyl, t-butyl, pentyl, hexyl, heptyl or octyl), $C_2$–$C_6$ alkenyl (ethenyl, propenyl, butenyl, pentenyl or hexenyl) or $C_2$–$C_6$ alkynyl (ethynyl, propynyl, butynyl, pentynyl or hexynyl) group, which latter four groups may be optionally substituted by one, two, three or four substituent groups independently selected from halogen atoms (e.g. fluorine, chlorine, bromine or iodine) and —$NR^5R^6$, —$CONR^5R^6$, —$OR^7$, —$COOR^7$, —$NR^8COR^9$, —$SR^{10}$, —$SO_2R^{10}$, —$SO_2NR^5R^6$, —$NR^8SO_2R^9$, morpholinyl, $C_1$–$C_4$ alkyl (e.g. methyl, ethyl, propyl, isopropyl, butyl or t-butyl), $C_3$–$C_6$ cycloalkyl (i.e. cyclopropyl, cyclobutyl, cyclopentyl or cyclohexyl), and aryl groups, wherein an aryl substituent group may be a phenyl, naphthyl, thienyl, pyridinyl, imidazolyl or indolyl group, each of which may be optionally substituted by one, two, three or four substituents independently selected from halogen atoms (e.g. fluorine, chlorine, bromine or iodine) and cyano, nitro, —$NR^5R^6_1$ —$CONR^5R^6$, —$OR^7$, —$NR^8COR^9$, —$SO_2NR^5R^6$, $NR^8SO_2R^9$, $C_1$–$C_6$, particularly $C_1$–$C_4$, alkyl (e.g. methyl, ethyl, propyl, butyl, pentyl or hexyl) and trifluoromethyl groups, or $R^{13}$ and $R^{14}$ together with the nitrogen atom to which they are attached form a 4- to 7-membered saturated heterocyclic ring system, which ring system may be optionally substituted by one, two or three substituent groups independently selected from —$NR^5R^6$, —$CONR^5R^6$, —$OR^7$, —$COOR^7$, —$NR^8COR^9$, and $C_1$–$C_6$, particularly $C_1$–$C_4$, alkyl (e.g. methyl, ethyl, propyl, butyl, pentyl or hexyl) optionally substituted by one, two or three substituents independently selected from halogen atoms (e.g. fluorine, chlorine, bromine or iodine) and phenyl, —NR$^{11}$R$^{12}$ and —OR$^7$ groups;

Particularly advantageous compounds of formula (I) are those in which one of R$^{13}$ and R$^{14}$ represents a hydrogen atom and the other of R$^{13}$ and R$^{14}$ represents a C$_1$–C$_6$ alkyl group substituted by an —OR$^7$ group, e.g. —CH(CH$_2$CH$_3$)CH$_2$OH, —C(CH$_3$)$_2$CH$_2$OH or CH(CH$_2$CH(CH$_3$)$_2$)CH$_2$OH.

Particularly preferred compounds of the invention include:

(2R)-2-[[2-Amino-5-[(phenylmethyl)thio]thiazolo[4,5-d]pyrimidin-7-yl]amino]-1-butanol,
(S)-2-[[2-Amino-5-[(phenylmethyl)thio]thiazolo[4,5-d]pyrimidin-7-yl]amino]-1-butanol,
2-Amino-5-[[(2,3-difuorophenyl)methyl]thio]thiazolo[4,5-d]pyrimidin-7(4H)-one,
5-[[(3-Phenoxyphenyl)methyl]thio]thiazolo[4,5-d]pyrimidin-7(4H)-one,
2-Amino-5-[[(3-phenoxyphenyl)methyl]thio]thiazolo[4,5-d]pyrimidin-7(4H)-one,
(±)-2-[[2-Amino-5-(pentylthio)thiazolo[4,5-d]pyrimidin-7-yl]amino]-1-butanol,
2-[[2-Amino-5-(pentylthio)thiazolo[4,5-d]pyrimidin-7-yl]amino]ethanol,
5-(Pentylthio)thiazolo[4,5-d]pyrimidin-7(4H)-one,
2-Amino-5-[(phenylmethyl)thio]thiazolo[4,5-d]pyrimidin-7(4H)-one,
2-Amino-5-(pentylthio)thiazolo[4,5-d]pyrimidin-7(4H)-one,
2-[[3-(Dimethylamino)propyl]amino]-5-(pentylthio)thiazolo[4,5-d]pyrimidin-7(4H)-one,
2-[[2-(Diethylamino)ethyl]amino]-5-(pentylthio)thiazolo[4,5-d]pyrimidin-7(4H)-one,
2-[[2-(Dimethylamino)ethyl]amino]-5-(pentylthio)thiazolo[4,5-d]pyrimidin-7(4H)-one,
2-[(3-Hydroxypropyl)amino]-5-(pentylthio)thiazolo[4,5-d]pyrimidin-7(4H)-one,
2-[[2-(Acetylamino)ethyl]amino]-5-(pentylthio)thiazolo[4,5-d]pyrimidin-7(4H)-one,
(±)-2-[(2,3-Dihydoxypropyl)amino]-5-(pentylthio)thiazolo[4,5-d]pyrimidin-7(4H)-one,
2-[[2-(4-Morpholinyl)ethyl]amino]-5-(pentylthio)thiazolo[4,5-d]pyrimidin-7(4H)-one,
2-[(2-Methoxyethyl)amino]-5-(pentylthio)thiazolo[4,5-d]pyrimidin-7(4H)-one,
2-[(1-Methylethyl)amino]-5-(pentylthio)thiazolo[4,5-d]pyrimidin-7(4H)-one,
2-(Cyclopropylamino)-5-(pentylthio)thiazolo[4,5-d]pyrimidin-7(4H)-one,
(±)-2-[(2-Hydoxypropyl)amino]-5-(pentylthio)thiazolo[4,5-d]pyrimidin-7(4H)-one,
2-[[2-(2-Hydroxyethoxy)ethyl]amino]-5-(pentylthio)thiazolo[4,5-d]pyrimidin-7(4H)-one,
2-[(2-Hydroxy-2-methylpropyl)amino]-5-(pentylthio)thiazolo[4,5-d]pyrimidin-7(4H)-one,
2-[(2-Hydroxyethyl)amino]-5-(pentylthio)thiazolo[4,5-d]pyrimidin-7(4H)-one,
(2S,3R)-3-Hydroxy-2-[(7-oxo-5-(pentylthio)-4H-thiazolo[4,5-d]pyrimidin-2-yl]amino)butanamide,
N$^7$-[3-(Dimethylamino)propyl]-5-(pentylthio)thiazolo[4,5-d]pyrimidine-2,7-diamine,
N$^7$-[2-(Diethylamino)ethyl]-5-(pentylthio)thiazolo[4,5-d]pyrimidine-2,7-diamine,
N$^7$-[2-(Dimethylamino)ethyl]-5-(pentylthio)thiazolo[4,5-d]pyrimidine-2,7-diamine,
3-[(2-Amino-5-(pentylthio)thiazolo[4,5-d]pyrimidin-7-yl)amino]-1-propanol,
N$^7$-Cyclohexyl-5-(pentylthio)thiazolo[4,5-d]pyrimidine-2,7-diamine,
(±)-3-[(2-Amino-5-((phenylmethyl)thio)thiazolo[4,5-d]pyrimidin-7-yl)amino]-1,2-propanediol,
N$^7$-(2-Methoxyethyl)-5-(pentylthio)thiazolo[4,5-d]pyrimidine-2,7-diamine,
5-(Pentylthio)-N$^7$-propylthiazolo[4,5-d]pyrimidine-2,7-diamine,
N$^7$-Cyclopentyl-5-(pentylthio)thiazolo[4,5-d]pyrimidine-2,7-diamine,
N$^7$-Cyclopropyl-5-(pentylthio)thiazolo[4,5-d]pyrimidine-2,7-diamine,
N$^7$-(2-Methylpropyl)-5-(pentylthio)thiazolo[4,5-d]pyrimidine-2,7-diamine,
(±)-1-[(2-Amino-5-(pentylthio)thiazolo[4,5-d]pyrimidin-7-yl)amino]-2-propanol,
(exo)-N$^7$-Bicyclo[2.2.1]hept-2-yl-5-(pentylthio)thiazolo[4,5-d]pyrimidine-2,7-diamine,
2-[2-[[2-Amino-5-(pentylthio)thiazolo[4,5-d]pyrimidin-7-yl]amino]ethoxy]ethanol,
(±)-N$^7$-(2-Methylbutyl)-5-(pentylthio)thiazolo[4,5-d]pyrimidine-2,7-diamine,
1-[[2-Amino-5-(pentylthio)thiazolo[4,5-d]pyrimidin-7-yl]amino]-2-methyl-2-propanol,
N$^7$-[(2-Aminophenyl)methyl]-5-(pentylthio)thiazolo[4,5-d]pyrimidine-2,7-diamine,
2-Amino-5-[(2-phenoxyethyl)thio]thiazolo[4,5-d]pyrimidin-7(4H)-one,
(E)-2-Amino-5-[(3-phenyl-2-propenyl)thio]thiazolo[4,5-d]pyrimidin-7(4H)-one,
2-Amino-5-[[3-[2,4-bis(1,1-dimethylethyl)phenoxy]propyl]thio]thiazolo[4,5-d]pyrimidin-7(4H)-one,
2-Amino-5-[[[(4-trifluoromethyl)phenyl]methyl]thio]thiazolo[4,5-d]pyrimidin-7(4H)-one,
2-Amino-5-[[(3,5-dichlorophenyl)methyl]thio]thiazolo[4,5-d]pyrimidin-7(4H)-one,
2-Amino-5-[[(2,4-dichlorophenyl)methyl]thio]thiazolo[4,5-d]pyrimidin-7(4H)-one,
2-Amino-5-[[(3,4-dichlorophenyl)methyl]thio]thiazolo[4,5-d]pyrimidin-7(4H)-one,
2-Amino-5-[[(3.5-dibromophenyl)methyl]thio]thiazolo[4,5-d]pyrimidin-7(4H)-one,
2-Amino-5-[[(2-nitrophenyl)methyl]thio]thiazolo[4,5-d]pyrimidin-7(4H)-one,
2-Amino-5-[[(2-fluorophenyl)methyl]thio]thiazolo[4,5-d]pyrimidin-7(4H)-one,
2-Amino-5-[[(2-iodophenyl)methyl]thio]thiazolo[4,5-d]pyrimidin-7(4H)-one,
2-Amino-5-[[(3-chlorophenyl)methyl]thio]thiazolo[4,5-d]pyrimidin-7(4H)-one,
2-Amino-5-[[(3-chlorophenyl)methyl]thio]thiazolo[4,5-d]pyrimidin-7(4H)-one,
2-Amino-5-[[(4-chloro-2-nitrophenyl)methyl]thio]thiazolo[4,5-d]pyrimidin-7(4H)-one,
2-Amino-5-[[(3-chloro-4-methoxyphenyl)methyl]thio]thiazolo[4,5-d]pyrimidin-7(4H)-one, 2-Amino-5-[[(2,3-dichlorophenyl)methyl]thio]thiazolo[4,5-d]pyrimidin-7(4H)-one, 2-Amino-5-[[(3,5-difluorophenyl)methyl]thio]thiazolo[4,54-d]pyrimidin-7(4H)-one, 2-Amino-5-[[[(2,4-bis(trifluoromethyl)phenyl]methyl]thio]thiazolo[4,5-d]pyrimidin-7(4H)-one, 2-Amino-5-[[(2-bromophenyl)methyl]thio]thiazolo[4,5-d]pyrimidin-7(4H)-one, 2-Amino-5-[[(2,3,4-trifuorophenyl)methyl]thio]thiazolo[4,5-d]pyrimidin-7(4H)-one, 2-Amino-5-[[(3-bromophenyl)methyl]thio]thiazolo[4,5-d]pyrimidin-7(4H)-one, 2-Amino-5-[[(2-fluoro-3-methylphenyl)methyl]thio]thiazolo[4,5-d]pyrimidin-7(4H)-one, 3-[[2-Amino-5-[(phenylmethyl)thio]thiazolo[4,5-d]pyrimidin-7-yl]amino]-2,2-dimethyl-1-propanol, (±)-α-[[[2-Amino-5-[(phenylmethyl)thio]thiazolo[4,5-d]pyrimidin-7-yl]amino]methyl]benzenemethanol, (R)-β-[[2-Amino-5-[(phenylmethyl)thio]thiazolo[4,5-d]pyrimidin-7-yl]amino]benzenepropanol, 2-[[2-Amino-5-[(phenylmethyl)thio]thiazolo[4,5-d]pyrimidin-7-yl]amino]ethanol, (2R)-2-[[2-Amino-5-[(phenylmethyl)thio]thiazolo[4,5-d]pyrimidin-7-yl]amino]-4-methylpentanol, (±)-1-[[2-Amino-5-[(phenylmethyl)thio]thiazolo[4,5-d]pyrimidin-7-yl]amino]-2-propanol, (±)-5-[[2-Amino-5-[(phenylmethyl)thio]thiazolo[4,5-d]pyrimidin-7-yl]amino]-4-chlorobenzenepropanol, (±)-3-[[2-Amino[(phenylmethyl)thio]thiazolo[4,5-d]pyrimidin-7-yl]amino]-1,2-propanediol, 2-[[2-Amino-5-[(phenylmethyl)thio]thiazolo[4,5-d]pyrimidin-7-yl]propylamino]ethanol, (±)-1-[2-Amino-5-[(phenylmethyl)thio]thiazolo[4,5-d]pyrimidin-7-yl]-3-pyrrolidinol, (±)-1-[2-Amino-5-[(phenylmethyl)thio]thiazolo[4,5-d]pyrimidin-7-yl]-3-piperidinol, 1-[2-Amino-5-[(phenylmethyl)thio]thiazolo[4,5-d]pyrimidin-7-yl]-4-piperidinol, 3-[[2-Amino-5-[[(3-phenoxyphenyl)methyl]thio]thiazolo[4,5-d]pyrimidin-7-yl]amino]-2,2-dimethyl-1-propanol, (±)-2-[[2-Amino-5-[[(3-phenoxyphenyl)methyl]thio]thiazolo[4,5-d]pyrimidin-7-yl]amino]-1-butanol, (±)-α-[[[2-Amino-5-[[(3-phenoxyphenyl)methyl]thio]thiazolo[4,5-d]pyrimidin-7-yl)-2-amino]methyl]benzenemethanol, 4-[[2-Amino-5-[[(3-phenoxyphenyl)methyl]thio]thiazolo[4,5-d]pyrimidin-7-yl]amino]-1-butanol, 6-[[2-Amino-5-[[(3-phenoxyphenyl)methyl]thio]thiazolo[4,5-d]pyrimidin-7-yl]amino]-1-hexanol, 4-[[2-Amino-5-[[(3-phenoxyphenyl)methyl]thio]thiazolo[4,5-d]pyrimidin-7-yl]amino]cyclohexanol, (R)-β-[[2-Amino-5-[[(3-phenoxyphenyl)methyl]thio]thiazolo[4,54-d]pyrimidin-7-yl]amino]benzenepropanol, (±)-2-[[2-Amino-5-[[(3-phenoxyphenyl)methyl]thio]thiazolo[4,5-d]pyrimidin-7-yl]amino]-1-propanol, 2-[[2-Amino-5-[[(3-phenoxyphenyl)methyl]tho]thiazolo[4,5-d]pyrimidin-7-yl]amino]ethanol, (2R)-2-[[2-Amino-5-[[(3-phenoxyphenyl)methyl]thio]thiazolo[4,5-d]pyrimidin-7-yl]amino]-4-methylpentanol, (±)-1-Amino-3-[[2-Amino-5-[[(3-phenoxyphenyl)methyl]thio]thiazolo[4,5-d]pyrimidin-7-yl]amino]-2-propanol, (±)-1-[[2-Amino-5-[[(3-phenoxyphenyl)methyl]thio]thiazolo[4,5-d]pyrimidin-7-yl]amino]-2-propanol, 2-[[[2-Amino-5-[[(3-phenoxyphenyl)methyl]thio]thiazolo[4,5-d]pyrimidin-7-yl]amino]methyl]-2-ethyl-1,3-propanediol, (±)-β-[[2-Amino-5-[[(3-phenoxyphenyl)methyl]thio]thiazolo[4,5-d]pyrimidin-7-yl]amino]-4-chlorobenzenepropanol, (±)-3-[[2-Amino-5-[[(3-phenoxyphenyl)methyl]thio]thiazolo[4,5-d]pyrimidin-7-yl]amino]-1,2-propanediol, 2-[[2-[[2-Amino-5-[[(3-phonoxyphenyl)methyl]thio]thiazolo[4,5-d]pyrimidin-7-yl]amino]ethyl]amino]ethanol, 3-[[2-Amino-5-[[(3-phenoxyphenyl)methyl]thio]thiazolo[4,5-d]pyrimidin-7-yl]amino]-1-propanol, (±)-α-[[(2-Amino-5-[[(3-phenoxyphenyl)methyl]thio]thiazolo[4,5-d]pyrimidin-7-yl]amino]methyl]-3,4-dichlorobenzenepropanol, 1-[[2-Amino-5-[[(3-phenoxyphenyl)methyl]thio]thiazolo[4,5-d]pyrimidin-7-yl]amino]-2-methyl-2-propanol, 2-[2-[[2-Amino-5-[[(3-phenoxyphenyl)methyl]thio]thiazolo[4,5-d]pyrimidin-7-yl]amino]ethoxy]ethanol, 5-[[2-Amino-5-[[(3-phenoxyphenyl)methyl]thio]thiazolo[4,5-d]pyrimidin-7-yl]amino]-1-pentanol, (2S)-2-[[2-Amino-5-[[(3-phenoxyphenyl)methyl]thio]thiazolo[4,5-d]pyrimidin-7-yl]amino]-4-(methylthio)-1-butanol, 2-[[2-Amino-5-[[(3-phenoxyphenyl)methyl]thio]thiazolo[4,5-d]pyrimidin-7-yl]butylamino]ethanol, 2-[[2-Amino-5-[[(3-phenoxyphenyl)methyl]thio]thiazolo[4,5-d]pyrimidin-7-yl]propylamino]ethanol, 2,2'-[[2-Amino-5-[[(3-phenoxyphenyl)methyl]thio]thiazolo[4,5-d]pyrimidin-7-yl]imino]bisethanol, 2-[[[2-Amino-5-[[(3-phenoxyphenyl)methyl]thio]thiazolo[4,5-d]pyrimidin-7-yl]-(2-hydroxyethyl)amino]methyl]phenol, 3-[[2-Amino-5-[[(3-phenoxyphenyl)methyl]thio]thiazolo[4,5-d]pyrimidin-7-yl]-(2-hydroxyethyl)amino]-1-propanol, (±)-1-[2-Amino-5-[[(3-phenoxyphenyl)methyl]thio]thiazolo[4,5-d]pyrimidin-7-yl]-3-pyrrolidinol, (trans)-1-[2-Amino-5-[[(3-phenoxyphenyl)methyl]thio]thiazolo[4,5-d]pyrimidin-7-yl]-4-hydroxy-L-proline phenylmethyl ester, (±)-1-[2-Amino-5-[[(3-phenoxyphenyl)methyl]thio]thiazolo[4,5-d]pyrimidin-7-yl]-3-piperidinemethanol, (±)-1-[2-Amino-5-[[(3-phenoxyphenyl)methyl]thio]thiazolo[4,5-d]pyrimidin-7-yl]-3-piperidinol, (2S)-1-[2-Amino-5-[[(3-phenoxyphenyl)methyl]thio]thiazolo[4,5-d]pyrimidin-7-yl]-2-pyrrolidinemethanol, 1-[2-Amino-5-[[(3-phenoxyphenyl)methyl]thio]thiazolo[4,5-d]pyrimidin-7-yl]-4-piperidinol, (2R)-2-[[2-Amino-5-[[(3-phenoxyphenyl)methyl]thio]thiazolo[4,5-d]pyrimidin-7-yl]amino]-1-butanol, (2S)-2-[[2-Amino-5-[[(3-phenoxyphenyl)methyl]thio]thiazolo[4,5-d]pyrimidin-7-yl]amino]-1-butanol, (2R)-2-[[2-Amino-5-[[(2,3-difluorophenyl)methyl]thio]thiazolo[4,5-d]pyrimidin-7-yl]amino]-1-butanol, 2-[[2-Amino-5-[[(3-phenoxyphenyl)methyl]thio]thiazolo[4,5-d]pyrimidin-7-yl]amino]-1,3-propanediol, 2-[[2-Amino-5-[[(3-phenoxyphenyl)methyl]thio]thiazolo[4,5-d]pyrimidin-7-yl]amino]-2-methyl-1-propanol, 2-[[2-Amino-5-[[(2,3-difluorophenyl)methyl]thio]thiazolo[4,5-d]pyrimidin-7-yl]amino]-2-methyl-1-propanol, 2-[[2-Amino-5-[[(2,3-difluorophenyl)methyl]thio]thiazolo[4,5-d]pyrimidin-7-yl]amino]-2-methyl-2-propanol, 5-[[(2,3-Difluorophenyl)methyl]thio]-$N^7$-(2-fluoroethyl)thiazolo[4,5-d]pyrimidine-2,7-diamine, (1R-trans) 2-[[2-Amino-5-[[(2,3-difluorophenyl)methyl]thio]thiazolo[4,5-d]pyrimidin-7-yl]amino]-cyclopentanol, (1S-trans) 2-[[2-Amino-5-[[(2,3-difluorophenyl)methyl]thio]thiazolo[4,5-d]pyrimidin-7-yl]amino]-cyclopentanol, 2-[[2-Amino-5-[(phenylmethyl)thio]thiazolo[4,5-d]pyrimidin-7-yl]amino]-2-methyl-1-propanol, 2-Methyl-2-[[2-(methylamino)-5-[(phenylmethyl)thio]thiazolo[4,5-d]pyrimidin-7-yl]amino]-1-propanol, 2-[[2-[[5-[((2,3-Difluorophenyl)methyl]thio]-2-[(phenylmethyl)amino]thiazolo[4,5-d]pyrimidin-7-yl]amino]-2-methyl-1-propanol, 5-[[(2,3-Difluorophenyl)methyl]thio]thiazolo[4,5-d]pyrimidin-7(4H)-one, (±)-2-[[2-Amino-5-[[(2,3-difluorophenyl)methyl]thio]thiazolo[4,5-d]pyrimidin-7-yl]amino]-1-butanol, (1S,2S)-2-[[2-Amino-5-[[(2,3-difluorophenyl)methyl]thio]thiazolo[4,5-d]pyrimidin-7-yl]amino]-cyclohexanol, (±)-2-[[2-Amino-5-[[(2,3-difluorophenyl)methyl]thio]thiazolo[4,5-d]pyrimidin-7-yl]amino]-1-propanol, 2-[[2-Amino-5-[[(2,3-difluorophenyl)methyl]thio]thiazolo[4,5-d]pyrimidin-7-yl]amino]-1-ethanol, (2R)-2-[[2-Amino-5-[[(2,3-difluorophenyl)methyl]thio]thiazolo[4,5-d]pyrimidin-7-yl]amino]-4-methyl-1-pentanol, (±)-1-[[2-Amino-5-[[(2,3-difluorophenyl)methyl]thio]thiazolo[4,5-d]pyrimidin-7-yl]amino]-2-propanol, 2-[[2-Amino-5-[[(2,3-difluorophenyl)methyl]thio]thiazolo[4,5-d]pyrimidin-7-yl]amino]-2-methyl-1,3-propanediol, 1-[[[2-Amino-5-[[(2,3-difluorophenyl)methyl]thio]thiazolo[4,5-d]pyrimidin-7-yl]amino]methyl]-cyclohexanol, (2R)-2-[[2-Amino-5-[[(2,3-difluorophenyl)methyl]thio]thiazolo[4,5-d]pyrimidin-7-yl]amino]-1-butanol, 2-[[2-Amino-5-[[(2,3-difluorophenyl)methyl]thio]thiazolo[4,5-d]pyrimidin-7-yl](2-aminoethyl)amino]-1-ethanol, 2-[2-[[2-Amino-5-[[(2,3-difluorophenyl)methyl]thio]thiazolo[4,5-d]pyrimidin-7-yl]amino]ethoxy]-1-ethanol, (αS)-α-(1R)-1-[[2-Amino-5-[[(2,3-difluorophenyl)methyl]thio]thiazolo[4,5-d]pyrimidin-7-yl]methylamino]ethyl]-benzenemethanol, 1-[2-Amino-5-[[(2,3-difluorophenyl)methyl]thio]thiazolo[4,5-d]pyrimidin-7-yl]-4-piperidinol, 5-[[(2,3-Difluorophenyl)methyl]thio]-$N^7$-ethyl-thiazolo[4,5-d]pyrimidine-2,7-diamine, 5-[[(2,3-Difluorophenyl)methyl]thio-$N^7$-(2-propenyl)-thiazolo[4,5-d]pyrimidine-2,7-diamine, (1S,2S)-2-[[2-Amino-5-[[(2,3-difluorophenyl)methyl]thio]thiazolo[4,5-d]pyrimidin-7-yl]amino]-1-phenyl-1,3-propanediol, 2-[[2-Amino-5-[[(2,3-difluorophenyl)methyl]thio]thiazolo[4,5-d]pyrimidin-7-yl]amino]-1,3-propanediol, 2-[[2-Amino-5-[[(2,3-difluorophenyl)methyl]thio]thiazolo[4,5-d]pyrimidin-7-yl]amino]-1-ethanol, (±)-5-[[(2,3-Difluorophenyl)methyl]thio]-$N^7$-(2-methoxy-1-methylethyl)-thiazolo[4,5-d]pyrimidine-2,7-diamine, $N^7$-Cyclopropyl-5-[[(2,3-difluorophenyl)methyl]thio]-thiazolo[4,5-d]pyrimidine-2,7-diamine, (±)-2-[[2-Amino-5-[(2,3-difluorophenyl)methyl]thio]-thiazolo[4,5-d]pyrimidin-7-yl]amino]-1-propanol, 4-[[2-Amino-5-[[(2,3-difluorophenyl)methyl]thio]-thiazolo[4,5-d]pyrimidin-7-yl]amino]-1-butanol, 5-[[(2,3-Difluorophenyl)methyl]thio]-$N^7$-[2-(1H-imidazol-4-yl)ethyl]-thiazolo[4,5-d]pyrimidine-2,7-diamine, (±)-N-[5-[[(2,3-Difluorophenyl)methyl]thio]-7-[(2-hydroxy-1,1-dimethylethyl)amino]thiazolo[4,5-d]pyrimidin-2-yl]-serine, methyl ester, 2-[[5-[[(2,3-Difluorophenyl)methyl]thio]-2-[(1-methylethyl)amino]thiazolo[4,5-d]pyrimidin-7-yl]amino]-2-methyl-1-propanol, 2-[[5-[[(2,3-Difluorophenyl)methyl]thio]-2-(ethylamino)thiazolo[4,5-d]pyrimidin-7-yl]amino]-2-methyl-1-propanol, 2-[[5-[[(2,3-Difluorophenyl)methyl]thio]-2-[2-(1H-indol-3-yl)ethyl]amino]thiazolo[4,5-d]pyrimidin-7-yl]amino]-2-methyl-1-propanol, 2-[[5-[[(2,3-Difluorophenyl)methyl]thio]-2-[(1-naphthalenylmethyl)amino]thiazolo[4,5-d]pyrimidin-7-yl]amino]-2-methyl-1-propanol, 2-[[5-[[(2,3-Difluorophenyl)methyl]thio]-2-[(1,2-diphenylethyl)amino]thiazolo[4,5-d]pyrimidin-7-yl]amino]-2-methyl-1-propanol, 2-[[5-[[(2,3-Difluorophenyl)methyl]thio]-2-[(2,2,2-trifluoroethyl)amino]thiazolo[4,5-d]pyrimidin-7-yl]amino]-2-methyl-1-propanol, 2-[[5-[[(2,3-Difluorophenyl)methyl]thio]-2-[[(3,4,5-trimethoxyphenyl)methyl]amino]thiazolo[4,5-d]pyrimidin-7-yl]amino]-2-methyl-1-propanol, 2-[[5-[[(2,3-Difluorophenyl)methyl]thio]-2-[(1,1-dimethylethyl)amino]thiazolo[4,5-d]pyrimidin-7-yl]amino]-2-methyl-1-propanol, 2-[[5-[[(2,3-Difluorophenyl)methyl]thio]-2-[[2-(2-thienyl)ethyl]amino]thiazolo[4,5-d]pyrimidin-7-yl]amino]-2-methyl-1-propanol, 2-[[5-[[(2,3-Difluorophenyl)methyl]thio]-2-[(4-methylcyclohexyl)amino]thiazolo[4,5-d]pyrimidin-7-yl]amino]-2-methyl-1-propanol, 2-[[5-[[(2,3-Difluorophenyl)methyl]thio]-7-[(2-hydroxy-1,1-dimethylethyl)amino]thiazolo[4,5-d]pyrimidin-2-yl]amino]-acetamide, 2-[[2-[[2-(4-Aminophenyl)ethyl]amino]-5-[[(2,3-difluorophenyl)methyl]thio]thiazolo[4,5-d]pyrimidin-7-yl]amino]-2-methyl-1-propanol, 2-[[5-[[(2,3-Difluorophenyl)methyl]thio]-2-[(2-fluoroethyl)amino]thiazolo[4,5-d]pyrimidin-7-yl]amino]-2-methyl-1-propanol, 2-[[2-(Cyclopropylamino)-5-[[(2,3-difluorophenyl)methyl]thio]thiazolo[4,5-d]pyrimidin-7-yl]amino]-2-methyl-1-propanol, (±)-2-[[5-[[(2,3-Difluorophenyl)methyl]thio]-7-[(2-hydroxy-1,1-dimethylethyl)amino]thiazolo[4,5-d]pyrimidin-2-yl]amino]-1-pentanol, 2-[[5-[[(2,3-Difluorophenyl)methyl]thio]-2-[[2-(2-hydroxyethoxy)ethyl]amino]thiazolo[4,5-d]pyrimidin-7-yl]amino]-2-methyl-1-propanol, N-[5-[[(2,3-Difluorophenyl)methyl]thio]-6,7-dihydro-7-oxo-thiazolo[4,5-d]pyrimidin-2-yl]-DL-serine, methyl ester, 5-[[(2,3-Difluorophenyl)methyl]thio]-2-[(1-methylethyl)amino]-thiazolo[4,5-d]pyrimidin-7(4H)-one, 5-[[(2,3-Difluorophenyl)methyl]thio]-2-[[2-(1H-indol-3-yl)ethyl]amino]-thiazolo[4,5-d]pyrimidin-7(4H)-one, 2-[[5-[[(2,3-Difluorophenyl)methyl]thio]-6,7-dihydro-7-oxo-thiazolo[4,5-d]pyrimidin-2-yl]amino]-acetamide, 2-[[2-(4-Aminophenyl)ethyl]amino]-5-[[(2,3-difuorophenyl)methyl]thio]-thiazolo[4,5-d]pyrimidin-7(4H)-one, 5-[[(2,3-Difluorophenyl)methyl]thio]-2-[(2-fluoroethyl)amino]-thiazolo[4,5-d]pyrimidin-7(4H)-one, 5-[[(2,3-Difluorophenyl)methyl]thio]-2-[[2-(2-hydroxyethoxy)ethyl]amino]-thiazolo[4,5-d]pyrimidin-7(4H)-one, 2-[[2-(Cyclohexylamino)-5-[(phenylmethyl)thio]thiazolo[4,5-d]pyrimidin-7-yl]amino]-2-methyl-1-propanol, 2-[[2-[(1,1-Dimethylethyl)amino]-5-[(phenylmethyl)thio]thiazolo[4,5-d]pyrimidin-7-yl]amino]-2-methyl-1-propanol, N-[7-[(2-Hydroxy-1,1-dimethylethyl)amino]-5-[(phenylmethyl)thio]thiazolo[4,5-d]pyrimidin-2-yl]-DL-alanine, methyl ester, 4-[[7-[(2-Hydroxy-1,1-dimethylethyl)amino]-5-[(phenylmethyl)thio]thiazolo[4,5-d]pyrimidin-2-yl]amino]-cyclohexanol, 2-Methyl-2-[[2-[(4-phenylbutyl)amino]-5-[(phenylmethyl)thio]thiazolo[4,5-d]pyrimidin-7-yl]amino]-1-propanol, 2-Methyl-2-[[5-[(phenylmethyl)thio]-2-[[(tetrahydro-2-furanyl)methyl]amino]thiazolo[4,5-d]pyrimidin-7-yl]amino]-1-propanol, 2-Methyl-2-[[2-[(1-methylethyl)amino]-5-[(phenylmethyl)thio]thiazolo[4,5-d]pyrimidin-7-yl]amino]-1-propanol, 2-[[2-[[2-(4-Aminophenyl)ethyl]amino]-5-[(phenylmethyl)thio]thiazolo[4,5-d]pyrimidin-7-yl]amino]-2-methyl-1-propanol, N-[7-[(2-Hydroxy-1,1-dimethylethyl)amino]-5-[(phenylmethyl)thio]thiazolo[4,5-d]pyrimidin-2-yl]-L-valine, ethyl ester, (2S)-2-[[7-[(2-Hydroxy-1,1-dimethylethyl)amino]-5-[(phenylmethyl)thio]thiazolo[4,5-d]pyrimidin-2-yl]amino]-4-methyl-pentanamide, 2-Methyl-2-[[2-[(2-phenylethyl)amino]-5-[(phenylmethyl)thio]thiazolo[4,5-d]pyrimidin-7-yl]amino]-1-propanol, 2-[[2-[[(4-Aminophenyl)methyl]amino]-5-[(phenylmethyl)thio]thiazolo[4,5-d]pyrimidin-7-yl]amino]-2-methyl-1-propanol, 2-Methyl-2-[[5-[(phenylmethyl)thio]-2-[[2-(2-thienyl)ethyl]amino]thiazolo[4,5-d]pyrimidin-7-yl]amino]-1-propanol, 2-[[2-[(2-Fluoroethyl)amino]-5-[(phenylmethyl)thio]thiazolo[4,5-d]pyrimidin-7-yl]amino]-2-methyl-1-propanol, 2-Methyl-2-[[2-[[(3-nitrophenyl)methyl]amino]-5-[(phenylmethyl)thio]thiazolo[4,5-d]pyrimidin-7-yl]amino]-1-propanol, (αR)-α-[(1S)-1-[[7-[(2-Hydroxy-1,1-dimethylethyl)amino]-5-[(phenylmethyl)thio]thiazolo[4,5-d]pyrimidin-2-yl]amino]ethyl]-benzenemethanol, 2-Methyl-2-[[5-[(phenylmethyl)thio]-2-[[(3,4,5-trimethoxyphenyl)methyl]amino]thiazolo[4,5-d]pyrimidin-7-yl]amino]-1-propanol, 2-Methyl-2-[[2-[(1R-trans)-(2-phenylcyclopropyl)amino]-5-[(phenylmethyl)thio]thiazolo[4,5-d]pyrimidin-7-yl]amino]-1-propanol, 2-[[2-[[2-(1H-Indol-3-yl)ethyl]amino]-5-[(phenylmethyl)thio]thiazolo[4,5-d]pyrimidin-7-yl]amino]-2-methyl-1-propanol, 2-[[2-[(1,1-Dimethylpropyl)amino]-5-[(phenylmethyl)thio]thiazolo[4,5-d]pyrimidin-7-yl]amino]-2-methyl-1-propanol, (±)-2-Methyl-2-[[2-[(1-methylbutyl)amino]-5-[(phenylmethyl)thio]thiazolo[4,5-d]pyrimidin-7-yl]amino]-1-propanol, (±)-2-Methyl-2-[[2-[(1-methylhexyl)amino]-5-[(phenylmethyl)thio]thiazolo[4,5-d]pyrimidin-7-yl]amino]-1-propanol, 2-[[2-[[(2-Aminophenyl)methyl]amino]-5-[(phenylmethyl)thio]thiazolo[4,5-d]pyrimidin-7-yl]amino]-2-methyl-1-propanol, 2-[[7-[(2-Hydroxy-1,1-dimethylethyl)amino]-5-[(phenylmethyl)thio]thiazolo[4,5-d]pyrimidin-2-yl]amino]-1,3-propanediol, 2-[[2-[[2-(Ethylthio)ethyl]amino]-5-[(phenylmethyl)thio]thiazolo[4,5-d]pyrimidin-7-yl]amino]-2-methyl-1-propanol, (2S)-2-[[7-[(2-Hydroxy-1,1-dimethylethyl)amino]-5-[(phenylmethyl)thio]thiazolo[4,5-d]pyrimidin-2-yl]amino]-3,3-dimethyl-1-butanol, (αS)-α-[(1R)-1-[[7-[(2-Hydroxy-1,1-dimethylethyl)amino]-5-[(phenylmethyl)thio]thiazolo[4,5-d]pyrimidin-2-yl]amino]-2-methoxyethyl]-benzenemethanol, 2-[[2-(Ethylamino)-5-[(phenylmethyl)thio]thiazolo[4,5-d]pyrimidin-7-yl]amino]-2-methyl-1-propanol, 2-[[2-[[[3-Fluoro-5-(trifluoromethyl)phenyl]methyl]amino]-5-[(phenylmethyl)thio]thiazolo[4,5-d]pyrimidin-7-yl]amino]-2-methyl-1-propanol, (±)-2-Methyl-2-[[2-[(1-methylpropyl)amino]-5-[(phenylmethyl)thio]thiazolo[4,5-d]pyrimidin-7-yl]amino]-1-propanol, 2-[[2-[[(4-Methoxyphenyl)methyl]amino]-5-[(phenylmethyl)thio]thiazolo[4,5-d]pyrimidin-7-yl]amino]-2-methyl-1-propanol, 2-[[2-[(2-Hydroxyethyl)amino]-5-[(phenylmethyl)thio]thiazolo[4,5-d]pyrimidin-7-yl]amino]-2-methyl-1-propanol, 2-[[2-[[2-(1H-Imidazol-4-yl)ethyl]amino]-5-[(phenylmethyl)thio]thiazolo[4,5-d]pyrimidin-7-yl]amino]-2-methyl-1-propanol, 2-[[2-[(Diphenylmethyl)amino]-5-[(phenylmethyl)thio]thiazolo[4,5-d]pyrimidin-7-yl]amino]-2-methyl-1-propanol, (2S)-2-[[7-[(2-Hydroxy-1,1-dimethylethyl)amino]-5-[(phenylmethyl)thio]thiazolo[4,5-d]pyrimidin-2-yl]amino]-1-butanol, 2-[[2-[(2,2-Diethoxyethyl)amino]-5-[(phenylmethyl)thio]thiazolo[4,5-d]pyrimidin-7-yl]amino]-2-methyl-1-propanol, 4-[[7-[(2-Hydroxy-1,1-dimethylethyl)amino]-5-[(phenylmethyl)thio]thiazolo[4,5-d]pyrimidin-2-yl]amino]-1-butanol, (1S,2S)-2-[[7-[(2-Hydroxy-1,1-dimethylethyl)amino]-5-[(phenylmethyl)thio]thiazolo[4,5-d]pyrimidin-2-yl]amino]-cyclohexanol, (±)-2-[[2-[(2-Hydroxy-1-methylethyl)amino]-5-[(phenylmethyl)thio]thiazolo[4,5-d]pyrimidin-7-yl]amino]-2-methyl-1-propanol, 2-[[2-[[2-(2-Hydroxyethoxy)ethyl]amino]-5-[(phenylmethyl)thio]thiazolo[4,5-d]pyrimidin-7-yl]amino]-2-methyl-1-propanol, (±)-2-[[7-[(2-Hydroxy-1,1-dimethylethyl)amino]-5-[(phenylmethyl)thio]thiazolo[4,5-d]pyrimidin-2-yl]amino]-1-pentanol, 2-[[7-[(2-Hydroxy-1,1-dimethylethyl)amino]-5-[(phenylmethyl)thio]thiazolo[4,5-d]pyrimidin-2-yl]amino]-acetamide, (±)-2-[[2-[[1-(4-Fluorophenyl)ethyl]amino]-5-[(phenylmethyl)thio]thiazolo[4,5-d]pyrimidin-7-yl]amino]-2-methyl-propanol, (1R,2S)-2-[[7-[(2-Hydroxy-1,1-dimethylethyl)amino]-5-[(phenylmethyl)thio]thiazolo[4,5-d]pyrimidin-2-yl]amino]-cyclohexanol, (αS)-α-[(1R)-1-[[7-[(2-Hydroxy-1,1-dimethylethyl)amino]-5-[(phenylmethyl)thio]thiazolo[4,5-d]pyrimidin-2-yl]amino]ethyl]-benzenemethanol, (±)-2-[[2-(Methylamino)-5-[(phenylmethyl)thio]thiazolo[4,5-d]pyrimidin-7-yl]amino]-1-propanol, (2R)-4-Methyl-2-[[2-(methylamino)-5-[(phenylmethyl)thio]thiazolo[4,5-d]pyrimidin-7-yl]amino]-1-pentanol, N-[2-(Methylamino)-5-[(phenylmethyl)thio]thiazolo[4,5-d]pyrimidin-7-yl]-L-serine, ethyl ester, (±)-2-[[5-[(Phenylmethyl)thio]-2-[[(tetrahydro-2-furanyl)methyl]amino]thiazolo[4,5-d]pyrimidin-7-yl]amino]-1-butanol, (±)-2-[[5-[(Phenylmethyl)thio]-2-[[(tetrahydro-2-furanyl)methyl]amino]thiazolo[4,5-d]pyrimidin-7-yl]amino]-1-propanol, (2R)-4-Methyl-2-[[5-[(phenylmethyl)thio]-2-[[(tetrahydro-2-furanyl)methyl]amino]thiazolo[4,5-d]pyrimidin-7-yl]amino]-1-pentanol, N-[5-[(Phenylmethyl)thio]-2-[[(tetrahydro-2-furanyl)methyl]amino]thiazolo[4,5-d]pyrimidin-7-yl]-L-serine, ethyl ester, (±)-2-[[2-[[2-(2-Hydroxyethoxy)ethyl]amino]-5-[(phenylmethyl)thio]thiazolo[4,5-d]pyrimidin-7-yl]amino]-1-propanol, (±)-4-[2-[[7-[[1-(Hydroxymethyl)propyl]amino]-5-[(phenylmethyl)thio]thiazolo[4,5-d]pyrimidin-2-yl]amino]ethyl]-benzenesulfonamide, (±)-4-[2-[[7-[[(2-Hydroxy-1-methylethyl)amino]-5-[(phenylmethyl)thio]thiazolo[4,5-d]pyrimidin-2-yl]amino]ethyl]-benzenesulfonamide, 4-[2-[[7-[[(1R)-1-(Hydroxymethyl)-3-methylbutyl]amino]-5-[(phenylmethyl)thio]thiazolo[4,5-d]pyrimidin-2-yl]amino]ethyl]-benzenesulfonamide, (±)-4-[2-[[7-[(2-Hydroxypropyl)amino]-5-[(phenylmethyl)thio]thiazolo[4,5-d]pyrimidin-1-yl]amino]ethyl]-benzenesulfonamide, $N^7$-Ethyl-$N^2$-[2-(1H-imidazol-4-yl)ethyl]-5-[(phenylmethyl)thio]thiazolo[4,5-d]pyrimidine-2,7-diamine, $N^2$-[2-(1H-Imidazol-4-yl)ethyl]-5-[(phenylmethyl)thio]-$N^7$-(3-pyridinylmethyl)thiazolo[4,5-d]pyrimidine-2,7-diamine, (±)-2-[[2-[[2-(1H-Imidazol-4-yl)ethyl]amino]-5-[(phenylmethyl)thio]thiazolo[4,5-d]pyrimidin-7-yl]amino]-1-butanol, (±)-2-[[2-[(2-(1H-Imidazol-4-yl)ethyl]amino]-5-[(phenylmethyl)thio]thiazolo[4,5-d]pyrimidin-7-yl]amino]-1-propanol, (2R)-2-[[2-[[2-(1H-Imidazol-4-yl)ethyl]amino]-5-[(phenylmethyl)thio]thiazolo[4,5-d]pyrimidin-7-yl]amino]-4-methyl-1-pentanol, (±)-1-[[2-[[2-(1H-Imidazol-4-yl)ethyl]amino]-5-[(phenylmethyl)thio]thiazolo[4,5-d]pyrimidin-7-yl]amino]-2-propanol, 5-[[2-[[2-(1H-Imidazol-4-yl)ethyl]amino]-5-[(phenylmethyl)thio]thiazolo[4,5-d]pyrimidin-7-yl]amino]-1-pentanol, 1-[2-[[2-(1H-Imidazol-4-yl)ethyl]amino]-5-[(phenylmethyl)thio]thiazolo[4,5-d]pyrimidin-7-yl]-4-(phenylmethyl)-4-piperidinol, (±)-1-[2-[[2-(1H-Imidazol-4-yl)ethyl]amino]-5-[(phenylmethyl)thio]thiazolo[4,5-d]pyrimidin-7-yl]-3-piperidinecarboxamide, 2-[Ethyl[2-[[2-(1H-imidazol-4-yl)ethyl]amino]-5-[(phenylmethyl)thio]thiazolo[4,5-d]pyrimidin-7-yl]amino]-1-ethanol, $N^2$-[2-(1H-Imidazol-4-yl)ethyl]-$N^7$,$N^7$-dimethyl-5-[(phenylmethyl)thio]-thiazolo[4,5-d]pyrimidine-2,7-diamine, $N^7$-[2-(Diethylamino)ethyl]-$N^7$-ethyl-$N^2$-[2-(1H-imidazol-4-yl)ethyl]-5-[(phenylmethyl)thio]-thiazolo[4,5-d]pyrimidine-2,7-diamine, $N^2$-(2-Phenoxyethyl)-5-[(phenylmethyl)thio]-$N^7$-(3-pyridinylmethyl)thiazolo[4,5-d]pyrimidine-2,7-diamine, $N^2$-(2-Phenoxyethyl)-$N^7$-[1-(phenylmethyl)-4-piperidinyl]-5-[(phenylmethyl)thio]-thiazolo[4,5-d]pyrimidine-2,7-diamine, 2-Methyl-2-[[2-[(2-phenoxyethyl)amino]-5-[(phenylmethyl)thio]thiazolo[4,5-d]pyrimidin-7-yl]amino]-1-propanol, (±)-2-[[2-[(2-Phenoxyethyl)amino]-5-[(phenylmethyl)thio]thiazolo[4,5-d]pyrimidin-7-yl]amino]-1-propanol, (±)-4-Methyl-2-[[2-[(2-phenoxyethyl)amino]-5-[(phenylmethyl)thio]thiazolo[4,5-d]pyrimidin-7-yl]amino]-1-pentanol, 1-[2-[(2-Phenoxyethyl)amino]-5-[(phenylmethyl)thio]thiazolo[4,5-d]pyrimidin-7-yl]-4-(phenylmethyl)-4-piperidinol, 2-[[2-(Cyclopropylamino)-5-[(phenylmethyl)thio]thiazolo[4,5-d]pyrimidin-7-yl]amino]-1-butanol, 2-[[2-(Cyclopropylamino)-5-[(phenylmethyl)thio]thiazolo[4,5-d]pyrimidin-7-yl]amino]-1-propanol, (2R)-2-[[2-(Cyclopropylamino)-5-[(phenylmethyl)thio]thiazolo[4,5-d]pyrimidin-7-yl]amino]-4-methyl-1-pentanol, N-[2-(Cyclopropylamino)-5-[(phenylmethyl)thio]thiazolo[4,5-d]pyrimidin-7-yl]-L-serine, ethyl ester, (2R)-2-[[2-[[1-(Hydroxymethyl)butyl]amino]-5-[(phenylmethyl)thio]thiazolo[4,5-d]pyrimidin-7-yl]amino]-4-methyl-1-pentanol, N-[2-[[1-(Hydroxymethyl)butyl]amino]-5-[(phenylmethyl)thio]thiazolo[4,5-d]pyrimidin-7-yl-L-serine, ethyl ester, (±)-2-[[7-[Cyclohexyl(2-hydroxyethyl)amino]-5-[(phenylmethyl)thio]thiazolo[4,5-d]pyrimidin-2-yl]amino]-1-pentanol, 2-[2-[(7-(Ethylamino)-5-[(phenylmethyl)thio]thiazolo[4,5-d]pyrimidin-2-yl]amino]ethoxy-1-ethanol, 2-[2-[[7-[(1-Methylethyl)amino]-5-[(phenylmethyl)thio]thiazolo[4,5-d]pyrimidin-2-yl]amino]ethoxy]-1-ethanol, (±)-2-[[2-[[2-(2-Hydroxyethoxy)ethyl]amino]-5-[(phenylmethyl)thio]thiazolo[4,5-d]pyrimidin-7-yl]amino]-1-butanol, 2-[[2-[[2-(2-Hydroxyethoxy)ethyl]amino]-5-[(phenylmethyl)thio]thiazolo[4,5-d]pyrimidin-7-yl]amino]-2-methyl-1-propanol, (2R)-2-[[2-[[2-(2-Hydroxyethoxy)ethyl]amino]-5-[(phenylmethyl)thio]thiazolo[4,5-d]pyrimidin-7-yl]amino]-4-methyl-1-pentanol, 2-[Cyclohexyl-[2-[[2-(2-hydroxyethoxy)ethyl]amino]-5-[(phenylmethyl)thio]thiazolo[4,5-d]pyrimidin-7-yl]amino]-1-ethanol, (±)-2-[[5-[(Phenylmethyl)thio]-2-(4-piperidinylamino)thiazolo[4,5-d]pyrimidin-7-yl]amino]-1-propanol, (±)-N-[2-[[7-[[1-(Hydroxymethyl)propyl]amino]-5-[(phenylmethyl)thio]thiazolo[4,5-d]pyrimidin-2-yl]amino]ethyl]-acetamide, (±)-N-[2-[[7-[(2-Hydroxy-1-methylethyl)amino]-5-[(phenylmethyl)thio]thiazolo[4,5-d]pyrimidin-2-yl]amino]ethyl]-acetamide, N-(2-[[7-[(2-Hydroxyethyl)amino]-5-[(phenylmethyl)thio]thiazolo[4,5-d]pyrimidin-2-yl]amino]ethyl]-acetamide, N-[2-[[7-[[(1R)-1-(Hydroxymethyl)-3-methylbutyl]amino]-5-[(phenylmethyl)thio]thiazolo[4,5-d]pyrimidin-2-yl]amino]ethyl]-acetamide, $N^7$-(2-Methoxyethyl)-5-[(phenylmethyl)thio]-$N^2$-[2-(2-thienyl)ethyl]thiazolo[4,5-d]pyrimidine-2,7-diamine, $N^7$-(2-Ethoxyethyl)-5-[(phenylmethyl)thio]-$N^2$-[2-(2-thienyl)ethyl]thiazolo[4,5-d]pyrimidine-2,7-diamine, $N^7$-(2,2-Dimethylpropyl)-5-[(phenylmethyl)thio]-$N^2$-[2-(2-thienyl)ethyl]thiazolo[4,5-d]pyrimidine-2,7-diamine, (2R)-4-Methyl-2-[[-5-[(phenylmethyl)thio]-2-[[2-(2-thienyl)ethyl]amino]thiazolo[4,5-d]pyrimidin-7-yl]amino]-1-pentanol, (±)-1-[[5-[(Phenylmethyl)thio]-2-[[2-(2-thienyl)ethyl]amino]thiazolo[4,5-d]pyrimidin-7-yl]amino]-2-propanol, (±)-2-[[5-[(Phenylmethyl)thio]-2-[[2-(2-thienyl)ethyl]amino]thiazolo[4,5-d]pyrimidin-7-yl]amino]-1-butanol, (±)-2-[[5-[(Phenylmethyl)thio]-2-[[2-(2-thienyl)ethyl]amino]thiazolo[4,5-d]pyrimidin-7-yl]amino]-1-propanol, (2R)-2-[[2-[(2-Hydroxyethyl)amino]-5-[(phenylmethyl)thio]thiazolo[4,5-d]pyrimidin-7-yl]amino]-4-methyl-1-pentanol, (±)-N,N-Diethyl-1-[2-[(2-hydroxyethyl)amino]-5-[(phenylmethyl)thio]thiazolo[4,5-d]pyrimidin-7-yl]-3-piperidinecarboxamide, (2R)-2-[[2-[(3-Hydroxypropyl)amino]-5-[(phenylmethyl)thio]thiazolo[4,5-d]pyrimidin-7-yl]amino]-4-methyl-1-pentanol, (±)-2-[[2-[(3-Hydroxypropyl)amino]-5-[(phenylmethyl)thio]thiazolo[4,5-d]pyrimidin-7-yl]amino]-1-butanol, (±)-2-[[2-[(3-Hydroxypropyl)amino]-5-[(phenylmethyl)thio]thiazolo[4,5-d]pyrimidin-7-yl]amino]-1-propanol, 2-[(7-[(2-Hydroxy-1-methylethyl)amino]-5-[(phenylmethyl)thio]thiazolo[4,5-d]pyrimidin-2-yl]amino-acetamide, 4-[1-[7-[(4-Methylcyclohexyl)amino]-5-[(phenylmethyl)thio]thiazolo[4,5-d]pyrimidin-2-yl]-3-azetidinyl]-1-piperazinesulfonamide, 3-[[2-[[2-(4-Morpholinyl)ethyl]amino]-5-[(phenylmethyl)thio]thiazolo[4,5-d]pyrimidin-7-yl]amino]-1-propanol, 2-Methyl-2-[[2-[[2-(4-morpholinyl)ethyl]amino]-5-[(phenylmethyl)thio]thiazolo[4,5-d]pyrimidin-7-yl]amino]-1-propanol, (±)-2-[[2-[[2-(4-Morpholinyl)ethyl]amino]-5-[(phenylmethyl)thio]thiazolo[4,5-d]pyrimidin-7-yl]amino]-1-propanol, (2R)-4-Methyl-2-[[2-[[2-(4-morpholinyl)ethyl]amino]-5-[(phenylmethyl)thio]thiazolo[4,5-d]pyrimidin-7-yl]amino]-1-pentanol, 2-[[2-(3,4-Dihydroxyphenyl)ethyl]amino]-5-[(phenylmethyl)thio]-thiazolo[4,5-d]pyrimidin-7(4H)-one, (±)-2-[(2-Hydroxy-1-methylethyl)amino]-5-[(phenylmethyl)thio]-thiazolo[4,5-d]pyrimidin-7(4H)-one, and their pharmaceutically acceptable salts and solvates.

According to the invention there is also provided a process for the preparation of a compound of formula (I) which comprises:

(a) when X represents —OH and $R^1$ is $NH_2$, heating a compound of general formula

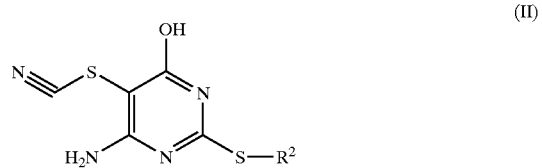

(II)

wherein $R^2$ is as defined in formula (I); or (b) when X represents —OH and $R^1$ is $NH_2$, reacting a compound of formula

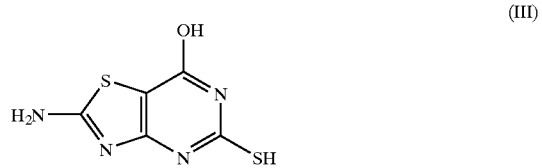

(III)

with a compound of general formula (IV), $R^2$—$L^1$, wherein $L^1$ represents a leaving group such as a halogen atom (e.g. chlorine) and $R^2$ is as defined in formula (I); or (c) when X represents —OH or —$NR^{13}R^{14}$ and $R^1$ is a hydrogen atom, reacting a corresponding compound of formula (I) in which $R^1$ is $NH_2$, with a diazotizing agent; or (d) when X represents —OH and R$^1$ is a group —NR$^3$R$^4$ reacting a compound of general formula

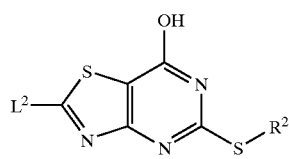
(V)

wherein L$^2$ represents a leaving group such as a halogen atom (e.g. bromine) and R$^2$ is as defined in formula (I), with a compound of general formula (VI), R$^3$R$^4$NH, wherein R$^3$ and R$^4$ are as defined in formula (I); or (e) when X represents —NR$^{13}$R$^{14}$ and R$^1$ represents —NR$^3$R$^4$, reacting a compound of general formula

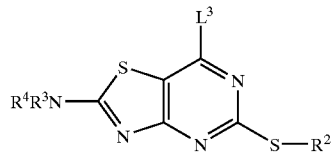
(VII)

wherein L$^3$ represents a leaving group such as a halogen atom (e.g. chlorine) and R$^2$, R$^3$ and R$^4$ are as defined in formula (X), with a compound of general formula (VIII), NHR$^{13}$R$^{14}$, wherein R$^{13}$ and R$^{14}$ are as defined in formula (I); or (f) when X represents —NR$^{13}$R$^{14}$ and R$^1$ represents —NR$^3$R$^4$, reacting a compound of general formula

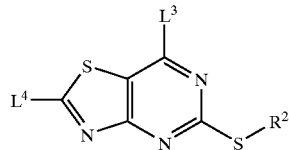
(IX)

wherein L$^4$ is a leaving group (e.g. bromine), L$^5$ is a leaving group (e.g. chlorine) and R$^2$ is as defined in formula (I), initially with a compound of formula (VI) as defined in (d) above followed by reaction with a compound of formula (VIII) as defined in (e) above; and optionally after (a), (b), (c), (d), (e) or (f) forming a pharmaceutically acceptable salt or solvate of the compound of formula (I).

Process (a) is conveniently carried out in the presence of a solvent or solvent mixture such as dimethylformamide/water at a temperature in the range from e.g. 50 to 150° C.

Process (b) is conveniently carried out in an organic solvent such as tetrahydrofuran or dimethyl sulphoxide/dimethylformide mixture, optionally in the presence of a base such as potassium tert-butoxide or duisopropylamide.

Process (c) is conveniently carried out in an organic solvent such as tetrahydrofuran. Examples of suitable diazotizing agents to use include tert-butyl nitrite.

Process (d) is conveniently carried out in an organic solvent such as tetrahydrofuran, e.g. at a temperature of 50° C. for 5 hours.

Process (e) is conveniently carried out in an organic solvent such as tetrahydrofuran with heating for a period in the range from 1 day to 3 weeks.

Process (f) is conveniently carried out in an organic solvent such as tetrahydrofuran or N-methylpyrrolidine at a temperature between 0° and 130° C. with a reaction time of 1 hour to 3 weeks.

Compounds of formula (II) may be readily prepared by reacting a compound of general formula

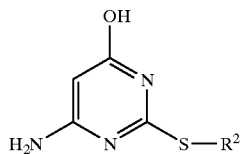
(X)

wherein R$^2$ is as defined above, with potassium thiocyanate and bromine in dimethylformamide/pyridine.

Compounds of formula (X) are suitably prepared by reacting a compound of formula

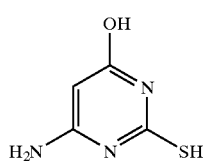
(XI)

with a compound of formula (IV) as defined above.

Compounds of formula (V) may be prepared by reacting a compound of formula (I) in which R$^1$ is NH$_2$, with a diazotizing agent and a halogenating agent. The reaction is conveniently carried out in an organic solvent such as acetonitrile in the presence of a diazotizing agent such as tert-butyl nitrite and a halogenating agent such as a trimethylsilyl halide.

Compounds of formula (VII) in which L$^3$ is a chlorine atom may be prepared by reacting a compound of formula (I) in which X is —OH with phosphorus oxychloride in dimethylaniline under reflux conditions.

Compounds of formula (IX) in which L$^4$ represents a bromine atom and L$^5$ represents a chlorine atom may be prepared by reacting a compound of formula (I) in which X is —OH and R$^1$ is NH$_2$ with phosphorus oxychloride in dimethylaniline under reflux conditions, followed by reaction with tert-butyl nitrite and bromoform.

Compounds of formulae (III), (IV), (VI), (VIII) and (XI) are either commercially available, are well known in the literature or may be prepared easily using known techniques.

The compounds of formulae (V), (VII) and (IX) are novel intermediates and therefore form a further aspect of the present invention. In formula (V), L$^2$ is preferably a bromine atom. In formula (VII), R$^3$ and R$^4$ preferably both represent a hydrogen atom. In formula (IX), L$^3$ is preferably a bromine atom and L$^4$ is preferably a chlorine atom.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

The compounds of formula (I) above may be converted to a phamaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention, for example tautomers of general formula

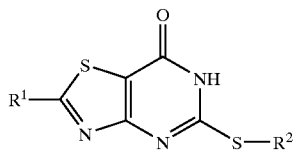

(I')

wherein R¹ and R² are as defined in formula (I), or of general formula

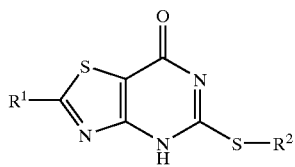

(I'')

wherein R¹ and R² are as defined in formula (I).

Similarly, it will be understood that in the above processes tautomeric forms of the compounds of formulae (II), (III), (IX) and (X) may also be used, for example,

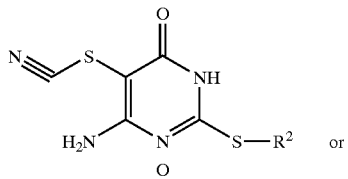 or

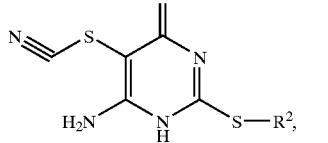

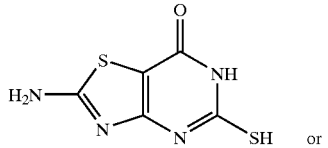 or

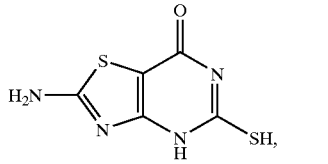

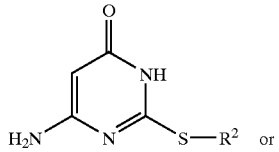 or

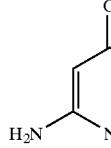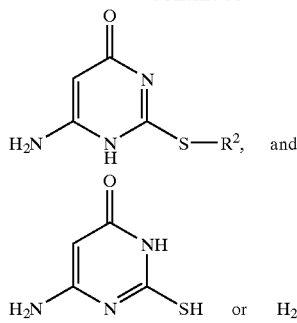

The compounds of formula (I) have activity as pharmaceuticals, in particular as modulators of chemokine receptor (especially CXCR2) activity, and may be used in the treatment (therapeutic or prophylactic) of conditions/diseases in human and non-human animals which are exacerbated or caused by excessive or unregulated production of chemokines.

Examples of such conditions/diseases include:
(1) (the respiratory tract) obstructive airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis cascosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;
(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;
(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodernas, vasculitides, erythemas, cutaneous eosinophilias, uveitis, Alopecia areata and vernal conjunctivitis;
(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;
(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;
(6) (allograft rejection) acute and chronic following, for example, transplantation of kidney, heart, liver, lung, bone marrow, skin and cornea; and chronic graft versus host disease;
(7) cancers, especially non-small cell lung cancer (NSCLC) and squamous sarcoma;
(8) diseases in which angiogenesis is associated with raised CXCR2 chemokine levels (e.g. NSCLC); and
(9) cystic fibrosis, stroke, re-perfusion injury in the heart, brain, peripheral limbs and sepsis.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a CXCR2 receptor, which comprises administering to a patient a therapeutically effective amount of a compound of formula (I), or a pharmaceutically acceptable salt or solvate thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The inventon will now be further illustrated by reference to the following examples. In the examples the Nuclear Magnetic Resonance (NMR) spectra were measured on a Varian Unity Inova 300 or 400 MHz spectrometer and the Mass Spectrometry (MS) spectra measured on a Finnigan Mat SSQ7000 or Micromass Platform spectrometer. Where necessary, the reactions were performed under an inert atmosphere of either nitrogen or argon. Chromatography was generally performed using Matrex Silica 60® (35–70 micron) or Prolabo Silica gel 60® (35–70 micron) suitable for flash silica gel chromatography. High pressure liquid chromatography purification was performed using either a Waters Micromass LCZ with a Waters 600 pump controller, Waters 2487 detector and Gilson FC024 fraction collector or a Waters Delta Prep 4000. The abbreviations m.p. and DMSO used in the examples stand for melting point and dimethyl sulphoxide respectively.

EXAMPLE 1

(2R)-2-[[2-Amino-5-[(phenylmethyl)thio]thiazolo[4,5-d]pyrimidin-7-yl]amino]-1-butanol

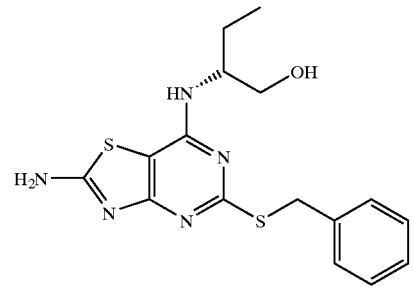

(a) 7-Chloro-5-[(phenylmethyl)thio]thiazolo[4,5-d]pyrimidin-2-amine

2-Amino-5-[(phenylmethyl)thio]thiazolo[4,5-d]pyrimidin-7(4H)-one (0.89 g) (prepared as described in Example 9), phosphorus oxychloride (12 mL) and N,N-dimethylaniline (1.2 mL) were heated at reflux for 2 hours. The cooled reaction mixture was poured onto ice and water and stirred for 2 hours. Chromatography on silica eluting with methanol/dichloromethane mixtures gave the sub-title chloride.

m.p. 217–218.5° C.

MS: APCI (+ve) 309/11 (M+1).

$^1$H NMR: δ (DMSO) 4.38 (s, 2H), 7.20–7.48 (m, 5H) and 8.95 (br s, 2H).

(b) (2R)-2-[[2-Amino-5-[(phenylmethyl)thio]thiazolo[4,5-d]pyrimidin-7-yl]amino]-1-butanol The chloro compound from step (a) (0.12 g) in tetrahydrofuran (3 mL) was treated with (R)-2-amino-1-butanol (0.56 g) and the reaction mixture was heated at reflux for 5 days. Dichloromethane and dilute hydrochloric acid were added. The resulting solid was filtered off, washed with water and ether to give the title compound which was obtained containing 0.23 moles of hydrogen chloride and 0.93 moles of water. Yield 0.045 g.

m.p. 118–121° C.

MS: APCI (+ve) 362 (M+1).

$^1$H NMR: δ (DMSO) 0.83 (t, 3H), 1.45 (m, 2H), 1.65 (m, 2H), 3.39 (m, 2H), 4.31 (q, 2H), 4.65 (t, 1H), 6.91 (d, 1H), 7.17–7.44 (m, 5H) and 8.00 (s, 2H).

EXAMPLE 2

(S)-2-[[2-Amino-5-[(phenylmethyl)thio]thiazolo[4,5-d]pyrimidin-7-yl]amino]-1-butanol

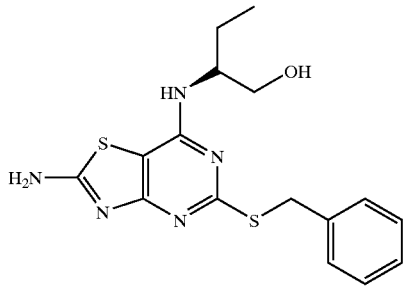

Prepared by the method of Example 1(b) from the chloro compound of Example 1(a) and (S)-2-amino-1-butanol. Obtained as a solid containing 0.7 moles of hydrogen chloride.

mp 204–208° C.

MS: APCI (+ve) 362 (M+1).

$^1$H NMR: δ (DMSO) 0.82 (t, 3H), 1.37–1.74 (m, 2H), 3.36–3.52 (m, 2H), 4.10 (br s, 1H), 4.41 (q, 2H), 7.20–7.46 (m, 5H), 7.63 (br s, 1H) and 8.42 (s, 2H).

EXAMPLE 3

2-Amino-5-[[(2,3-difluorophenyl)methyl]thio]thiazolo[4,5-d]pyrimidin-7(4H)-one

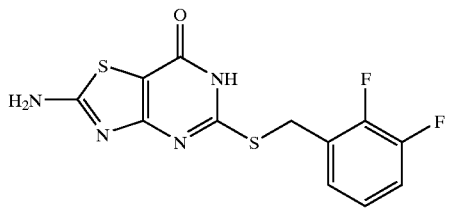

a) 2-Amino-5-mercapto-thiazolo[4,5-d]pyrimidin-7(4H)-one

Aluminum tribromide (1M in CH$_2$Br$_2$, 15.2 ml) was added to a solution of the product of Example 9 (2.0 g) in toluene (25 ml) and the reaction mixture heated at 60° C. for 6 hours. On cooling to room temperature, water (40 ml) was added and the resulting solid isolated by filtration then triturated with hot ethanol to afford the sub-title compound (0.9 g).

MS: (APCI) 201 (M+H$^+$, 100%).

b) 2-Amino-5-[[(2,3-difluorophenyl)methyl]thio]thiazolo[4,5-d]pyrimidin-7(4H)-one Potassium t-butoxide solution (0.45 mL of 1M in tetrahydrofuran) was added to a stirred solution of the product of step a) (0.09 g) and 2,3-difluorobenzyl bromide in dimethyl sulphoxide (2 mL). After stirring for 3 days, the reaction mixture was poured onto water. The title compound was obtained. Yield 0.065 g.

m.p. 310–313° C.

MS: APCI (+ve) 327 (M+1).

$^1$H NMR: δ (DMSO) 4.48 (s, 2H), 7.18–7.45 (m, 3H), 8.20 (s, 2H) and 12.62 (s, 1H).

EXAMPLE 4

5-[[(3-Phenoxyphenyl)methyl]thio]thiazolo[4,5-d]pyrimidin-7(4H)-one

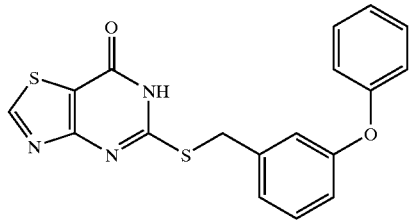

2-Amino-5-[[(3-phenoxyphenyl)methyl]thio]thiazolo[4,5-d]pyrimidin-7(4H)-one (0.3 g) (product of Example 5) was added over 90 minutes to a solution of t-butyl nitrite (0.17 mL) in tetrahydrofuran (3 mL) at 65° C. After a further 3.5 hours at 65° C., the solvent was evaporated and the residue chromatographed on silica eluting with methanol/dichloromethane mixtures to give the title compound. Yield 0.071 g.

m.p. 197–198° C.

MS: APCI (+ve) 368 (M+1).

$^1$H NMR: δ (DMSO) 4.49 (s, 2H), 6.86–7.38 (m, 9H), 9.58 (s, 1H) and 13.11 (s, 1H).

EXAMPLE 5

2-Amino-5-[[(3-phenoxyphenyl)methyl]thio]thiazolo[4,5-d]pyrimidin-7(4H)-one

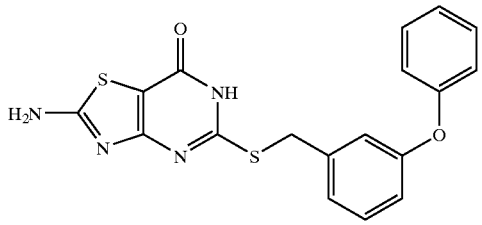

Prepared by the method of Example 3 using 3-phenoxybenzyl chloride.

m.p. 266–269° C.

MS: APCI (+ve) 383 (M+1).

$^1$H NMR: δ (DMSO) 4.40 (s, 2H), 6.81–7.41 (m, 9H), 8.15 (s, 2H) and 12.55 (s, 1H).

EXAMPLE 6

(±)-2-[[2-Amino-5-(pentylthio)thiazolo[4,5-d]pyrimidin-7-yl]amino]-1-butanol

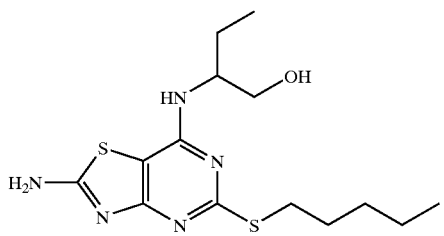

(a) 7-Chloro-5-(pentylthio)thiazolo[4,5-d]pyrimidin-2-amine

Prepared by the method of Example 1(a) from 2-amino-5-(pentylthio)thiazolo[4,5-d]pyrimidin-7(4H)-one (product of Example 10).

m.p. 176.5–177.5° C.

MS: APCI (+ve) 289 (M+1).

$^1$H NMR: δ (DMSO) 0.88 (t, 3H), 1.22–1.42 (m, 4H), 1.60–1.74 (m, 2H), 3.08 (t, 2H) and 8.90 (s, 2H).

(b) (±)-2-[[2-Amino-5-(pentylthio)thiazolo[4,5-d]pyrimidin-7-yl]amino]-1-buanol

Prepared by the method of Example 1(b) from the chloro compound of Example 6(a) and the appropnate amine.

m.p. 151–154° C.

MS: APCI (+ve) 342 (M+1).

$^1$H NMR: δ (DMSO) 0.82–0.95 (m, 6H), 1.22–1.72 (m, 8H), 3.04 (m, 2H), 3.39–3.56 (m, 2H), 4.07 (m, 1H), 4.64 (t, 1H), 6 88 (d, 1H), 7.44 (br s, 1H) and 7.96 (s, 2H).

EXAMPLE 7

2-[[2-Amino-5-(pentylthio)thiazolo[4,5-d]pyrimidin-7-yl]amino]ethanol

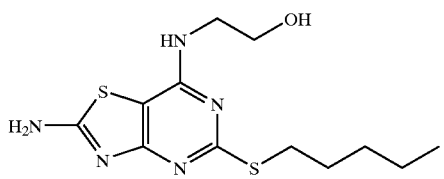

Prepared by the method of Example 6(b).

m.p. 192–195° C.

MS: APCI (+ve) 314 (M+1).

$^1$H NMR: δ (DMSO) 0.87 (t, 3H), 1.21–1.42 (m, 4H), 1.57–1.70 (m, 2H), 2.99 (t, 2H), 3.37–3.46 (m, 2H), 3.46–3.58 (m, 2H), 4.71 (t, 1H), 7.22 (t, 1H) and 7.97 (s, 2H).

EXAMPLE 8

5-(Pentylthio)thiazolo[4,5-d]pyrimidin-7(4H)-one

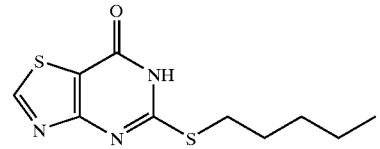

Prepared by the method of Example 4.

m.p. 208–209° C.

MS: APCI (+ve) 256 (M+1).

$^1$H NMR: δ (DMSO) 0.88 (t, 3H), 1.22–1.44 (m, 4H), 1.63–1.75 (m, 2H), 3.20 (t, 2H), 9.57 (s, 1H) and 13.06 (s, 1H).

EXAMPLE 9

2-Amino-5-[(phenylmethyl)thio]thiazolo[4,5-d]pyrimidin-7(4H)-one

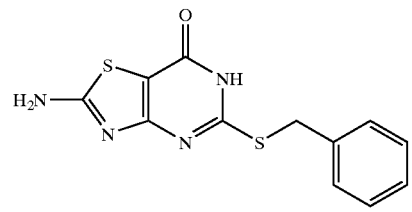

(a) 6-Amino-2-[(phenylmethyl)thio]-5-thiocyanato-4-(1H)-pyrimidinone

6-Amino-2-[(phenylmethyl)thio]-4-(1H)-pyrimidinone (10.5 g) (prepared as described in WO 96/35678) and potassium thiocyanate (25 g) in dimethylformamide (200 mL) were heated together at 65° C. Pyridine (6.3 mL) was added and the solution cooled to 5° C. Bromine (2.2 mL) was added slowly and the reaction mixture stirred for 2 hours at 5–10° C. The reaction mixture was poured onto ice and water, stirred for 1 hour and the solid was filtered off. After washing with water and ether a pure sample was obtained after tituration with hot methanol.

m.p. 260–262° C.

MS: APCI (+ve) 291 (M+1).

$^1$H NMR: δ (DMSO) 4.38 (s, 2H), 7.21–7.51 (m, 5H), 7.70 (br s, 2H) and 12.35 (s, 1H).

(b) 2-Amino-5-[(phenylmethyl)thio]thiazolo[4,5-d]pyrimidin-7(4H)-one

The product of step (a) (7.35 g) was heated at 120° C. in dimethylformamide (40 mL) and water (10 mL) for 10 hours. After cooling, the resulting solid was filtered off, washed with water, ether and ethyl acetate to give the title compound containing 0.4 moles of dimethylformamide.

m.p. ~325°.

MS: APCI (+ve) 291 (M+1).

$^1$H NMR: δ (DMSO) 4.41 (s, 2H), 7.21–7.50 (m, 5H), 8.17 (s, 2H) and 12.53 (br s, 1H).

EXAMPLE 10

2-Amino-5-(pentylthio)thiazolo[4,5-d]pyrimidin-7(4H)-one

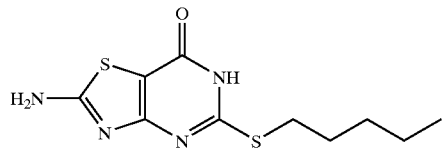

(a) 6-Amino-2-(pentylthio)-5-thiocyanato-4-(1H)-pyrimidinone

Prepared by the method of Example 9(a).

m.p. 260–262° C.

MS: APCI (+ve) 214 (M+1).

$^1$H NMR: δ (DMSO) 0.86 (t, 3H), 1.22–1.40 (m, 4H), 1.56–1.68 (m, 2H), 3.10 (t, 2H), 7.58 (br s, 2H) and 12.30 (s, 1H).

(b) 2-Amino-5-(pentylthio)thiazolo[4,5-d]pyrimidin-7(4H)-one

Prepared by the method of Example 9(b).

MS: APCI (+ve) 271 (M+1).

$^1$H NMR: δ (DMSO) 0.86 (t, 3H), 1.24–1.40 (m, 4H), 1.58–1.70 (m, 2H), 3.12 (t, 2H), 8.12 (br s, 2H) and 12.49 (s, 1H).

EXAMPLE 11

2-Bromo-5-(pentylthio)thiazolo[4,5-d]pyrimidin-7(4H)-one

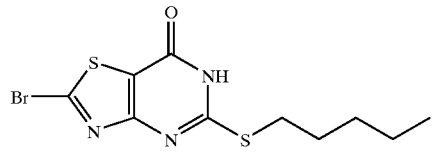

Trimethylsilyl bromide (0.44 mL) was added slowly to a solution at 0° C. under nitrogen of us t-butyl nitrite (0.42 mL) in acetonitrile (2 mL). After 30 minute at 0° C., 2-amino-5-(pentylthio)thiazolo[4,5-d]pyrimidin-7(4H)-one (0.5 g) (product of Example 10) was added.

The reaction mixture was stirred at room temperature for 16 hours and the solvent was evaporated. Chromatography on silica eluting with dichloromethane/methanol mixtures gave the title bromide.

m.p. 189–191° C.

MS: APCI (+ve) 336/7 (M+1).

$^1$H NMR: δ (DMSO) 0.88 (t, 3H), 1.261.41 (m, 4H), 1.64–1.75 (m, 2H), 3.18 (t, 2H) and 13.22 (s, 1H).

EXAMPLES 12–26

The compounds of Examples 12 to 26 were prepared by heating 2-bromo-5-(pentylthio)thiazolo[4,5-d]pyrimidin-7(4H)-one (product of Example 11) with 5 equivalents of the appropriate amine in tetrahydrofuran at 45° C. for 5 hours.

EXAMPLES 12

2-[[3-(Dimethylamino)propyl]amino]-5-(pentylthio)thiazolo[4,5-d]pyrimidin-7(4H)-one

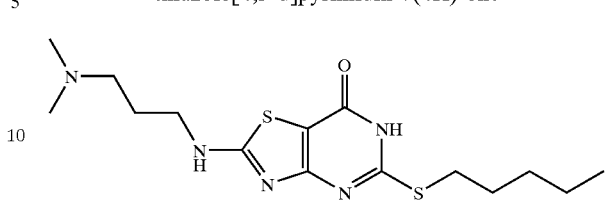

MS: APCI (+ve) 356 (M+1).

EXAMPLE 13

2-[[2-(Diethylamino)ethyl]amino]-5-(pentylthio)thiazolo[4,5-d]pyrimidin-7(4H)-one

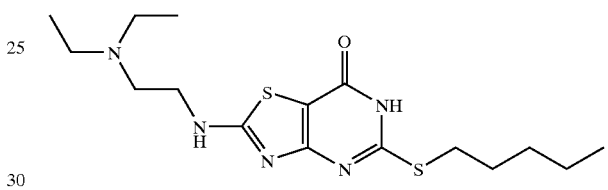

MS: APCI (+ve) 370 (M+1).

EXAMPLE 14

2-[[2-(Dimethylamino)ethyl]amino]-5-(pentylthio)thiazolo[4,5-d]pyrimidin-7(4H)-one

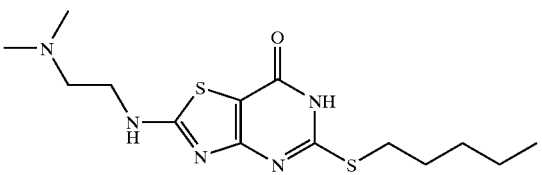

MS: APCI (+ve) 342 (M+1).

EXAMPLE 15

2-[(3-Hydroxypropyl)amino]-5-(pentylthio)thiazolo[4,5-d]pyrimidin-7(4H)-one

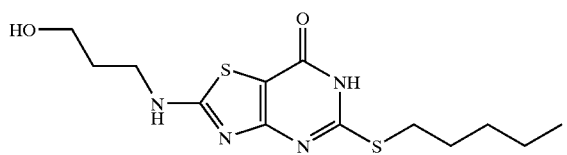

MS: APCI (+ve) 329 (M+1).

EXAMPLE 16

2-[[2-(Acetylamino)ethyl]amino]-5-(pentylthio)thiazolo[4,5-d]pyrimidin-7(4H)-one

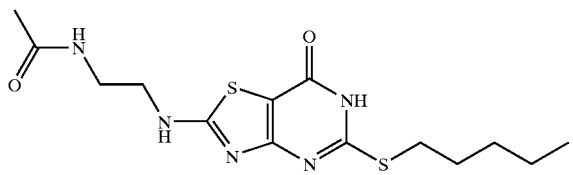

MS: APCI (+ve) 356 (M+1).

EXAMPLE 17

(±)-2-[(2,3-Dihydoxypropyl)amino]-5-(pentylthio)thiazolo[4,5-d]pyrimidin-7(4H)-one

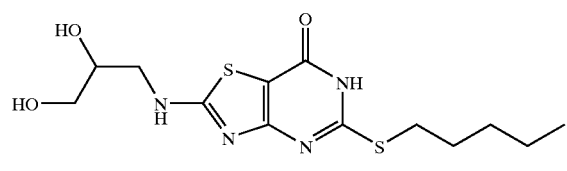

MS: APCI (+ve) 345 (M+1).

EXAMPLE 18

2-[[2-(4-Morpholinyl)ethyl]amino]-5-(pentylthio)thiazolo[4,5-d]pyrimidin-7(4H)-one

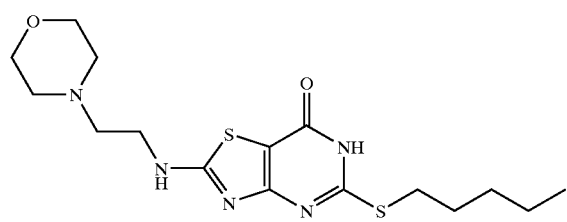

MS: APCI (+ve) 384 (M+1).

EXAMPLE 19

2-[(2-Methoxyethyl)amino]-5-(pentylthio)thiazolo[4,5-d]pyrimidin-7(4H)-one

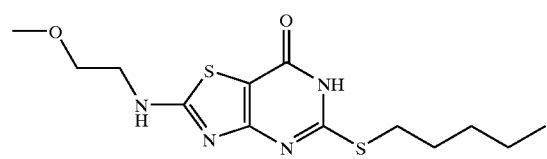

MS: APCI (+ve) 329 (M+1).

EXAMPLE 20

2-[(1-Methylethyl)amino]-5-(pentylthio)thiazolo[4,5-d]pyrimidin-7(4H)-one

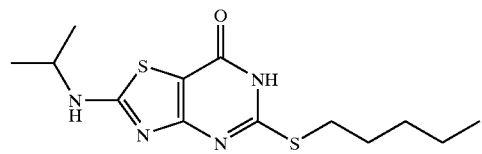

MS: APCI (+ve) 313 (M+1).

EXAMPLE 21

2-(Cyclopropylamino)-5-(pentylthio)thiazolo[4,5-d]pyrimidin-7(4H)-one

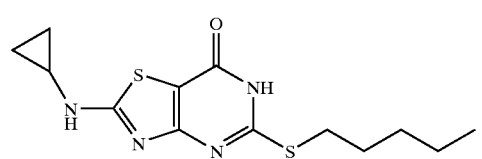

MS: APCI (+ve) 311 (M+1).

EXAMPLE 22

(±)-2-[(2-Hydoxypropyl)amino]-5-(pentylthio)thiazolo[4,5-d]pyrimidin-7(4H)-one

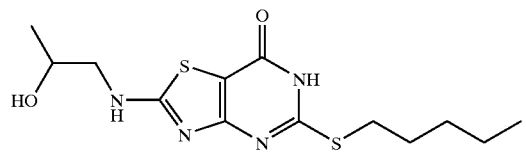

MS: APCI (+ve) 329 (M+1).

EXAMPLE 23

2-[[2-(2-Hydroxyethoxy)ethyl]amino]-5-(pentylthio)thiazolo[4,5-d]pyrimidin-7(4H)-one

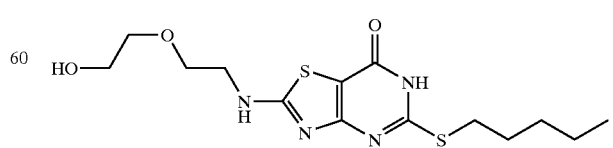

MS: APCI (+ve) 359 (M+1).

EXAMPLE 24

2-[(2-Hydroxy-2-methylpropyl)amino]-5-(pentylthio)thiazolo[4,5-d]pyrimidin-7(4H)-one

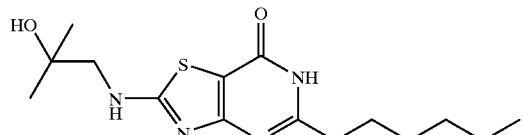

MS: APCI (+ve) 343 (M+1).

EXAMPLE 25

2-[(2-Hydroxyethyl)amino]-5-(pentylthio)thiazolo[4,5-d]pyrimidin-7(4H)-one

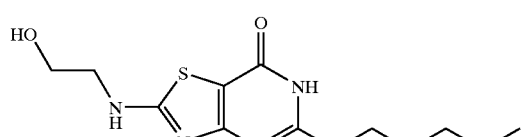

MS: APCI (+ve) 3 15 (M+1).

EXAMPLE 26

(2S,3R)-Hydroxy-2-[(7-oxo-5-pentylthio)-4H-thiazolo[4,5-d]pyrimidin-2-yl]amino)butanamide

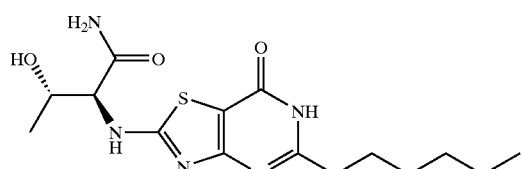

MS: APCI (+ve) 372 (M+1).

EXAMPLES 27–43

The compounds of Examples 27 to 43 were prepared by heating 7-chloro-5-(pentylthio)thiazolo[4,5-d]pyrimidin-2-amine (product of Example 6, step a) with 5 equivalents of the appropriate amine in tetrahydrofuran at 45° C. for 5 hours.

EXAMPLE 27

$N^7$-[3-(Dimethylamino)propyl]-5-(pentylthio)thiazolo[4,5-d]pyrimidine-2,7-diamine

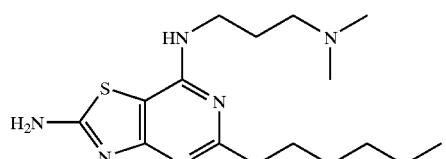

MS: APCI (+ve) 355 (M+1).

EXAMPLE 28

$N^7$-[2-(Diethylamino)ethyl]-5-(pentylthio)thiazolo[4,5-d]pyrimidine-2,7-diamine

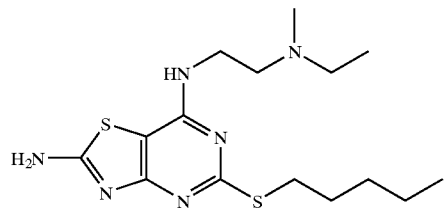

MS: APCI (+ve) 369 (M+1).

EXAMPLE 29

$N^7$-[2-(Dimethylamino)ethyl]-5-(pentylthio)thiazolo[4,5-d]pyrimidine-2,7-diamine

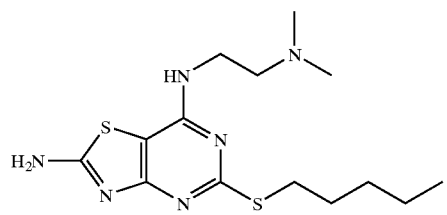

MS: APCI (+ve) 341 (M+1).

EXAMPLE 30

3-[(2-Amino-5-(pentylthio)thiazolo[4,5-d]pyrimidin-7-yl)amino]-1-propanol

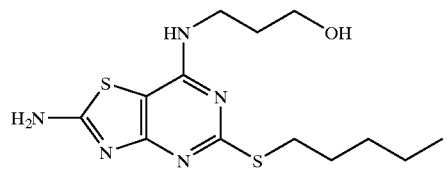

MS: APCI (+ve) 328 (M+1).

EXAMPLE 31

$N^7$-Cyclohexyl-5-(pentylthio)thiazolo[4,5-d]pyrimidine-2,7-diamine

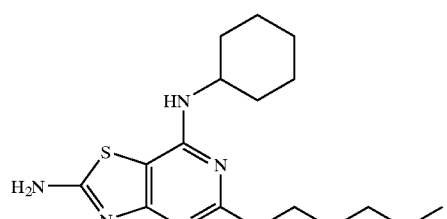

MS: APCI (+ve) 352 (M+1).

EXAMPLE 32

(±)-3-[(2-Amino-5-((phenylmethyl)thio)thiazolo[4,5-d]pyrimidin-7-yl)amino]-1,2-propanediol

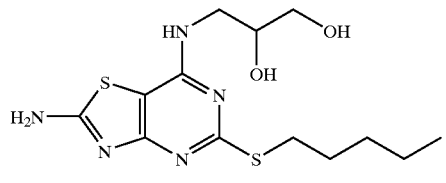

MS: APCI (+ve) 344 (M+1).

EXAMPLE 33

N$^7$-(2-Methoxyethyl)-5-(pentylthio)thiazolo[4,5-d]pyrimidine-2,7-diamine

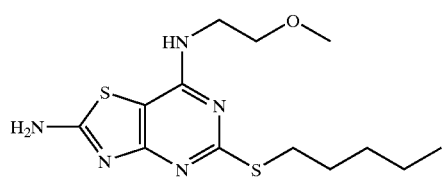

MS: APCI (+ve) 328 (M+1).

EXAMPLE 34

5-(Pentylthio)-N$^7$-propylthiazolo[4,5-d]pyrimidine-2,7-diamine

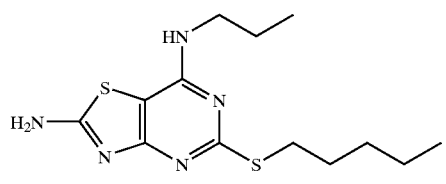

MS: APCI (+ve) 312 (M+1).

EXAMPLE 35

N$^7$-Cyclopentyl-5-(pentylthio)thiazolo[4,5-d]pyrimidine-2,7-diamine

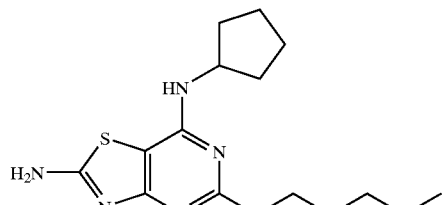

MS: APCI (+ve) 338 (M+1).

EXAMPLE 36

N$^7$-Cyclopropyl-5-(pentylthio)thiazolo[4,5-d]pyrimidine-2,7-diamine

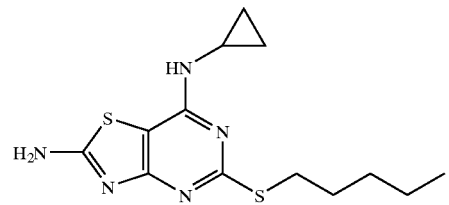

MS: APCI (+ve) 310 (M+1).

EXAMPLE 37

N$^7$-(2-Methylpropyl)-5-(pentylthio)thiazolo[4,5-d]pyrimidine-2,7-diamine

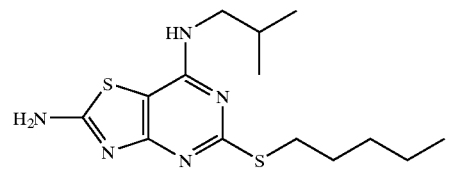

MS: APCI (+ve) 326 (M+1).

EXAMPLE 38

(±)-1-[2-Amino-5-(pentylthio)thiazolo[4,5-d]pyrimidin-7-yl)amino]-2-propanol

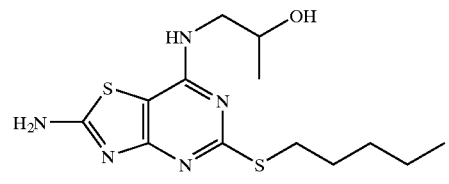

MS: APCI (+ve) 328 (M+1).

EXAMPLE 39

(exo)-N$^7$-Bicyclo[2.2.1]hept-2-yl-5-(pentylthio)thiazolo[4,5-d]pyrimidine-2,7-diamine

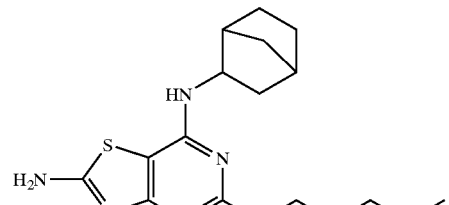

MS: APCI (+ve) 364 (M+1).

EXAMPLE 40

2-[2-[[2-Amino-5-(pentylthio)thiazolo[4,5-d]pyrimidin-7-yl]amino]ethoxy]ethanol

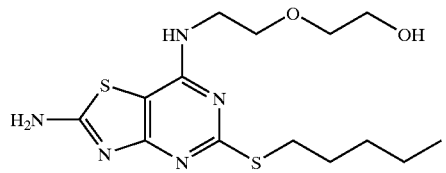

MS: APCI (+ve) 358 (M+1).

EXAMPLE 41

(±)-N⁷-(2-Methylbutyl)-5-(pentylthio)thiazolo[4,5-d]pyrimidine-2,7-diamine

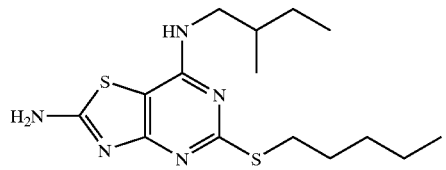

MS: APCI (+ve) 340 (M+1).

EXAMPLE 42

1-[[2-Amino-5-(pentylthio)thiazolo[4,5-d]pyrimidin-7-yl]amino]-2-methyl-2-propanol

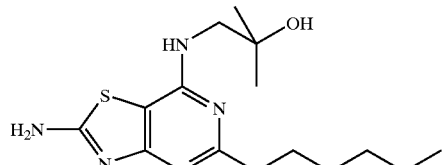

MS: APCI (+ve) 342 (M+1).

EXAMPLE 43

N⁷-[(2-Aminophenyl)methyl]-5-(pentylthio)thiazolo[4,5-d]pyrimidine-2,7-diamine

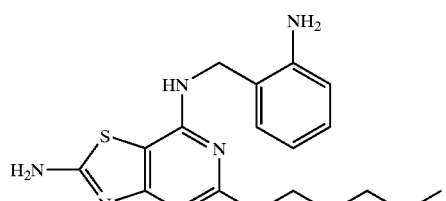

MS: APCI (+ve) 375 (M+1).

EXAMPLES 44–47

The compounds of Examples 44 to 47 were prepared from 2-amino-5,6-dihydro-5-thioxothiazolo[4,5-d]pyrimidin-7(4H)-one, diisopropylethylamine and the appropriate alkyl halide in dimethyl sulphoxide/dimethylformamide at 60° C. A total of 5 equivalents of base and alkyl halide were added over 3 days.

EXAMPLE 44

2-Amino[(2-phenoxyethyl)thio]thiazolo[4,5-d]pyrimidin-7(4H)-one

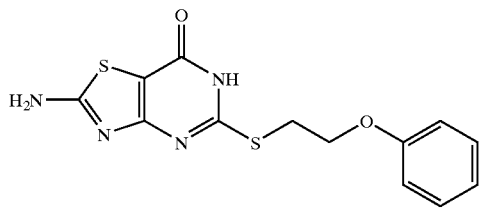

MS: APCI (+ve) 321 (M+1).

EXAMPLE 45

(E)-2-Amino-5-[(3-phenyl-2-propenyl)thio]thiazolo[4,5-d]pyrimidin-7(4H)-one

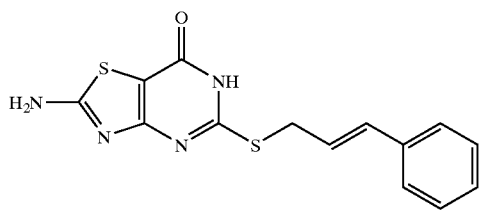

MS: APCI (+ve) 317 (M+1).

EXAMPLE 46

2-Amino-5-[[3-[2,4-bis(1,1-dimethylethyl)phenoxy]propyl]thio]thiazolo[4,5-d]pyrimidin-7(4H)-one

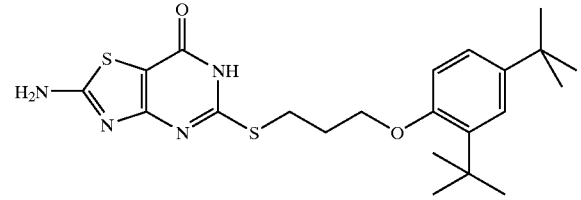

MS: APCI (+ve) 447 (M+1).

EXAMPLE 47

2-Amino-5-[[[(4-trifluoromethyl)phenyl]methyl]thio]thiazolo[4,5-d]pyrimidin-7(4H)-one

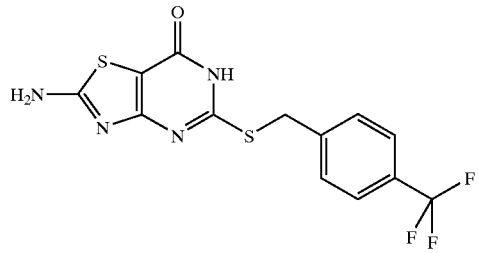

MS: APCI (+ve) 359 (M+1).

EXAMPLES 48–65

The compounds of Examples 48 to 65 were prepared from 2-amino-5,6-dihydro-5-thioxothiazolo[4,5-d]pyrimidin-7(4H)-one (product of Example 3, step a), potassium t-butoxide and the appropriate benzyl halide in dimethyl sulphoxide at room temperature. A total of 1.2 equivalents of base and alkyl halide were used and a reaction time of 24 hours.

EXAMPLE 48

2-Amino-5-[[(3,5-dichlorophenyl)methyl]thio]thiazolo[4,5-d]pyrimidin-7(4H)-one

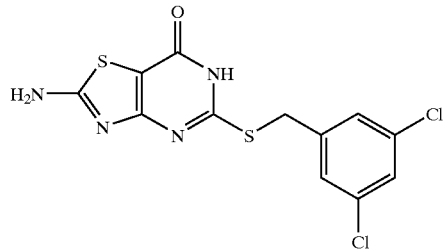

MS: APCI (+ve) 359 (M+1).

EXAMPLE 49

2-Amino-5-[[(2,4-dichlorophenyl)methyl]thio]thiazolo[4,5-d]pyrimidin-7(4H)-one

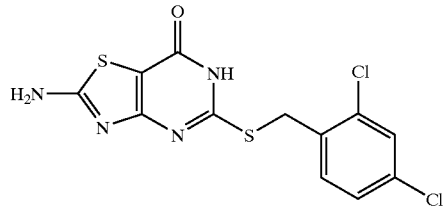

MS: APCI (+ve) 359 (M+1).

EXAMPLE 50

2-Amino-5-[[(3,4-dichlorophenyl)methyl]thio]thiazolo[4,5-d]pyrimidin-7(4H)-one

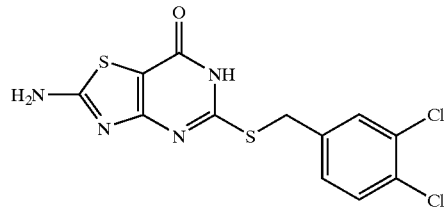

MS: APCI (+ve) 359 (M+1).

EXAMPLE 51

2-Amino-5-[[(3,5-dibromophenyl)methyl]thio]thiazolo[4,5-d]pyrimidin-7(4H)-one

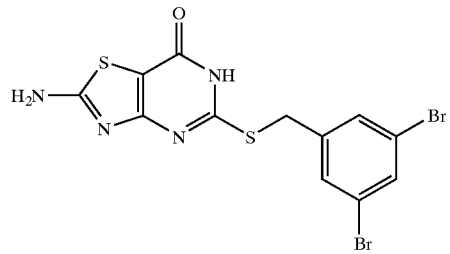

MS: APCI (+ve) 449 (M+1).

EXAMPLE 52

2-Amino-5-[[(2-nitrophenyl)methyl]thio]thiazolo[4,5-d]pyrimidin-7(4H)-one

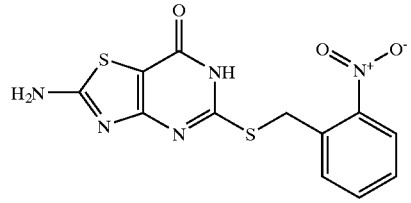

MS: APCI (+ve) 336 (M+1).

EXAMPLE 53

2-Amino-5-[[(2-fluorophenyl)methyl]thio]thiazolo[4,5-d]pyrimidin-7(4H)-one

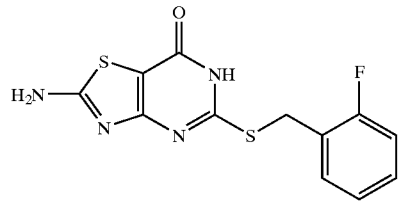

MS: APCI (+ve) 309 (M+1).

EXAMPLE 54

2-Amino-5-[[(2-iodophenyl)methyl]thio]thiazolo[4,5-d]pyrimidin-7(4H)-one

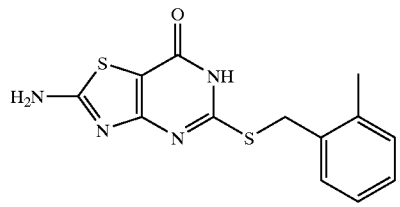

MS: APCI (+ve) 417 (M+1).

EXAMPLE 55

2-Amino-5-[[(3-chlorophenyl)methyl]thio]thiazolo[4,5-d]pyrimidin-7(4H)-one

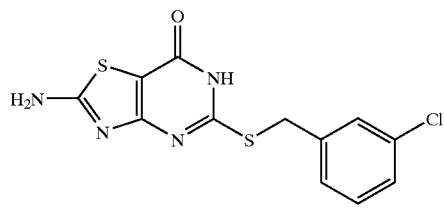

MS: APCI (+ve) 325 (M+1).

EXAMPLE 56

2-Amino-5-[[(2-chlorophenyl)methyl]thio]thiazolo[4,5-d]pyrimidin-7(4H)-one

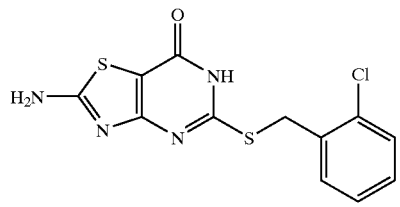

MS: APCI (+ve) 325 (M+1).

EXAMPLE 57

2-Amino-5-[[(4-chloro-2-nitrophenyl)methyl]thio]thiazolo[4,5-d]pyrimidin-7(4H)-one

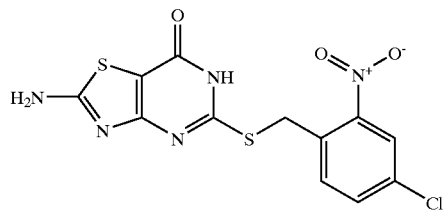

MS: APCI (+ve) 370 (M+1).

EXAMPLE 58

2-Amino-5-[[(3-chloro-4-methoxyphenyl)methyl]thio]thiazolo[4,5-d]pyrimidin-7(4H)-one

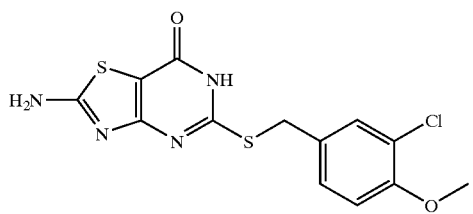

MS: APCI (+ve) 355 (M+1).

EXAMPLE 59

2-Amino-5-[[(2,3-dichlorophenyl)methyl]thio]thiazolo[4,5-d]pyrimidin-7(4H)-one

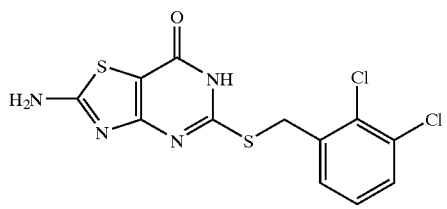

MS: APCI (+ve) 359 (M+1).

EXAMPLE 60

2-Amino-5-[[(3,5-difluorophenyl)methyl]thio]thiazolo[4,5-d]pyrimidin-7(4H)-one

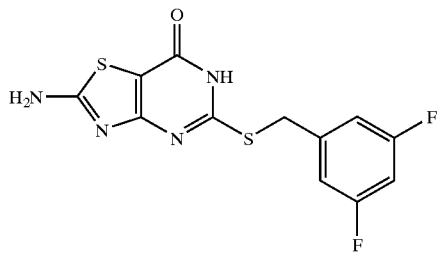

MS: APCI (+ve) 327 (M+1).

EXAMPLE 61

2-Amino-5-[[[(2,4-bis(trifluoromethyl)phenyl]methyl]thio]thiazolo[4,5-d]pyrimidin-7(4H)-one

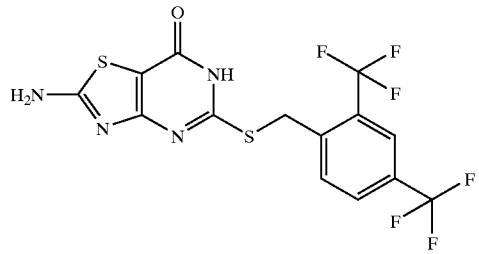

MS: APCI (+ve) 427 (M+1).

EXAMPLE 62

2-Amino-5-[[(2-bromophenyl)methyl]thio]thiazolo[4,5-d]pyrimidin-7(4H)-one

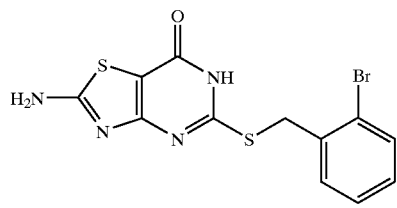

MS: APCI (+ve) 371 (M+1).

EXAMPLE 63

2-Amino-5-[[(2,3,4-trifluorophenyl)methyl]thio]thiazolo[4,5-d]pyrimidin-7(4H)-one

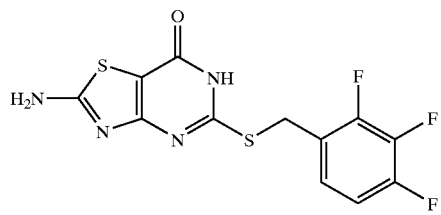

MS: APCI (+ve) 345 (M+1).

EXAMPLE 64

2-Amino-5-[[(3-bromophenyl)methyl]thio]thiazolo[4,5-d]pyrimidin-7(4H)-one

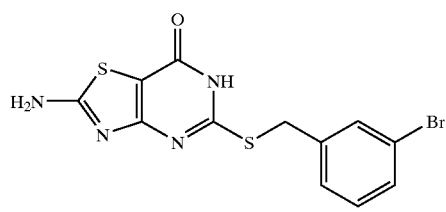

MS: APCI (+ve) 369 (M+1).

EXAMPLE 65

2-Amino-5-[[(2-fluoro-3-methylphenyl)methyl]thio]thiazolo[4,5-d]pyrimidin-7(4H)-one

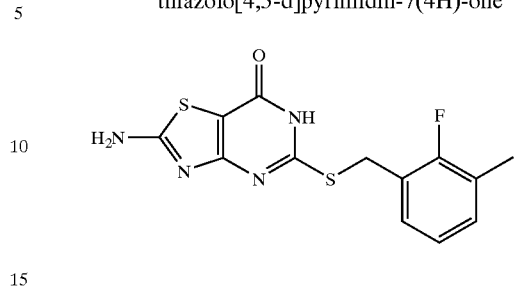

MS: APCI (+ve) 323 (M+1).

EXAMPLES 66–77

The compounds of Examples 66 to 77 were prepared from 7-chloro-5-[(phenylmethyl)thio]thiazolo[4,5-d]pyrimidin-2-amine and the appropriate hydroxyamine 15 in dimethyl sulphoxide at 45° C. A total of 6 equivalents of amine were added and the reaction time was 2 days.

EXAMPLE 66

3-[[2-Amino-5-[(phenylmethyl)thio]thiazolo[4,5-d]pyrimidin-7-yl]amino]-2,2-dimethyl-1-propanol

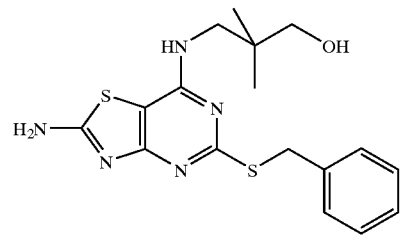

MS: APCI (+ve) 376 (M+1).

EXAMPLE 67

(±)-α-[[[2-Amino-5-[(phenylmethyl)thio]thiazolo[4,5-d]pyrimidin-7-yl]amino]benzenemethanol

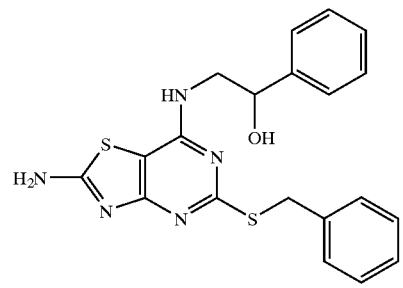

MS: APCI (+ve) 410 (M+1).

EXAMPLE 68

(R)-β-[[2-Amino-5-[(phenylmethyl)thio]thiazolo[4,5-d]pyrimidin-7-yl]amino]benzenepropanol

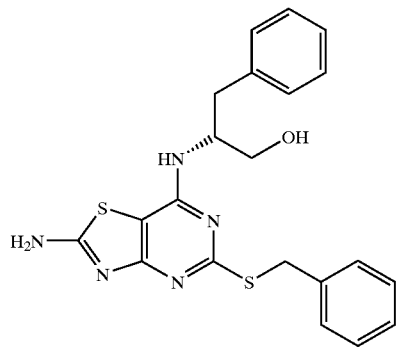

MS: APCI (+ve) 424 (M+1).

EXAMPLE 69

2-[[2-Amino-5-[(phenylmethyl)thio]thiazolo[4,5-d]pyrimidin-7-yl]amino]ethanol

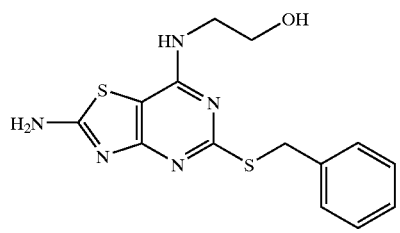

MS: APCI (+ve) 334 (M+1).

EXAMPLE 70

(2R)-2-[[2-Amino-5-[(phenylmethyl)thio]thiazolo[4,5-d]pyrimidin-7-yl]amino]-4-methylpentanol

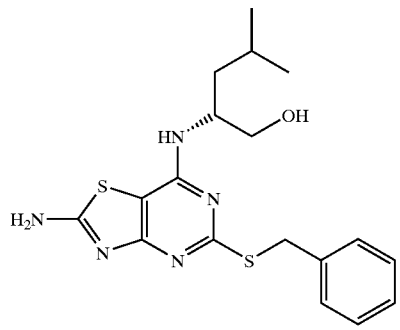

MS: APCI (+ve) 390 (M+1).

EXAMPLE 71

(±)-1-[[2-Amino-5-[(phenylmethyl)thio]thiazolo[4,5-d]pyrimidin-7-yl]amino]-2-propanol

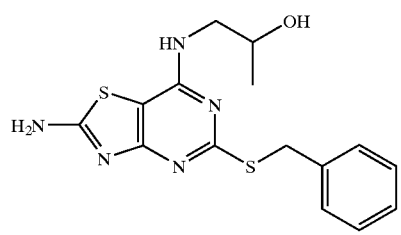

MS: APCI (+ve) 348 (M+1).

EXAMPLE 72

(±)-β-[[2-Amino-5-[(phenylmethyl)thio]thiaolo[4,5-d]pyrimidin-7-yl]amino]-4-chlorobenzenepropanol

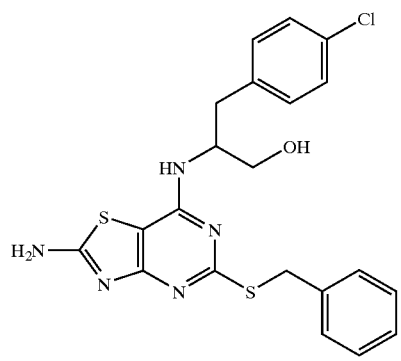

MS: APCI (+ve) 458 (M+1).

EXAMPLE 73

(±)-3-[[2-Amino-5-[(phenylmethyl)thio]thiazolo[4,5-d]pyrimidin-7-yl]amino]-1,2-propanediol

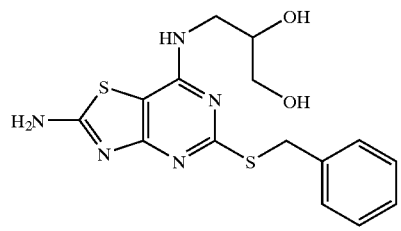

MS: APCI (+ve) 364 (M+1).

EXAMPLE 74

2-[[2-Amino-5-[(phenylmethyl)thio]thiazolo[4,5-d]pyrimidin-7-yl]propylano]ethanol

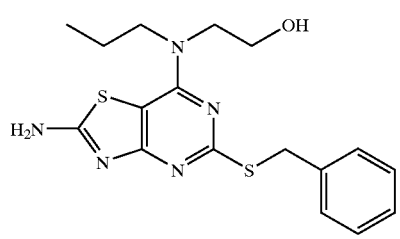

MS: APCI (+ve) 376 (M+1).

EXAMPLE 75

(±)-1-[2-Amino-5-[(phenylmethyl)thio]thiazolo[4,5-d]pyrimidin-7-yl]-3-pyrrolidinol

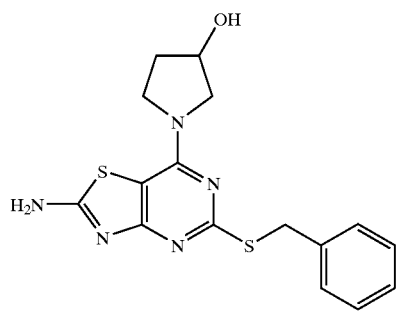

MS: APCI (+ve) 360 (M+1).

EXAMPLE 76

(±)-1-[2-Amino-5-[(phenylmethyl)thio]thiazolo[4,5-d]pyrimidin-7-yl]-3-piperidinol

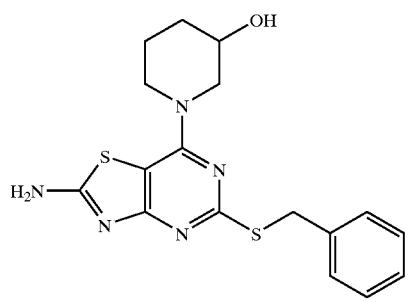

MS: APCI (+ve) 374 (M+1I)

EXAMPLE 77

1-[2-Amino-5-[(phenylmethyl)thio]thiazolo[4,5-d]pyrimidin-7-yl]-4-piperidinol

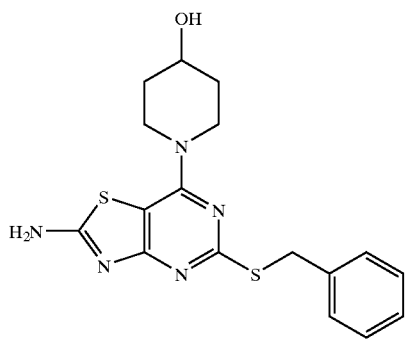

MS: APCI (+ve) 374 M+1).

EXAMPLES 78–110

The compounds of Examples 78 to 110 were prepared from 7-chloro-5-[[3-phenoxyphenyl)methyl]thio]thiazolo[4,5-d]pyrimidin-2-amine (prepared by the method of Example 1, step a) using the product of Example 5) and the appropriate hydroxyamine in tetrahydrofuran at 45° C. A total of 6 equivalents of amine were added and the reaction time was 2 days.

EXAMPLE 78

3-[[2-Amino-5-[[(3-phenoxyphenyl)methyl]thio]thiazolo[4,5-d]pyrimidin-7-yl]amino]-2,2-dimethyl-1-propanol

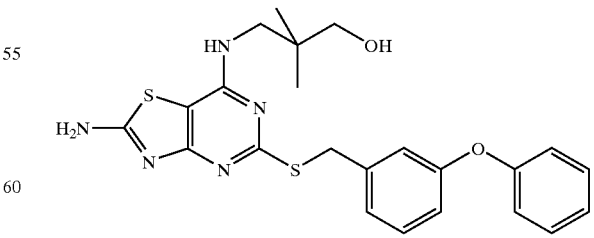

MS: APCI (+ve) 468 (M+1).

EXAMPLE 79

(±)-2-[[2-Amino-5-[[(3-phenoxyphenyl)methyl]thio]
thiazolo[4,5-d]pyrimidin-7-yl]amino]-1-butanol

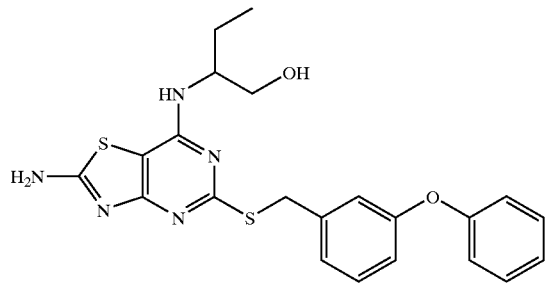

MS: APCI (+ve) 454 (M+1).

EXAMPLE 80

(±)-α-[[[2-Amino-5-[[(3-phenoxyphenyl)methyl]
thio]thiazolo[4,5-d]pyrimidin-7-yl]-amino]methyl]
benzenemethanol

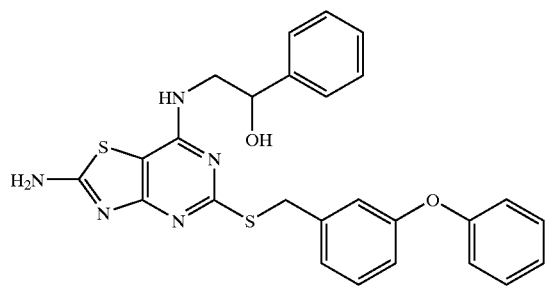

MS: APCI (+ve) 502 (M+1).

EXAMPLE 81

4-[[2-Amino-5-[[(3-phenoxyphenyl)methyl]thio]
thiazolo[4,5-d]pyrimidin-7-yl]amino]-1-butanol

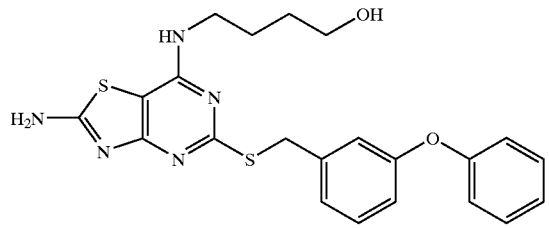

MS: APCI (+ve) 454 (M+1).

EXAMPLE 82

6-[[2-Amino-5-[[(3-phenoxyphenyl)methyl]thio]
thiazolo[4,5-d]pyrimidin-7-yl]amino]-1-hexanol

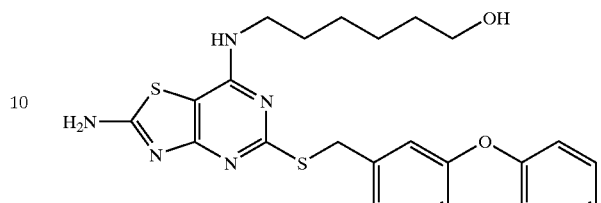

MS: APCI (+ve) 482 (M+1 1).

EXAMPLE 83

4-[[2-Amino-5-[[(3-phenoxyphenyl)methyl]thio]
thiazolo[4,5-d]pyrimidin-7-yl]amino]cyclohexanol

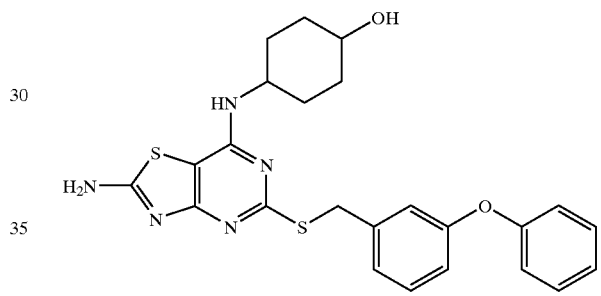

MS: APCI (+ve) 480 (M+1).

EXAMPLE 84

(R)-β-[[2-Amino-5-[[(3-phenoxyphenyl)methyl]thio]
thiazolo[4,5-d]pyrimidin-7-yl]amino]
benzenepropanol

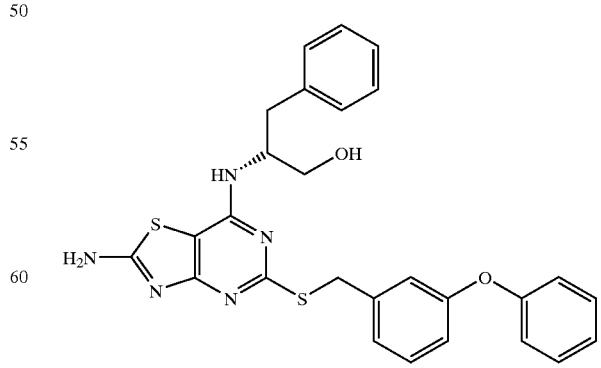

MS: APCI (+ve) 516 (M+1).

EXAMPLE 85

(±)-2-[[2-Amino-5-[[(3-phenoxyphenyl)methyl]thio]thiazolo[4,5-d]pyrimidin-7-yl]amino]-1-propanol

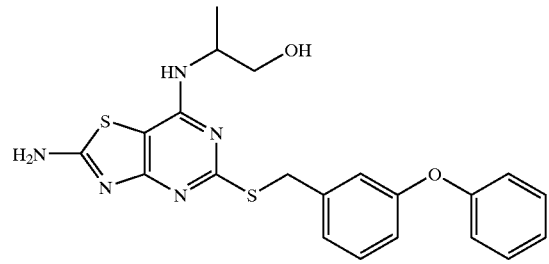

MS: APCI (+ve) 440 (M+1).

EXAMPLE 86

2-[[2-Amino-5-[[(3-phenoxyphenyl)methyl]thio]thiazolo[4,5-d]pyrimidin-7-yl]amino]ethanol

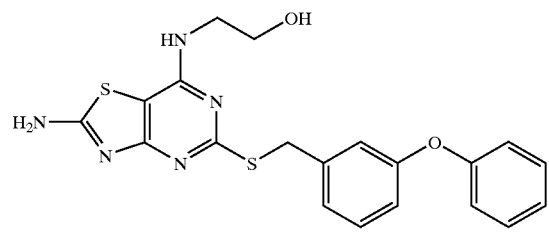

MS: APCI (+ve) 426 (M+1).

EXAMPLE 87

(2R)-2-[[2-Amino-5-[[(3-phenoxyphenyl)methyl]thio]thiazolo[4,5-d]pyrimidin-7-yl]amino]-4-methylpentanol

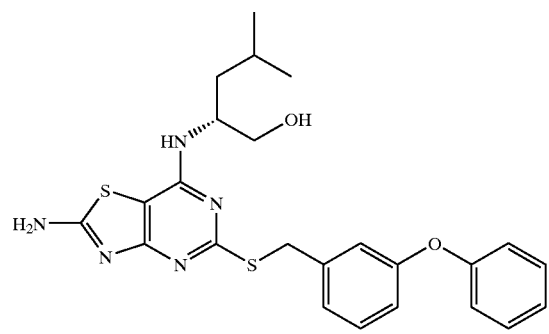

MS: APCI (+ve) 482 (M+1).

EXAMPLE 88

(±)-1-Amino-3-[[2-Amino-5-[[(3-phenoxyphenyl)methyl]thio]thiazolo[4,5-d]pyrimidin-7-yl]amino]-2-propanol

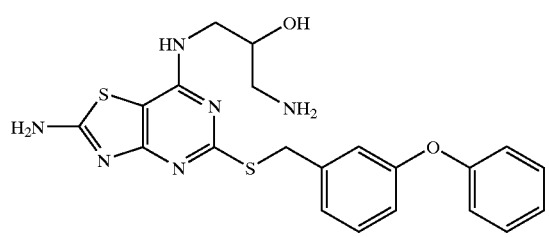

MS: APCI (+ve) 455 (M+1).

EXAMPLE 89

(±)-1-[[2-Amino-5-[[(3-phenoxyphenyl)methyl]thio]thiazolo[4,5-d]pyrimidin-7-yl]amino]-2-propanol

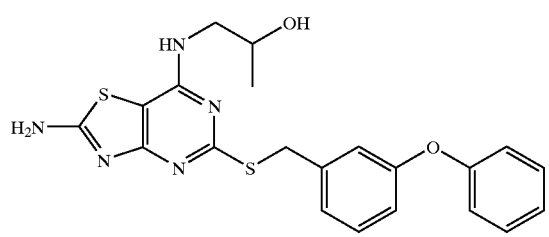

MS: APCI (+ve) 440 (M+1).

EXAMPLE 90

2-[[[2-Amino-5-[[(3-phenoxyphenyl)methyl]thio]thiazolo[4,5-d]pyrimidin-7-yl]amino]methyl]-2-ethyl-1,3-propanediol

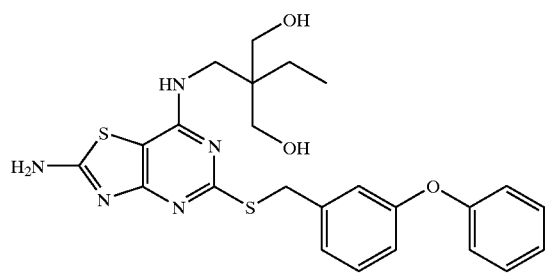

MS: APCI (+ve) 498 (M+1).

EXAMPLE 91

(±)-β-[[2-Amino-5-[[(3-phenoxyphenyl)methyl]thio]thiazolo[4,5-d]pyrimidin-7-yl]amino]-4-chlorobenzenepropanol

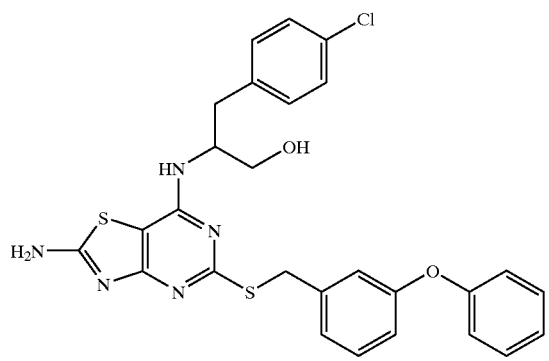

MS: APCI (+ve) 550 (M+1).

EXAMPLE 92

(±)-3-[[2-Amino-5-[[(3-phenoxyphenyl)methyl]thio]thiazolo[4,5-d]pyrimidin-7-yl]amino]-1,2-propanediol

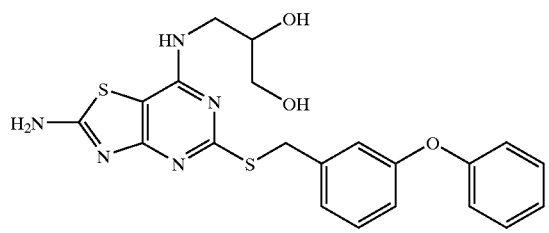

MS: APCI (+ve) 456 (M+1).

EXAMPLE 93

2-[[2-[[2-Amino-5-[[(3-phenoxyphenyl)methyl]thio]thiazolo[4,5-d]pyrimidin-7-yl]amino]ethyl]amino]ethanol

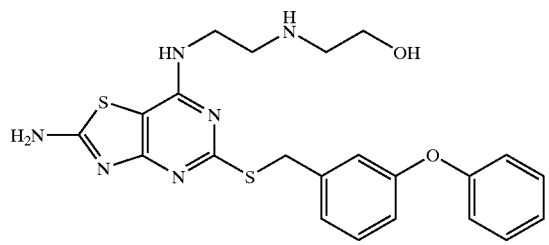

MS: APCI (+ve) 469 (M+1).

EXAMPLE 94

3-[[2-Amino-5-[[(3-phenoxyphenyl)methyl]thio]thiazolo[4,5-d]pyrimidin-7-yl]amino]-1-propanol

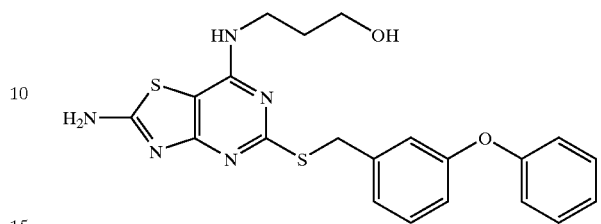

MS: APCI (+ve) 440 (M+1).

EXAMPLE 95

(±)-α-[[[2-Amino-5-[[(3-phenoxyphenyl)methyl]thio]thiazolo[4,5-d]pyrimidin-7-yl]amino]methyl]-3,4-dichlorobenzenepropanol

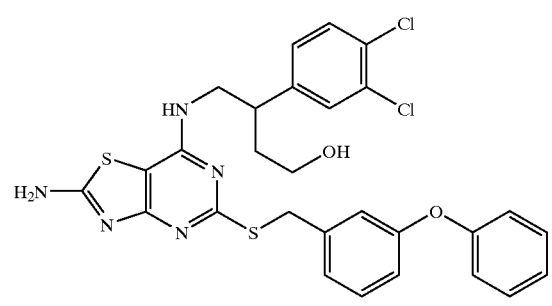

MS: APCI (+ve) 598 (M+1).

EXAMPLE 96

1-[[2-Amino-5-[[(3-phenoxyphenyl)methyl]thio]thiazolo[4,5-d]pyrimidin-7-yl]amino]-2-methyl-2-propanol

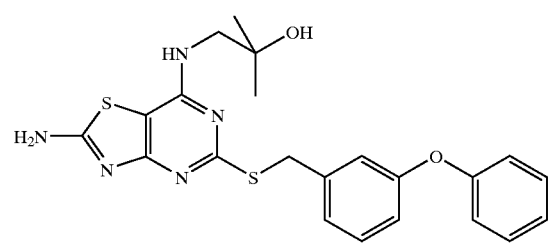

MS: APCI (+ve) 454 (M+1).

EXAMPLE 97

2-[2-[[2-Amino-5-[[(3-phenoxyphenyl)methyl]thio]thiazolo[4,5-d]pyrimidin-7-yl]amino]ethoxy]ethanol

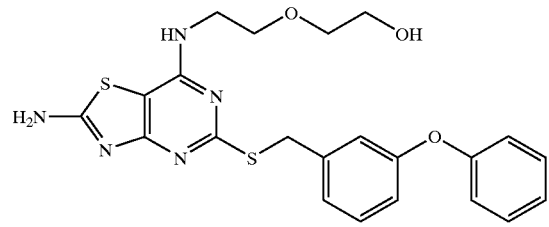

MS: APCI (+ve) 470 (M+1).

EXAMPLE 98

5-[[2-Amino-5-[[(3-phenoxyphenyl)methyl]thio]thiazolo[4,5-d]pyrimidin-7-yl]amino]-1-pentanol

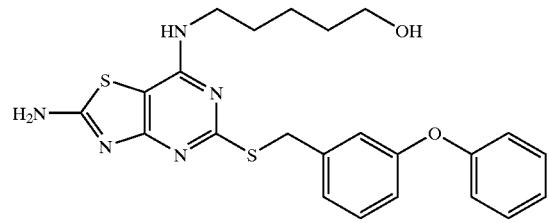

MS: APCI (+ve) 468 (M+1).

EXAMPLE 99

(2S)-2-[[2-Amino-5-[[(3-phenoxyphenyl)methyl]thio]thiazolo[4,5-d]pyrimidin-7-yl]amino]-4-(methylthio)-1-butanol

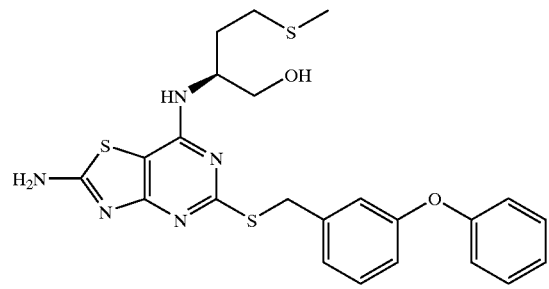

MS: APCI (+ve) 500 (M+1).

EXAMPLE 100

2-[[2-Amino-5-[[(3-phenoxyphenyl)methyl]thio]thiazolo[4,5-d]pyrimidin-7-yl]butylamino]ethanol

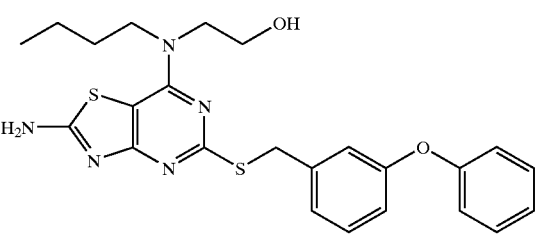

MS: APCI (+ve) 482 (M+1).

EXAMPLE 101

2-[[2-Amino-5-[[(3-phenoxyphenyl)methyl]thio]thiazolo[4,5-d]pyrimidin-7-yl]propylamino]ethanol

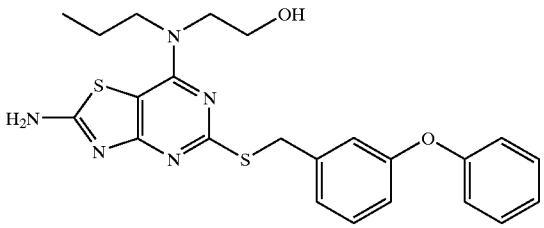

MS: APCI (+ve) 468 (M+1).

EXAMPLE 102

2,2'-[[2-Amino-5-[[(3-phenoxyphenyl)methyl]thio]thiazolo[4,5-d]pyrimidin-7-yl]imino]bisethanol

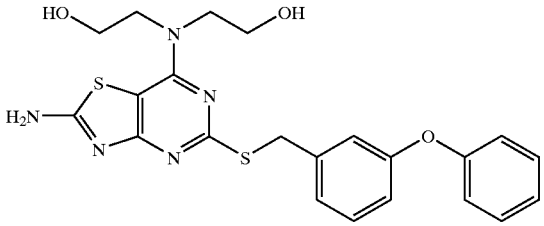

MS: APCI (+ve) 470 (M+1).

EXAMPLE 103

2-[[[2-Amino-5-[[(3-phenoxyphenyl)methyl]thio]thiazolo[4,5-d]pyrimidin-7-yl]-(2-hydroxyethyl)amino]methyl]phenol

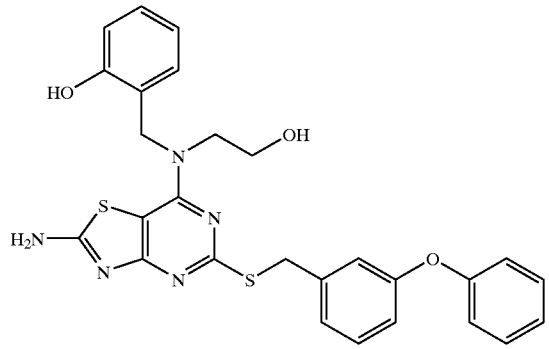

MS: APCI (+ve) 532 (M+1).

EXAMPLE 104

3-[[2-Amino-5-[[(3-phenoxyphenyl)methyl]thio]thiazolo[4,5-d]pyrimidin-7-yl]-(2-hydroxyethyl)amino]-1-propanol

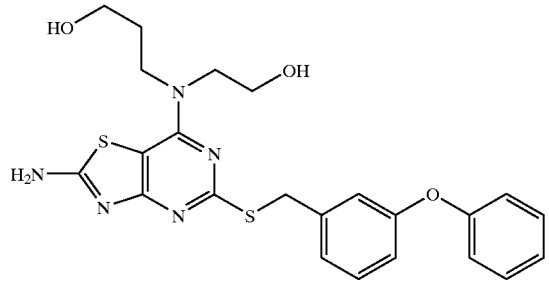

MS: APCI (+ve) 484 (M+1).

EXAMPLE 105

(±)-1-[2-Amino-5-[[(3-phenoxyphenyl)methyl]thio]thiazolo[4,5-d]pyrimidin-7-yl]-3-pyrrolidinol

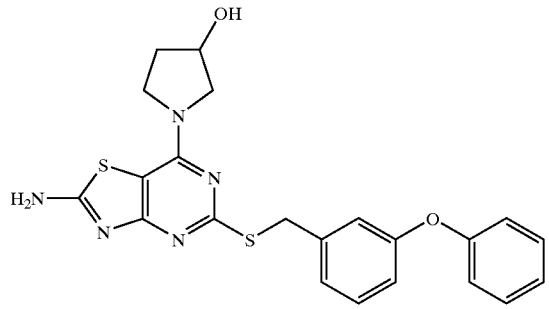

MS: APCI (+ve) 452 (M+1).

EXAMPLE 106

(trans)-1-[2-Amino-5-[[(3-phenoxyphenyl)methyl]thio]thiazolo[4,5-d]pyrimidin-7-yl]-4-hydroxy-L-proline phenylmethyl ester

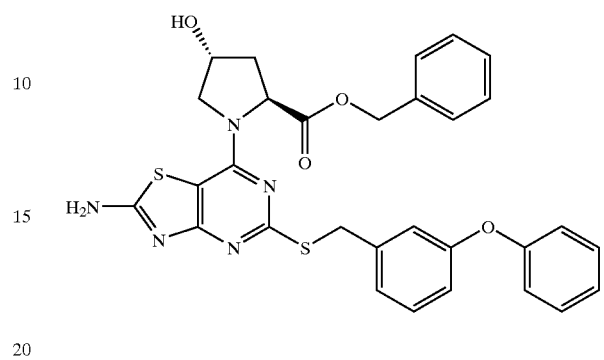

MS: APCI (+ve) 586 (M+1).

EXAMPLE 107

(±)-1-[Amino-5-[[(3-phenoxyphenyl)methyl]thio]thiazolo[4,5-d]pyrimidin-7-yl]-3-piperidinemethanol

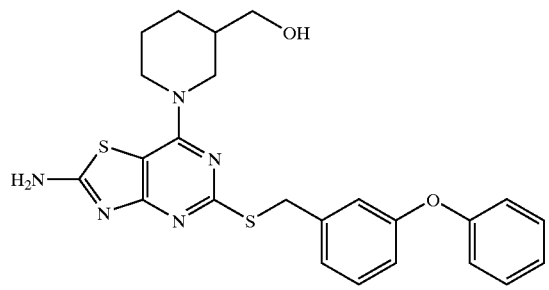

MS: APCI (+ve) 480 (M+1).

EXAMPLE 108

(±)-1-[2-Amino-5-[[(3-phenoxyphenyl)methyl]thio]thiazolo[4,5-d]pyrimidin-7y]-3-piperidinol

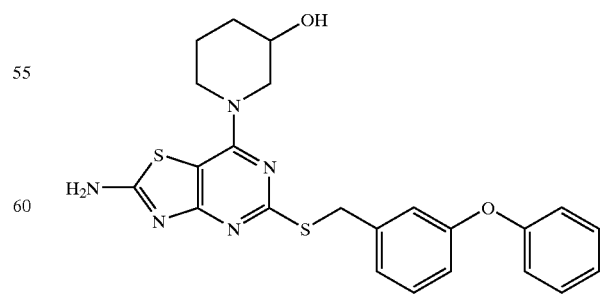

MS: APCI (+ve) 466 (M+1).

EXAMPLE 109

(2S)-1-[2-Amino-5-[[(3-phenoxyphenyl)methyl]thio]thiazolo[4,5-d]pyrimidin-7-yl]-2-pyrrolidinemethanol

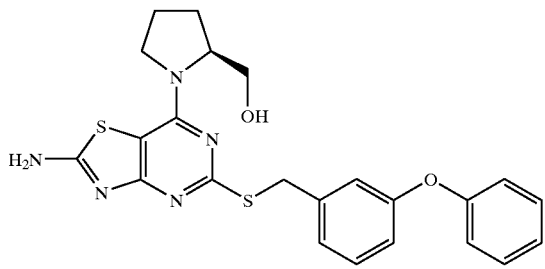

MS: APCI (+ve) 466 (M+1).

EXAMPLE 110

1-[2-Amino-5-[[(3-phenoxyphenyl)methyl]thio]thiazolo[4,5-d]pyrimidin-7-yl]-4-piperidinol

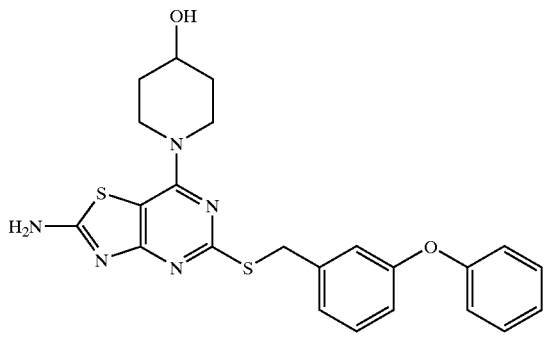

MS: APCI (+ve) 466 (M+1).

EXAMPLE 111

(2R)-2-[[2-Amino-5-[[(3-phenoxyphenyl)methyl]thio]thiazolo[4,5-d]pyrimidin-7-yl]amino]-1-butanol

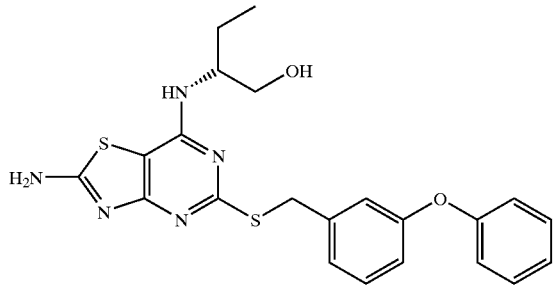

(a) 7-chloro-5-[[(3-phenoxyphenyl)methyl]thio]thiazolo[4,5-d]pyrimidin-2-amine
Prepared by the method of Example 1(a).
m.p. 178–180° C.
MS: APCI (+ve) 401 (M+1).
$^1$H NMR: δ (DMSO) 4.37 (s, 2H), 6.83–7.39 (m, 9H) and 8.95 (s, 2H).

(b) (2R)-2-[[2-Amino-5-[[(3-phenoxyphenyl)methyl]thio]thiazolo[4,5-d]pyrimidin-7-yl]amino]-1-butanol
Prepared by the method of Example 1(b).
m.p. 108–111° C.
MS: APCI (+ve) 454 (M+1).
$^1$H NMR: δ (DMSO) 0.81 (t, 3H), 1.41 (m, 2H), 1.62 (m, 2H), 3.36 (m, 2H), 4.03 (m, 1H), 4.31 (q, 2H), 4.62 (s, 1H), 6.78–7.38 (m, 9H) and 8.00 (s, 2H).

EXAMPLE 112

(2S)-2-[[2-Amino-5-[[(3-phenoxyphenyl)methyl]thio]thiazolo[4,5-d]pyrimidin-7-yl]amino]-1-butanol

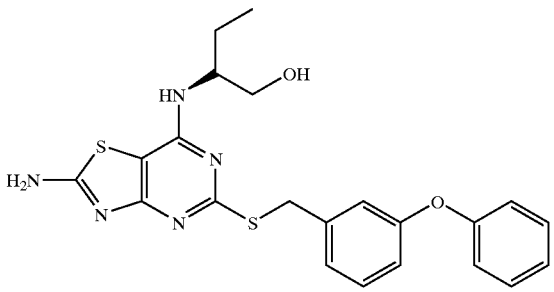

Prepared by the method of Example 1(b).
m.p. 111–114° C.
MS: APCI (+ve) 454 (M+1).
$^1$H NMR: δ (DMSO) 0.81 (t, 3H), 1.41 (m, 2H), 1.62 (m, 2H), 3.36 (m, 2H), 4.02 (br d, 1H), 4.32 (q, 2H), 4.60 (s, 1H), 6.79–7.40 (m, 9H) and 8.04 (s, 2H).

EXAMPLE 113

(2R)-2-[[2-Amino-5-[[(2,3-difluorophenyl)methyl]thio]thiazolo[4,5-d]pyrimidin-7-yl]amino]-1-butanol

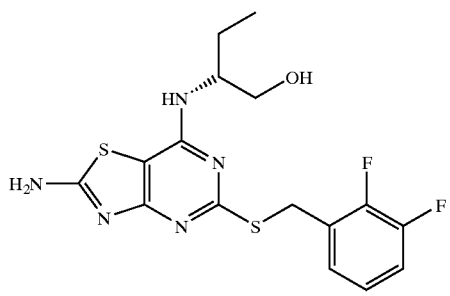

(a) 7-Chloro-5-[[(3,4-difluorophenyl)methyl]thio]thiazolo[4,5-d]pyrimidin-2-amine
Prepared by the method of Example 1(a) using the product of Example 3.
m.p. 209–210° C.
MS: APCI (+ve) 345/6 (M+1).
$^1$H NMR: δ (DMSO) 4.45 (s, 2H), 7.10–7.42 (m, 3H) and 8.90 (br s, 2H).

(b) (2R)-2-[[2-Amino-5-[[(3,4-difluorophenyl)methyl]thio]thiazolo[4,5-d]pyrimidin-7-yl]amino]-1-butanol
Prepared by the method of Example 1(b) using the product of step a) above.
MS: APCI (+ve) 398 (M+1).
$^1$H NMR: δ (DMSO) 0.82 (t, 3H), 1.34–1.71 (m, 4H), 3.37 (m, 2H), 4.03 (br d, 1H), 4.38 (q, 1H), 4.62 (t, 1H), 6.96 (d, 1H), 7.06–7.40 (m, 3H) and 8.02 (s, 2H).

EXAMPLE 114

2-[[2-Amino-5-[[(3-phenoxyphenyl)methyl]thio]
thiazolo[4,5-d]pyrimidin-7-yl]amino]-1,3-
propanediol

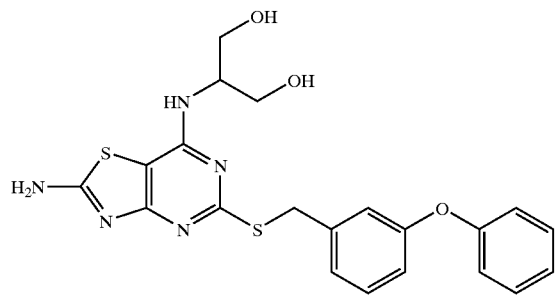

Prepared by the method of Example 1(b).

m.p. 220–222° C.

MS: APCI (+ve) 456 (M+1).

$^1$H NMR: δ (DMSO) 3.50 (t, 4H), 4.13 (m, 1H), 4.32 (s, 2H), 4.60 (t, 2H), 6.78–7.40 (m, 10H) and 8.01 (s, 2H).

EXAMPLE 115

2-[[2-Amino-5-[[(3-phenoxyphenyl)methyl]thio]
thiazolo[4,5-d]pyrimidin-7-yl]amino]-2-methyl-1-
propanol

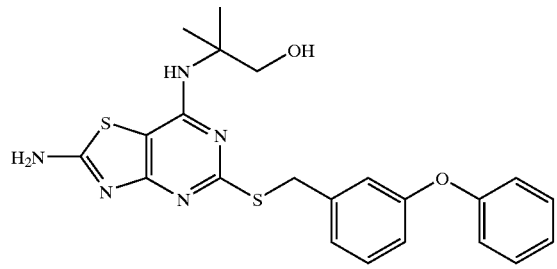

Prepared by the method of Example 1(b) with 10 equivalents of amine, 45–65° C. and reaction time of 3 weeks. Purification by chromatography on silica eluting with methanol/dichloromethane mixtures gave the title compound.

m.p. 126–130° C.

MS: APCI (+ve) 454 (M+1).

$^1$H NMR: δ (DMSO) 1.30 (s, 6H), 3.53 (d, 2H), 4.33 (s, 2H), 4.86 (t, 1H), 6.28 (s, 1H), 6.80–7.40 (m, 9H) and 8.00 (s, 2H).

EXAMPLE 116

2-[[2-Amino-5-[[(2,3-difluorophenyl)methyl]thio]
thiazolo[4,5-d]pyrimidin-7-yl]amino]-2-methyl-1-
propanol

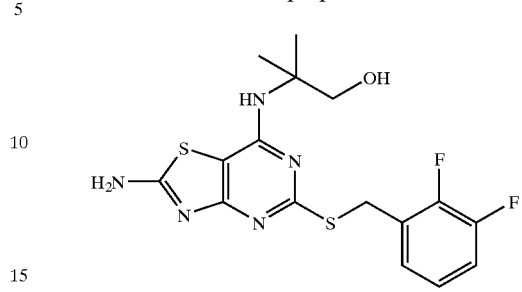

Prepared by the method of Example 1(b) using the product of Example 113, step a), 10 equivalents of amine, 45–65° C. and reaction time of 3 weeks. Purification by chromatography on silica eluting with methanol/dichloromethane mixtures gave the title compound.

m.p. 231–234° C.

MS: APCI (+ve) 398 (M+1).

$^1$H NMR: δ (DMSO) 1.30 (s, 6H), 3.53 (d, 2H), 4.40 (s, 2H), 4.84 (t, 1H), 6.32 (s, 1H), 7.10–7.40 (m, 3H) and 8.03 (s, 2H).

EXAMPLE 117

1-[[2-Amino-5-[[(2,3-difluorophenyl)methyl]thio]
thiazolo[4,5-d]pyrimidin-7-yl]amino]-2-methyl-2-
propanol The product from Example 113, step a) (0.1 g) and 1-amino-2-methyl-propan-2-ol (0.5 g) in tetrahydrofuran (10 ml) was heated in a sealed vessel at 100° C. for 18 hours. The mixture was evaporated to dryness and purified (HPLC, Novapak® C18 column, 0.1% aqueous ammonium acetate:acetonitrile, gradient elution 70:30 to 0:100 over 15 minutes) to afford the title compound (0.051 g).

MS (APCI) 398 (M+H$^+$, 100%).

NMR δH (d$_6$-DMSO) 8.05 (2H, s), 7.39–7.17 (2H, m), 7.16–7.05 (2H, m), 4.51 (1H, s), 5.23 (1H, d), 4.39 (2H, s), 3.37 (2H, d), 1.06 (6H, s).

EXAMPLE 118

5-[[(2,3-Difluorophenyl)methyl]thio]-N$^7$-(2-
fluoroethyl)thiazolo[4,5-d]pyrimidine-2,7-diamine The product from Example 113, step a) (0.1 g), 2-fluoroethylamine hydrochloride (0.5 g) and N,N-ethyldiisopropylamine (0.4 ml) in tetrahydrofuran:water (7 ml, 5:2) was heated in a sealed vessel at 100° C. for 18 hours. The mixture was evaporated to dryness and purified (HPLC, Novapak® C18 column, 0.1% aqueous ammonium acetate:acetonitrile, gradient elution 70:30 to 0:100 over 15 minutes) to afford the title compound (0.027 g).

MS (APCI) 372 (M+H$^+$, 100%).

NMR δH (d$_6$-DMSO) 8.09 (2H, s), 7.36 (1H, t), 7.38–7.10 (3H, m), 4.57 (1H, t), 4.21 (3H, m), 3.71 (1H, q), 4.39 (2H, s), 3.63 (1H, q).

EXAMPLE 119

(1R-trans) 2-[[2-Amino-5-[[(2,3-difluorophenyl)
methyl]thio]thiazolo[4,5-d]pyrimidin-7-yl]amino]
cyclopentanol The product from example 113 step a) (0.2 g), (1R,2R) 2-aminocyclopentanol hydrochloride (1.0 g) and N-ethyldiisopropylamine (1.2 ml) in methanol (15 ml) was heated in a sealed vessel at 120° C. for 90 mins. The mixture was evaporated to dryness and purified (HPLC, Novapak® C18 column, 0.1% aqueous ammonium acetate:acetonitrile, gradient elution 70:30 to 0:100 over 15 minutes) to afford the title compound (0.098 g).

MS (APCI) 410 (M+H$^+$, 100%).

NMR δH (d$_6$-DMSO) 8.04 (2H, s), 7.41–7.27 (2H, m), 7.20 (1H, d), 7.16–7.11 (1H, m), 4.76 (1H, d), 4.41 (2H, dd), 4.09 (1H, m), 3.95 (1H, m), 1.99 (1H, m), 1.89 (1H, m), 1.62 (2H, m), 1.49–1.36 (2H, m).

EXAMPLE 120

(1S-trans) 2-[[2-Amino-5-[[(2,3-difluorophenyl) methyl]thio]thiazolo[4,5-d]pyrimidin-7-yl]amino] cyclopentanol Prepared by the method of Example 119 using the product from Example 113, step a) and (1S,2S)-2-aminocyclopentanol hydrochloride.

MS (APCI) 410 (M+H$^+$, 100%).

NMR δH (d$_6$-DMSO) 8.03 (2H, s), 7.41–7.27 (2H, m), 7.20 (1H, d), 7.167.11 (1H, m), 4.76 (1H, d), 4.41 (2H, dd), 4.09 (1H, m), 3.96 (1H, m), 1.99 (1H, m), 1.89 (1H, m), 1.62 (2H, m), 1.49–1.36 (2H, m).

EXAMPLE 121

2-[[2-Amino-5-[(phenylmethyl)thio]thiazolo[4,5-d] pyrimidin-7-yl]amino]-2-methyl-1-propanol Prepared by the method of Example 117 using the product of Example 1, step a) (0.6 g) and 2-amino-2-methyl-propanol. Purification (SiO$_2$, ethyl acetate as eluant) gave the title compound (0.46 g).

MS (APCI) 362 (M+H$^+$, 100%).

NMR δH (d$_6$-DMSO) 8.00 (2H, s), 7.42–7.20 (5H, m), 6.29 (1H, s), 4.86 (1H, s), 4.35 (2H, s), 3.56 (2H, d), 1.32 (6H, s).

EXAMPLE 122

2-Methyl-2-[[2-(methylamino)-5-[(phenylmethyl) thio]thiazolo[4,5-d]pyrimidin-7-yl]amino]propanol a) 2-[[2-Bromo-5-[(phenylmethyl)thio]thiazolo[4,5-d] pyrimidin-7-yl]amino]-2-methyl-1-propanol To a solution of the product from Example 121 (0.1 g) in bromoform (5 ml) was added isoamylnitrite (0. 13 ml,) and the mixture heated at 60° C. for 10 mins. The mixture was evaporated to dryness then purified (SiO$_2$, ethyl acetate-:dichloromethane 1:9 as eluant) to give the subtitle compound (0.043 g).

MS (APCI) 426 (M+H$^+$, 100%).

b) 2-Methyl-2-[[2-(methylamino)-5-[(phenylmethyl)thio] thiazolo[4,5-d]pyrimidin-7-yl]amino]-1-propanol To a solution of the product from step a) (0.043 g) in methanol (5 ml) was added a saturated solution of methanolic methylamine (20 ml) and the mixture stirred for 30 mins. The mixture was evaporated to dryness and purified (HPLC, Novapak® C18 column, 0.1% aqueous ammonium acetate:acetonitrile, isocratic elution 70:30 over 15 minutes) to afford the title compound (0.026 g).

MS (APCI) 376 (M+H$^+$, 100%).

NMR δH (d$_6$-DMSO) 8.49 (1H, d), 7.42–7.21 (5H, m), 6.34 (1H, s), 4.87 (1H, s), 4.35 (2H, s), 3.56 (2H, d), 2.94 (3H, d), 1.33 (6H, s).

EXAMPLE 123

2-[[2-[[5-[[(2,3-Difluorophenyl)methyl]thio]-2-[(phenylmethyl)amino]thiazolo[4,5-d]pyrimidin-7-yl]amino]-2-methyl-1-propanol a) 2-[[2-Bromo-5-[[(2,3-difluorophenyl)methyl]thio] thiazolo[4,5-d]pyrimidin-7-yl]amino]-2-methyl-1-propanol The sub-title compound was prepared by the method of Example 122, step a) using the product from Example 116.

Purification (SiO$_2$, ethyl acetate:dichloromethane 1:9 as eluant) gave the subtitle compound (0.16 g).

MS (APCI) 461 (M+H$^+$, 100%).

b) 2-[[2-[[5-[[(2,3-Difluorophenyl)methyl]thio]-2-[(phenylmethyl)amino]thiazolo[4,5-d]pyrimidin-7-yl] amino]-2-methyl-1-propanol Prepared by the method of Example 122, step b) using the product from step a). Purification (SiO$_2$, ethyl acetate-:dichloromethane 1:9 as eluant) gave the title compound (0.051 g).

MS (APCI) 488 (M+H$^+$, 100%).

NMR δH (d$_6$-DMSO) 9.08(1H, d), 7.38–7.12 (8H, m), 6.42 (1H, s), 4.82 (1H, t), 4.59 (2H, s), 4.42 (2H, s), 3.54 (2H, d), 1.29 (6H, s).

EXAMPLE 124

5-[[(2,3-Difluorophenyl)methyl]thio]thiazolo[4,5-d] pyrimidin-7(4H)-one

To a solution of the product from Example 3 (1.0 g) in tetrahydrofuran (50 ml) was added isoamyl nitrite (3 ml) and the mixture heated at 70° C. for 2 hours. The mixture was evaporated to dryness and purified (SiO$_2$, ethyl acetate:chloroform 1:9 as eluant) to give the title compound (0.61 g).

MS (APCI) 512 (M+H$^+$, 100%).

NMR δH (d$_6$-DMSO) 13.19(1H, s), 9.61(1H, d), 7.44–7.33 (2H, m), 7.22–15 (1H, m), 4.59 (2H, s).

EXAMPLES 125–148

Example 125 to 148 were prepared by heating, the product of Example 113, step a) (5×10$^{-6}$ moles) with the appropriate amine (10 equivalents) and N-ethyldiisopropylamine (20 equivalents) in N-methylpyrrolidinone (0.3 ml) in a sealed vessel at 120° C. for 16 hours.

EXAMPLE 125

(±)-2-[[2-Amino-5-[[(2,3-difluorophenyl)methyl] thio]thiazolo[4,5-d]pyrimidin-7-yl]amino]-1-butanol

MS (APCI) 398 (M+H$^+$, 100%).

EXAMPLE 126

(1S,2S)-2-[[2-Amino-5-[[(2,3-difluorophenyl) methyl]thio]thiazolo[4,5-d]pyrimidin-7-yl]amino]-cyclohexanol

MS (APCI) 424 (M+H$^+$, 100%).

EXAMPLE 127

(±)-2-[[2-Amino-5-[[(2,3-difuorophenyl)methyl] thio]thiazolo[4,5-d]pyrimidin-7-yl]amino]-1-propanol

MS (APCI) 384 (M+H$^+$, 100%).

EXAMPLE 128

2-[[2-Amino-5-[[(2,3-difluorophenyl)methyl]thio] thiazolo[4,5-d]pyrimidin-7-yl]amino]-1-ethanol

MS (APCI) 370 (M+H$^+$, 100%).

EXAMPLE 129

(2R)-2-[[2-Amino-5-[[(2,3-difluorophenyl)methyl] thio]thiazolo[d]pyrimidin-7-yl]amino]-4-methyl-1-pentanol

MS (APCI) 426 (M+H$^+$, 100%).

EXAMPLE 130

(±)-1-[2-Amino-5-[[(2,3-difluorophenyl)methyl]thio]thiazolo[4,5-d]pyrimidin-7-yl]amino]-2-propanol

MS (APCI) 384 (M+H⁺, 100%).

EXAMPLE 131

2-[[2-Amino-5-[[(2,3-difluorophenyl)methyl]thio]thiazolo[4,5-d]pyrimidin-7-yl]amino]-2-methyl-1,3-propanediol

MS (APCI) 414 (M+H⁺, 100%).

EXAMPLE 132

1-[[[2-Amino-5-[[(2,3-difluorophenyl)methyl]thio]thiazolo[4,5-d]pyrimidin-7-yl]amino]methyl]-cyclohexanol

MS (APCI) 438 (M+H⁺, 100%).

EXAMPLE 133

(2R)-2-[[2-Amino-5-[[(2,3-difuorophenyl)methyl]thio]thiazolo[4,5-d]pyrimidin-7-yl]amino]-1-butanol

MS (APCI) 398 (M+H⁺, 100%).

EXAMPLE 134

2-[[2-Amino-5-[[(2,3-difluorophenyl)methyl]thio]thiazolo[4,5-d]pyrimidin-7-yl]-(2-aminoethyl)amino]-1-ethanol

MS (APCI) 413 (M+H⁺, 100%).

EXAMPLE 135

2-[2-[[2-Amino-5-[[(2,3-difluorophenyl)methyl]thio]thiazolo[4,5-d]pyrimidin-7-yl]amino]ethoxy]-1-ethanol

MS (APCI) 414 (M+H⁺, 100%).

EXAMPLE 136

(αS)-α-[(1R)-1-[[2-Amino-5-[[(2,3-difluorophenyl)methyl]thio]thiazolo[4,5-d]pyrimidin-7-yl]methylamino]ethyl]-benzenemethanol

MS (APCI) 474 (M+H⁺, 100%).

EXAMPLE 137

1-[2-Amino-5-[[(2,3-difluorophenyl)methyl]thio]thiazolo[4,5-d]pyrimidin-7-yl]-4-piperidinol

MS (APCI) 410 (M+H⁺, 100%).

EXAMPLE 138

5-[[(2,3-Difluorophenyl)methyl]thio]-$N^7$-ethyl-thiazolo[4-d]pyrimidine-2,7-diamine

MS (APCI) 354 (M+H⁺, 100%).

EXAMPLE 139

5-[[(2,3-Difluorophenyl)methyl]thio]-$N^7$-(2-propenyl)-thiazolo[4,5-d]pyrimidine-2,7-diamine

MS (APCI) 366 (M+H⁺, 100%).

EXAMPLE 140

2-Bromo-5-[(phenylmethyl)thio]thiazolo[4,5-d]pyrimidin-7(4H)-one

To a solution of the product from Example 9 (2 g) in bromoform (100 ml) was added isoamyl nitrite (2 ml) and the mixture heated at 80° C. for 2 hour. The mixture was evaporated to dryness and purified (SiO₂, dichloromethane as eluant) to give the title compound (0.76 g).

MS (APCI) 355, 354 (M+H⁺), 354 (100%).

EXAMPLE 141

(1S,2S)-2-[[2-Amino-5-[[(2,3-difluorophenyl)methyl]thio]thiazolo[4,5-d]pyrimidin-7-yl]amino]-1-phenyl-1,3-propanediol

MS (APCI) 476 (M+H⁺, 100%).

EXAMPLE 142

2-[[2-Amino-5-[[(2,3-difluorophenyl)methyl]thio]thiazolo[4,5-d]pyrimidin-7-yl]amino]-1,3-propanediol

MS (APCI) 400 (M+H⁺, 100%).

EXAMPLE 143

2-[[2-Amino-5-[[(2,3-difluorophenyl)methyl]thio]thiazolo[4,5-d]pyrimidin-7-yl]amino]-1-ethanol

MS (APCI) 370 (M+H⁺, 100%).

EXAMPLE 144

(±)-5-[[(2,3-Difluorophenyl)methyl]thio]-$N^7$-(2-methoxy-1-methylethyl)-thiazolo[4,5-d]pyrimidine-2,7-diamine

MS (APCI) 398 (M+H⁺, 100%).

EXAMPLE 145

$N^7$-Cyclopropyl-5-[[(2,3-difluorophenyl)methyl]thio]-thiazolo[4,5-d]pyrimidine-2,7-diamine

MS (APCI) 366 (M+H⁺, 100%).

EXAMPLE 146

(±)-2-[[2-Amino-5-[[(2,3-difluorophenyl)methyl]thio]-thiazolo[4,5-d]pyrimidin-7-yl]amino]-1-propanol

MS (APCI) 384 (M+H⁺, 100%).

EXAMPLE 147

4-[[2-Amino-5-[[(2,3-difluorophenyl)methyl]thio]-thiazolo[4,5-d]pyrimidin-7-yl]amino]-1-butanol

MS (APCI) 398 (M+H⁺, 100%).

EXAMPLE 148

5-[[(2,3-Difluorophenyl)methyl]thio]-$N^7$-[2-(1H-imidazol-4-yl)ethyl]-thiazolo[4,5-d]pyrimidine-2,7-diamine

MS (APCI) 420 (M+H⁺, 100%).

EXAMPLES 149–165

The compounds of Example 149 to 165 were prepared by heating 2-[[2-bromo-5-[[(2,3-difluorophenyl)methyl]thio]

thiazolo[4,5-d]pyrimidin-7-yl]amino]-2-methyl-1-propanol (prepared according to the method of Example 122, step a) using the product of Example 116) (5×10⁻⁶ moles) with the appropriate amine (2 equivalents) and N-ethyldiisopropylamine (2 equivalents) in tetrahydrofuran (0.5 ml) at 50–60° C. for 16 hours.

EXAMPLE 149

N-[5-[[(2,3-Difuorophenyl)methyl]thio]-7-[(2-hydroxy-1,1-dimethylethyl)amino]thiazolo[4,5-d]pyrimidin-2-yl]-serine, methyl ester

MS (APCI) 500 (M+H⁺, 100%).

EXAMPLE 150

2-[[5-[[(2,3-Difuorophenyl)methyl]thio]-2-[(1-methylethyl)amino]thiazolo[4,5-d]pyrimidin-7-yl]amino]-2-methyl-1-propanol

MS (APCI) 440 M+H⁺, 100%).

EXAMPLE 151

2-[[5-[[(2,3-Difluorophenyl)methyl]thio]-2-(ethylamino)thiazolo[4,5-d]pyrimidin-7-yl]amino]-2-methyl-1-propanol

MS (APCI) 426 (M+H⁺, 100%).

EXAMPLE 152

2-[[5-[[(2,3-Difluorophenyl)methyl]thio]-2-[[2-(1H-indol-3-yl)ethyl]amino]thiazolo[4,5-d]pyrimidin-7-yl]amino]-2-methyl-1-propanol

MS (APCI) 541 (M+H⁺, 100%).

EXAMPLE 153

2-[[5-[[(2,3-Difluorophenyl)methyl]thio]-2-[(1-naphthalenymethyl)amino]thiazolo[4,5-d]pyrimidin-7-yl]amino]-2-methyl-1-propanol

MS (APCI) 538 (M+H⁺, 100%).

EXAMPLE 154

2-[(5-[[(2,3-Difluorophenyl)methyl]thio]-2-[(1,1-diphenylethyl)amino]thiazolo[4,5-d]pyrimidin-7-yl]amino]-2-methyl-1-propanol

MS (APCI) 578 (M+H⁺, 100%).

EXAMPLE 155

2-[[5-[[(2,3-Difluorophenyl)methyl]thio]-2-[(2,2,2-trifuoroethyl)amino]thiazolo[4,5-d]pyrimidin-7-yl]amino]-2-methyl-1-propanol

MS (APCI) 480 (M+H⁺, 100%).

EXAMPLE 156

2-[[5-[[(2,3-Difluorophenyl)methyl]thio]-2-[[(3,4,5-trimethoxyphenyl)methyl]amino]thiazolo[4,5-d]pyrimidin-7-yl]amino]-2-methyl-1-propanol

MS (APCI) 578 (M+H⁺, 100%).

EXAMPLE 157

2-[[5-[[(2,3-Difluorophenyl)methyl]thio]-2-[(1,1-dimethylethyl)amino]thiazolo[4,5-d]pyrimidin-7-yl]amino]-2-methyl-1-propanol

MS (APCI) 454 (M+H⁺, 100%).

EXAMPLE 158

2-[[5-[[(2,3-Difuorophenyl)methyl]thio]-2-[[2-(2-thienyl)ethyl]amino]thiazolo[4,5-d]pyrimidin-7-yl]amino-2-methyl-1-propanol

MS (APCI) 508 (M+H⁺, 100%).

EXAMPLE 159

2-[[5-[[(2,3-Difuorophenyl)methyl]thio]-2-[(4-methylcyclohexyl)amino]thiazolo[4,5-d]pyrimidin-7-yl]amino]-2-methyl-1-propanol

MS (APCI) 494 (M+⁺, 100%).

EXAMPLE 160

2-[[5-[[(2,3-Difluorophenyl)methyl]thio]-7-[(2-hydroxy-1,1-dimethylethyl)amino]thiazolo[4,5-d]pyrimidin-2-yl]amino]-acetamide

MS (APCI) 455 (M+H⁺, 100%).

EXAMPLE 161

2-[[2-[[2-(4-Aminophenyl)ethyl]amino]-5-[[(2,3-difluorophenyl)methyl]thio]thiazolo[4,5-d]pyrimidin-7-yl]amino]-2-methyl-1-propanol

MS (APCI) 517 (M+H⁺, 100%).

EXAMPLE 162

2-[[5-[[(2,3-Difluorophenyl)methyl]thio]-2-[(2-fluoroethyl)amino]thiazolo[4,5-d]pyrimidin-7-yl]amino]-2-methyl-1-propanol

MS (APCI) 444 (M+H⁺, 100%).

EXAMPLE 163

2-[[2-(Cyclopropylamino)-5-[((2,3-difluorophenyl)methyl]thio]thiazolo[4,5-d]pyrimidin-7-yl]amino]-2-methyl-1-propanol

MS (APCI) 438 (M+H⁺, 100%).

EXAMPLE 164

(±)-2-[[5-[[(2,3-Difluorophenyl)methyl]thio]-7-[(2-hydroxy-1,1-dimethylethyl)amino]thiazolo[4,5-d]pyrimidin-2-yl]amino]-1-pentanol

MS (APCI) 484 (M+H⁺, 100%).

EXAMPLE 165

2-[[5-[[(2,3-Difluorophenyl)methyl]thio]-2-[[2-(2-hydroxyethoxy)ethyl]amino]thiazolo[4,5-d]pyrimidin-7-yl]amino]-2-methyl-1-propanol

MS (APCI) 486 (M+⁺, 100%).

EXAMPLE 166

2-Bromo-5-[[(2,3-difluorophenyl)methyl]thio]-thiazolo[4,5-pyrimidin-7(4H)-one

To a solution of the product from Example 3 (0.2 g) in bromoform (5 ml) was added isoamyl nitrite (0.25 ml) and the mixture heated at 70° C. for 1 hour. The mixture was evaporated to dryness and purified (SiO₂, dichloromethane as eluant) to give the title compound (0.08 g).

NMR δH (d₆-DMSO) 7.42–7.14 (3H, 1), 4.55 (2H, s).

EXAMPLES 167–173

The compounds of Example 167 to 173 were prepared by heating, the product of Example 166 with the appropriate amine (1.2 equivalents) and N-ethyldiisopropylamine (0.1 ml) in tetrahydrofuran (0.2 ml) at 40° C. for 16 hours.

EXAMPLE 167

N-[5-[[(2,3-Difuorophenyl)methyl]thio]-6,7-dihydro-7-oxo-thiazolo[4,5-d]pyrimidin-2-yl]-DL-serine, methyl ester

MS (APCI) 429 (M+H$^+$, 100%).

EXAMPLE 168

5-[[(2,3-Difluorophenyl)methyl]thio]-2-[(1-methylethyl)amino]-thiazolo[4,5-d]pyrimidin-7(4H)-one

MS (APCI) 369 (M+H$^+$, 100%).

EXAMPLE 169

5-[((2,3-Difluorophenyl)methyl]thio]-2-[[2-(1H-indol-3-yl)ethyl]amino]-thiazolo[4,5-d]pyrimidin-7(4H)-one

MS (APCI) 470 (M+H$^+$, 100%).

EXAMPLE 170

2-[[5-[(2,3-Difluorophenyl)methyl]thio]-6,7-dihydro-7-oxo-thiazolo[4,5-pyrimidin-2-yl]amino-3-acetamide

MS (APCI) 384 (M+H$^+$, 100%).

EXAMPLE 171

2-[[2-(4-Aminophenyl)ethyl]amino]-5-[[(2,3-difuorophenyl)methyl]thio]-thiazolo[4,5-d]pyrimidin-7(4H)-one

MS (APCI) 446 (M+H$^+$, 100%).

EXAMPLE 172

5-[[(2,3-Difluorophenyl)methyl]thio]-2-[(2-fluoroethyl)amino]-thiazolo[4,5-d]pyrimidin-7(4H)-one

MS (APCI) 373 (M+H$^+$, 100%).

EXAMPLE 173

5-[[(2,3-Difluorophenyl)methyl]thio]-2-[[2-(2-hydroxyethoxy)ethyl]amino]thiazolo[4,5-d]pyrimidin-7(4H)-one

MS (APCI) 415 (M+H$^+$, 100%).

EXAMPLES 174–218

Example 174 to 218 were prepared by heating the product of Example 122, step a) (5×10$^{-6}$ moles) with the appropriate amine (2 equivalents) and N-ethyldiisopropylamine (2 equivalents) in N-methylpyrrolidinone (0.1 ml) in a sealed vessel at 60° C. for 5 hours.

EXAMPLE 174

2-[[2-(Cyclohexylamino)-5-[(phenylmethyl)thio]thiazolo[4,5-d]pyrimidin-7-yl]amino]-2-methyl-1-propanol

MS (APCI) 444 (M+H$^+$, 100%).

EXAMPLE 175

2-[[2-[(1,1-Dimethylethyl)amino]-5-[(phenylmethyl)thio]thiazolo[4,5-d]pyrimidin-7-yl]amino]-2-methyl-1-propanol

MS (APCI) 418 (M+H$^+$, 100%).

EXAMPLE 176

N-[7-[(2-Hydroxy-1,1-dimethylethyl)amino]-5-[(phenylmethyl)thio]thiazolo[4,5-d]pyrimidin-2-yl]-DL-alanine, methyl ester

MS (APCI) 448 (M+H$^+$, 100%).

EXAMPLE 177

4-[[7-[(2-Hydroxyl-1,1-dimethylethyl)amino]-5-[(phenylmethyl)thio]thiazolo[4,5-d]pyrimidin-2-yl]amino]-cyclohexanol

MS (APCI) 460 (M+H$^+$, 100%).

EXAMPLE 178

2-Methyl-2-[[2-[(4-phenylbutyl)amino]-5-[(phenylmethyl)thio]thiazolo[4,5-d]pyrimidin-7-yl]amino]-1-propanol

MS (APCI) 494 (M+H$^+$, 100%).

EXAMPLE 179

2-Methyl-2-[[5-[(phenylmethyl)thio]-2-[[(tetrahydro-2-furanyl)methyl]amino]thiazolo[4,5-d]pyrimidin-7-yl]amino]-1-propanol

MS (APCI) 446 (M+H$^+$, 100%).

EXAMPLE 180

2-Methyl-2-[[2-[(1-methylethyl)amino]-5-[(phenylmethyl)thio]thiazolo[4,5-d]pyrimidin-7-yl]amino]-1-propanol

MS (APCI) 404 (M+H$^+$, 100%).

EXAMPLE 181

2-[2-[[2-(4-Aminophenyl)ethyl]amino]-5-[(phenylmethyl)thio]thiazolo[4,5-d]pyrimidin-7-yl]amino]-2-methyl-1-propanol

MS (APCI) 481 (M+H$^+$, 100%).

EXAMPLE 182

N-[7-[(2-Hydroxy-1,1-dimethylethyl)amino]-5-[(phenylmethyl)thio]thiazolo[4,5-d]pyrimidin-2-yl]-L-valine, ethyl ester

MS (APCI) 490 (M+H$^+$, 100%).

EXAMPLE 183

(2S)-2-[[7-[(2-Hydroxy-1,1-dimethylethyl)amino]-5-[(phenylmethyl)thio]thiazolo[4,5-d]pyrimidin-2-yl]amino]-4-methyl-pentanamide

MS (APCI) 475 (M+H$^+$, 100%).

EXAMPLE 184

2-Methyl-2-[[2-[(2-phenylethyl)amino]-5-[(phenylmethyl)thio]thiazolo[4,5-d]pyrimidin-7-yl]amino]-1-propanol

MS (APCI) 466 (M+H$^+$, 100%).

EXAMPLE 185

2-[[2-[[(4-Aminophenyl)methyl]amino]-5-(phenylmethyl)thio]thiazolo[4,5-d]pyrimidin-7-yl]amino]-2-methyl-1-propanol

MS (APCI) 467 (M+H$^+$, 100%).

EXAMPLE 186

2-Methyl-2-[[5-[(phenylmethyl)thio]-2-[[2-(2-thienyl)ethyl]amino]thiazolo[4,5-d]pyrimidin-7-yl]amino]-1-propanol

MS (APCI) 472 (M+H$^+$, 100%).

EXAMPLE 187

2-[[2-[[(4-Fluoroethyl)amino]-5-[(phenylmethyl)thio]thiazolo[4,5-d]pyrimidin-7-yl]amino]-2-methyl-1-propanol

MS (APCI) 408 (M+H$^+$, 100%).

EXAMPLE 188

2-Methyl-2-[[2-[[(3-nitrophenyl)methyl]amino]-5-[(phenylmethyl)thio]thiazolo[4,5-d]pyrimidin-7-yl]amino]-1-propanol

MS (APCI) 497 (M+H$^+$, 100%).

EXAMPLE 189

(αR)-α-(1S)-1-[[7-[(2-Hydroxy-1,1-dimethylethyl)amino]-5-[(phenylmethyl)thio]thiazolo[4,5-d]pyrimidin-7-yl]amino]ethyl]benzenemethanol

MS (APCI) 496 (M+H$^+$, 100%).

EXAMPLE 190

2-Methyl-2-[[5-[(phenylmethyl)thio]-2-[[(3,4,5-trimethoxyphenyl)methyl]amino]thiazolo[4,5-d]pyrimidin-7-yl]amino]-1-propanol

MS (APCI) 542 (M+H$^+$, 100%).

EXAMPLE 191

2-Methyl-2-[[2-[(1R-trans)-(2-phenylcyclopropyl)amino]-5-(phenylmethyl)thio]thiazolo[4,5-d]pyrimidin-7-yl]amino]-1-propanol

MS (APCI) 478 (M+H$^+$, 100%).

EXAMPLE 192

2-[[2-[[2-(1H-Indol-3-yl)ethyl]amino]-5-[(phenylmethyl)thio]thiazolo[4,5-d]pyrimidin-7-yl]amino]-2-methyl-1-propanol

MS (APCI) 505 (M+H$^+$, 100%).

EXAMPLE 193

2-[[2-[(1,1-Dimethylpropyl)amino]-5-[(phenylmethyl)thio]thiazolo[4,5-d]pyrimidine-7-yl]amino]-2-methyl-1-propanol

MS (APCI) 432 (M+H$^+$, 100%).

EXAMPLE 194

(±)-2-Methyl-2-[[2-[(1-methylbutyl)amino]-5-[(phenylmethyl)thio]thiazolo[4,5-d]pyrimidin-7-yl]amino]-1-propanol

MS (APCI) 432 (M+H$^+$, 100%).

EXAMPLE 195

(±)-2-Methyl-2-[[2-[(1-methylhexyl)amino]-5-[(phenylmethyl)thio]thiazolo[4,5-d]pyrimidin-7-yl]amino]-1-propanol

MS (APCI) 460 (M+H$^+$, 100%).

EXAMPLE 196

2-8 [2-[[(2-Aminophenyl)methyl]amino]-5-[(phenylmethyl)thio]thiazolo[4,5-d]pyrimidin-7-yl]amino]-2-methyl-1-propanol

MS (APCI) 467 (M+H$^+$, 100%).

EXAMPLE 197

2-[[7-[(2-Hydroxy-1,1-dimethylethyl)amino]-5-[(phenylmethyl)thio]thiazolo[4,6-d]pyrimidin-2-yl]amino]-1,3-propanediol

MS (APCI) 436 (M+H$^+$, 100%).

EXAMPLE 198

2-[[2-[[2-(Ethylthio)ethyl]amino]-5-[(phenylmethyl)thio]thiazolo[d]pyrimidin-7-yl]amino]-2-methyl-1-propanol

MS (APCI) 450 (M+H$^+$, 100%).

EXAMPLE 199

(2S)-2-[[7-[(2-Hydroxy-1,1-dimethylethyl)amino]-5-[(phenylmethyl)thio]thiazolo[4,5-d]pyrimidin-2-yl]amino]-3,3-dimethyl-1-butanol

MS (APCI) 462 (M+H$^+$, 100%).

EXAMPLE 200

(a)-[(1R)-1-[[7-[(2-Hydroxy-1,1-dimethylethyl)amino]-5-[(phenylmethyl)thio]thiazolo[4,5-d]pyrimidin-2-yl]amino]-2-methoxyethyl]benzenemethanol

MS (APCI) 526 (M+H$^+$, 100%).

EXAMPLE 201

2-[[2-(Ethylamino)-5-[(phenylmethyl)thio]thiazolo[4,5-d]pyrimidin-7-yl]amino]-2-methyl-1-propanol

MS (APCI) 390 (M+H$^+$, 100%).

EXAMPLE 202

2-[[2-[[[3-Fluoro-5-(trifluoromethyl)phenyl]methyl]amino]-5-[(phenylmethyl)thio]thiazolo[4,5-d]pyrimidin-7-yl]amino]-2-methyl-1-propanol

MS (APCI) 538 (M+H$^+$, 100%).

EXAMPLE 203

(±)-2-Methyl-2-[[2-[(1-methylpropyl)amino]-5-[(phenylmethyl)thio]thiazolo[4,5-d]pyrimidin-7-yl]amino]-1-propanol

MS (APCI) 418 (M+H$^+$, 100%).

EXAMPLE 204

2-[[2-[[(4-Methoxyphenyl)methyl]amino]-5-[(phenylmethyl)thio]thiazolo[4,5-d]pyrimidin-7-yl]amino]-2-methyl-1-propanol

MS (APCI) 482 (M+H$^+$, 100%).

EXAMPLE 205

2-[[2-[(2-Hydroxyethyl)amino]-5-[(phenylmethyl)thio]thiazolo[4,5-d]pyrimidin-7-yl]amino]-2-methyl-1-propanol

MS (APCI) 406 (M+H$^+$, 100%).

EXAMPLE 206

2-[[2-[[2-(1H-Imidazol-4-yl)ethyl]amino]-5-[(phenylmethyl)thio]thiazolo[4,5-d]pyrimidin-7-yl]amino]-2-methyl-1-propanol

MS (APCI) 456 (M+H$^+$, 100%).

EXAMPLE 207

2-[[2-[(Diphenylmethyl)amino]-5-[(pheylmethyl)thio]thiazolo[4,5-d]pyrimidin-7-yl]amino]-2-methyl-1-propanol

MS (APCI) 528 (M+H$^+$, 100%).

EXAMPLE 208

(2S)-2-[[7-[(2Hydroxy-1,1-dimethylethyl)amino]-5-[(phenylmethyl)thio]thiazolo[4,5-d]pyrimidin-2-yl]amino]-1-butanol

MS (APCI) 434 (M+H$^+$, 100%).

EXAMPLE 209

2-[[2-[[2-(2,2-Diethoxyethyl)amino]-5-[(phenylmethyl)thio]thiazolo[4,5-d]pyrimidin-7-yl]amino]-2-methyl-1-propanol

MS (APCI) 478 (M+H$^+$, 100%).

EXAMPLE 210

4-[[7-[(2-Hydroxy-1,1-dimethylethyl)amino]-5-[(phenylmethyl)thio]thiazolo[4,5-d]pyrimidin-2-yl]amino]-1-butanol

MS (APCI) 434 (M+H$^+$, 100%).

EXAMPLE 211

(1S,2S)-2-[[7-[(2-Hydroxy-1,1-dimethylethyl)amino]-5-[(phenylmethyl)thio]thiazolo[4,5-d]pyrimidin-2-yl]amino]-cyclohexanol

MS (APCI) 460 (M+H$^+$, 100%).

EXAMPLE 212

(±)-2-[[2-[(2-Hydroxy-1-methylethyl)amino]-5-[(phenylmethyl)thio]thiazolo[4,5-d]pyrimidin-7-yl]amino]-2-methyl-1-propanol

MS (APCI) 420 (M+H$^+$, 100%).

EXAMPLE 213

2-[[2-[(2-(2-Hydroxyethoxy)ethyl]amino]-5-[(phenylmethyl)thio]thiazolo[4,5-d]pyrimidin-7-yl]amino]-2-methyl-1-propanol

MS (APCI) 450 (M+H$^+$, 100%).

EXAMPLE 214

(±)-2-[[7-[(2-Hydroxy-1,1-dimethylethyl)amino]-5-[(phenylmethyl)thio]thiazolo[4,5-d]pyrimidin-2-yl]amino]-1-pentanol

MS (APCI) 448 (M+H$^+$, 100%).

EXAMPLE 215

2-[[7-[(2-Hydroxy-1,1-dimethylethyl)amino]-5-[(phenylmethyl)thio]thiazolo[4,5-d]pyrimidin-2-yl]amino]-acetamide

MS (APCI) 419 (M+H$^+$, 100%).

EXAMPLE 216

(±)-2-[[2-[[1-(4-Fluorophenyl)ethyl]amino]-5-[(phenylmethyl)thio]thiazolo[4,5-d]pyrimidin-7-yl]amino]-2-methyl-propanol

MS (APCI) 484 (M+H$^+$, 100%).

EXAMPLE 217

(1R,2S)-2-[[7-[(2-Hydroxy-1,1-dimethylethyl)amino]-5-[(phenylmethyl)thio]thiazolo[4,5-d]pyrimidin-2-yl]amino]-cyclohexanol

MS (APCI) 460 (M+H$^+$, 100%).

EXAMPLE 218

(αS)-α-[(1R)-1-[[7-[(2-Hydroxy-1,1-dimethylethyl)amino]-5-[(phenylmethyl)thio]thiazolo[4,5-d]pyrimidin-2-yl]amino]ethyl]-benzenemethanol

MS (APCI) 496 (M+H$^+$, 100%).

EXAMPLE 219

2-Bromo-7-chloro-5-[(phenylmethyl)thio]thiazolo[4,5-d]pyrimidine

To a solution of the product from Example 1, step a) (10 g) in bromoform (300 ml) was added t-butylnitrite (10 ml) and the mixture heated at 60° C. for 30 mins. The mixture was evaporated to dryness then purified (SiO$_2$, isohexane:dichloromethane 1:1 as eluant) to give the title compound (7.5 g).

MS (APCI) 373 (M+H$^+$, 100%).

NMR δH (d$_6$-DMSO) 7.47–7.24 (5H, m), 4.49 (2H, s).

EXAMPLE 220

7-Chloro-N-methyl-5-[(phenylmethyl)thio]-thiazolo[4 5-d]pyrimidin-2-amine

A solution of the product from Example 219 (0.3 g) in tetrahydrofuran (2 ml) containing methylamine (2.0 molar in THF: 0.81 ml) was stirred for 16 hours. The mixture was evaporated to dryness then purified (SiO$_2$, ethyl acetate-:dichloromethane 1:9 as eluant) to give the title compound (295 mg).

MS (APCI) 323 (M+H$^+$, 100%).

NMR δH (d$_6$-DMSO) 9.30 (1H, s), 7.467.22 (5H, m), 4.40 (2H, s), 3.05 (3H, s).

EXAMPLES 221–223

Examples 221 to 223 were prepared by heating the product of Example 220 (2.5×10$^{-6}$ moles) with the appropriate amine (2 equivalents) and N-ethyldiisopropylamine (3 equivalents) in N-methylpyrrolidinone (0.1 ml) in a sealed vessel at 100° C. for 10 hours.

EXAMPLE 221

(±)-2-[[2-(Methylamino)-5-[(phenylmethyl)thio]thiazolo[4,5-d]pyrimidin-7-yl]amino]-1-propanol

MS (APCI) 362 (M+H$^+$, 100%).

EXAMPLE 222

(2R)-4-Methyl-2-[[2-(methylamino)-5-[(phenylmethyl)thio]thiazolo[4,5-d]pyrimidin-7-yl]amino]-1-pentanol

MS (APCI) 404 (M+H$^+$, 100%).

EXAMPLE 223

N-[2-(Methylamino)-5-[(phenylmethyl)thio]thiazolo[4,5-d]pyrimidin-7-yl]-L-serine, ethyl ester

MS (APCI) 420 (M+H$^+$, 100%).

EXAMPLE 224

7-Chloro-5-[(phenylmethyl)thio]-N-[(tetrahydro-2-furanyl)methyl]-thiazolo[4,5-d]pyrimidin-2-amine Prepared according to the method of Example 220 using the product of Example 219 and tetrahydrofurfurylamine.

MS (APCI) 393 (M+H$^-$, 100%).

NMR δH (d$_6$-DMSO) 9.50 (1H, s), 7.47–7.19 (5H, m), 4.39 (2H, s), 4.06 (1H, m), 3.82 (1H, m), 3.66 (2H, m), 3.50 (1H, m), 2.00–1.53 (4H, m).

EXAMPLES 225–228

Examples 225–228 were prepared by the method of Example 221, using the product of Example 224.

EXAMPLE 225

(±)-2-[[5-[(Phenylmethyl)thio]-2-[[(tetrahydro-2-furanyl)methyl]amino]thiazolo[4,5-d]pyrimidin-7-yl]amino]-1-butanol

MS (APCI) 446 (M+H$^+$, 100%).

EXAMPLE 226

(±)-2-[[5-[(Phenylmethyl)thio]-2-[[(tetrahydro-2-furanyl)methyl]amino]thiazolo[4,5-d]pyrimidin-7-yl]amino]-1-propanol

MS (APCI) 432 (M+H$^+$, 100%).

EXAMPLE 227

(2R)-4-Methyl-2-[[5-[(phenylmethyl)thio]-2-[[(tetrahydro-2-furanyl)methyl]amino]thiazolo[4,5-d]pyrimidin-7-yl]amino]-1-pentanol

MS (APCI) 474 (M+H$^+$, 100%).

EXAMPLE 228

N-[5-[(Phenylmethyl)thio]-2-[[(tetrahydro-2-furanyl)methyl]amino]thiazolo[4,5-d]pyrimidin-7-yl]-L-serine, ethyl ester

MS (APCI) 490 (M+H$^+$, 100%).

EXAMPLE 229

2-[2-[[7-Chloro-5-[(phenylmethyl)thio]thiazolo[4,5-d]pyrimidin-2-yl]amino]ethoxy]ethanol Prepared according to the method of Example 220 using the product of Example 219 (0.3 g) and 2-(2-aminoethoxy)ethanol.

MS (APCI) 397 (M+H$^+$, 100%).

EXAMPLE 230

(±)-2-[[2-[[2-(2-Hydroxyethoxy)ethyl]amino]-5-[(phenylmethyl)thio]thiaolo[4,5-d]pyrimidin-7-yl]amino]-1-propanol Prepared by the method of Example 221, using the product of Example 229.

MS (APCI) 436 (M+H$^+$, 100%).

EXAMPLE 231

4-[2-[[7-Chloro-5-[(phenylmethyl)thio]thiazolo[4,5-d]pyrimidin-2-yl]amino]ethyl]-benzenesulfonamide A solution of the product from Example 219 (0.3 g) in tetrahydrofuran (2 ml) containing 4-(2-aminoethyl)benzenesulfonamide (0.161 g) and N-ethyldiisopropylamine (0.5 ml) was stirred for 16 hours. The mixture was evaporated to dryness then purified (SiO$_2$, ethyl acetate:dichloromethane 4:6 as eluant) to give the title compound (310 mg).

MS (APCI) 492 (M+H$^+$, 100%).

NMR δH (d$_6$-DMSO) 9.45 (1H, s), 7.78–7.23 (9H, m), 4.41 (2H, s), 3.77 (2H, s), 3.02 (2H, t).

EXAMPLES 232–235

Examples 232–235 were prepared by the method of Example 221, using the product of Example 231.

EXAMPLE 232

(±)-4-[2-[[7-[[1-(Hydroxymethyl)propyl]amino]-5-[(phenylmethyl)thio]thiazolo[4,5-d]pyrimidin-2-yl]amino]ethyl]-benzenesulfonamide

MS (APCI) 545 (M+H$^+$, 100%).

EXAMPLE 233

(±)-4-[2-[[7-[(2-Hydroxy-1-methylethyl)amino]-5-[(phenylmethyl)thio]thiazolo[4,5-d]pyrimidin-2-yl]amino]ethyl]-benzenesulfonamide

MS (APCI) 531 (M+H$^+$, 100%).

EXAMPLE 234

4-[2-[[7-[[(1R)-1-(Hydroxymethyl)-3-methylbutyl]amino]-5-[(phenylmethyl)thio]thiazolo[4,5-d]pyrimidin-2-yl]amino]ethyl]-benzenesulfonamide

MS (APCI) 573 (M+H$^+$, 100%).

EXAMPLE 235

(±)-4-[2-[[7-[(2-Hydroxypropyl)amino]-5-[(phenylmethyl)thio]thiazolo[4,5-d]pyrimidin-2-yl]amino]ethyl]benzenesulfonamide

MS (APCI) 531 (M+H$^+$, 100%).

EXAMPLE 236

7-Chloro-N-[2-(1H-imidazol-4-yl)ethyl]-5-[(phenylmethyl)thio]-thiazolo[4,5-d]pyrimidin-2-amine Prepared according to the method of Example 231 using the product of Example 219 and histamine.

MS (APCI) 403 (M+H⁺, 100%).

NMR δH (d₆-DMSO) 11.86 (1H, s), 9.42 (1H, s), 7.56 (1H, s), 7.56–7.23 (5H, m), 6.87 (1H, s), 4.41 (2H, s), 3.73 (2H, m), 2.85 (2H, t).

EXAMPLES 237–248

Examples 237–248 were prepared by the method of Example 221, using the product of Example 236.

EXAMPLE 237

N⁷-Ethyl-N²-[2-(1H-imidazol-4-yl)ethyl]-5-[(phenylmethyl)thio]thiazolo[4,5-d]pyrimidine-2,7-diamine

MS (APCI) 412 (M+H⁺, 100%).

EXAMPLE 238

N²-[2-(1H-Imidazol-4-yl)ethyl]-5-[(phenylmethyl)thio]-N⁷-(3-pyridinylmethyl)thiazolo[4,5-d]pyrimidine-2,7-diamine

MS (APCI) 475 (M+H⁺, 100%).

EXAMPLE 239

(±)-2-[[2-[[2-(1H-Imidazol-4-yl)ethyl]amino]-5-[(phenylmethyl)thio]thiazolo[4,5-d]pyrimidin-7-yl]amino]-1-butanol

MS (APCI) 456 (M+H⁺, 100%).

EXAMPLE 240

(±)-2-[[2-[[2-(1H-Imidazol-4-yl)ethyl]amino]-5-[(phenylmethyl)thio]thiazolo[4,5-d]pyrimidin-7-yl]amino]-1-propanol

MS (APCI) 442 (M+H⁺, 100%).

EXAMPLE 241

(2R)-2-[[2-[[2-(1H-Imidazol-4-yl)ethylamino]-5-[(phenylmethyl)thio]thiazolo[4,5-d]pyrimidin-7-yl]amino]-4-methyl]-pentanol

MS (APCI) 484 (M+H⁺, 100%).

EXAMPLE 242

(±)-1-[[2-[[2-(1H-Imidazol-4-yl)ethyl]amino]-5-[(phenylmethyl)thio]thiazolo[4,5-d]pyrimidin-7-yl]amino]-2-propanol

MS (APCI) 442 (M+H⁺, 100%).

EXAMPLE 243

5-[[2-[[2-(1H-Imidazol-4-yl)ethyl]amino]-5-[(phenylmethyl)thio]thiazolo[4,5-d]pyrimidin-7-yl]amino]-1-pentanol

MS (APCI) 470 (M+H⁺, 100%).

EXAMPLE 244

1-[2-[[2-(1H-Imidazol-4-yl)ethyl]amino]-5-[(phenylmethyl)thio]thiazolo[4,5-d]pyrimidin-7-yl]-4-(phenylmethyl)-4-piperidinol

MS (APCI) 558 (M+H⁺, 100%).

EXAMPLE 245

(±)-1-[2-[[2-(1H-Imidazol-4-yl)ethyl]amino]-5-[(phenylmethyl)thio]thiazolo[4,5-d]pyrimidin-7-yl]-3-piperidinecarboxamide

MS (APCI) 495 (M+H⁺, 100%).

EXAMPLE 246

2-[Ethyl[2-[[2-(1H-imidazol-4-yl)ethyl]amino]-5-[(phenylmethyl)thio]thiazolo[4,5-d]pyrimidin-7-yl]amino]-1-ethanol

MS (APCI) 456 (M+H⁺, 100%).

EXAMPLE 247

N-[2-(1H-Imidazol-4-yl)ethyl]-N⁷,N⁷-dimethyl-5-[(phenylmethyl)thio]-thiazolo[4,5-d]pyrimidine-2,7-diamine

MS (APCI) 412 (M+H⁺, 100%).

EXAMPLE 248

N⁷-[2-(Diethylamino)ethyl]-N⁷-ethyl-N²-[2-(1H-imidazol-4-yl)ethyl]-5-[(phenylmethyl)thio]-thiazolo[4,5-d]pyrimidine-2,7-diamine

MS (APCI) 511 (M+H⁺, 100%).

EXAMPLE 249

7-Chloro-N-(2-phenoxyethyl)-5-[(phenylmethyl)thio]-thiazolo[4,5-d]pyrimidin-2-amine Prepared by the method of Example 231, using the product of Example 219 and 2-phenoxyethylamine.

MS (APCI) 429 (M+H⁺, 100%).

NMR δH (d₆-DMSO) 9.65 (1H, s), 7.46–6.93 (10H, m), 4.41 (2H, s), 4.20 (2H, t), 3.87 (2H, m).

EXAMPLES 250–255

Examples 250–255 were prepared by the method of Example 221, using the product of Example 249.

EXAMPLE 250

N²-(2-Phenoxyethyl)-5-[(phenylmethyl)thio]-N⁷-(3-pyridinylmethyl)-thiazolo[4,5-d]pyrimidine-2,7-diamine

MS (APCI) 501 (M+H⁺, 100%).

EXAMPLE 251

N²-(2-Phenoxyethyl)-N⁷-[1-(phenylmethyl)-4-piperidinyl]-5-[(phenylmethyl)thio]thiazolo[4,5-d]pyrimidine-2,7-diamine

MS (APCI) 583 (M+H⁺, 100%).

EXAMPLE 252

2-Methyl-2-[[2-[(2-phenoxyethyl)amino]-5-[(phenylmethyl)thio]thiazolo[4,5-d]pyrimidin-7-yl]amino]-1-propanol

MS (APCI) 482 (M+H⁺, 100%).

EXAMPLE 253

(±)-2-[[2-[(2-Phenoxyethyl)amino]-5-[(phenylmethyl)thio]thiazolo[4,5-d]pyrimidin-7-yl]amino]-1-propanol

MS (APCI) 468 (M+H⁺, 100%).

EXAMPLE 254

(2R)-4-Methyl-2-r[[2-[(2-phenoxyethyl)amino]-5-[(phenylmethyl)thio]thiazolo[4,5-d]pyrimidin-7-yl]amino]-1-pentanol

MS (APCI) 510 (M+H$^+$, 100%).

EXAMPLE 255

1-[2-[(2-Phenoxyethyl)amino]-5-[(phenylmethyl)thio]thiazolo[4,5-d]pyrimidin-7-yl]-4-(phenylmethyl)-4-piperidinol

MS (APCI) 584 (M+H$^+$, 100%).

EXAMPLE 256

7-Chloro-N-cyclopropyl-5-[(phenylmethyl)thio]-thiazolo[4,5-d]pyrimidin-2-amine

Prepared by the method of Example 220, using the product of Example 219 and cyclopropanamine.

MS (APCI) 351,349 (M+H$^+$, 100%).

NMR δH (d$_6$-DMSO) 7.46–7.22 (5H, m), 4.41 (2H, s), 2.85–2.80 (1H, m), 0.90–0.84 (2H, m), 0.71–0.66 (2H, m).

EXAMPLES 257–260

Example 257 to 260 were prepared by the method of Example 221 using the product of Example 256.

EXAMPLE 257

2-([2-(Cyclopropylamino)-5-[(phenylmethyl)thio]thiazolo[4,5-d]pyrimidin-7-yl]amino]-1-butanol

MS (APCI) 402 (M+H$^+$, 100%).

EXAMPLE 258

2-[[2-(Cyclopropylamino)-5-[(phenylmethyl)thio]thiazolo[4,5-d]pyrimidin-7-yl]amino]-1-propanol

MS (APCI) 388 (M+H$^+$, 100%).

EXAMPLE 259

(2R)-2-[[2-(Cyclopropylamino)-5-[(phenylmethyl)thio]thiazolo[4,5-d]pyrimidin-7-yl]amino]-4-methyl-1-pentanol

MS (APCI) 430 (M+H$^+$, 100%).

EXAMPLE 260

N-[2-(Cyclopropylamino)-5-[(phenylmethyl)thio]thiazolo[4,5-d]pyrimidin-7-yl]-L-serine, ethyl ester

MS (APCI) 446 (M+H$^+$, 100%).

EXAMPLE 261

2-[[7-Chloro-5-[(phenylmethyl)thio]thiazolo[4,5-d]pyrimidin-2-yl]amino]-1-pentanol Prepared by the method of Example 231, using the product of Example 219 and 2-amino-1-pentanol.

MS (APCI) 397, 395 (M+H$^+$, 100%). $^1$H NMR (d$_6$-DMSO) δ 9.29 (1H, s), 7.46–7.22 (5H, m), 4.93 (1H, t), 4.39 (2H, s), 4.07–4.00 (1H, m), 3.50 (2H, t), 1.63–1.43 (2H, m), 1.38–1.32 (2H, m), 0.89 (3H, t).

EXAMPLES 262–264

Example 262 to 264 were prepared by the method of Example 221 using the product of Example 261.

EXAMPLE 262

(2R)-2-[[2-[[1-(Hydroxymethyl)butyl]amino]-5-[(phenylmethyl)thio]thiazolo[4,5-d]pyrimidin-7-yl]amino]-4-methyl-1-pentanol

MS (APCI) 476 (M+H$^+$, 100%).

EXAMPLE 263

N-[2-[[1-(Hydroxymethyl)butyl]amino]-5-[(phenylmethyl)thio]thiazolo[4,5-d]pyrimidin-7-yl]-L-serine, ethyl ester

MS (APCI) 492 (M+H$^+$, 100%).

EXAMPLE 264

(±)-2-[[7-[Cyclohexyl(2-hydroxyethyl)amino]-5-[(phenylmethyl)thio]thiazolo[4,5-d]pyrimidin-2-yl]amino]-1-pentanol

MS (APCI) 502 (M+H$^+$, 100%).

EXAMPLES 265–270

The following examples were prepared by the method of Example 221, using the product of Example 229.

EXAMPLE 265

2-[2-[[7-(Ethylamino)-5-[(phenylmethyl)thio]thiazolo[4,5-d]pyrimidin-2-yl]amino]ethoxy-1-ethanol

MS (APCI) 406 (M+H$^+$, 100%).

EXAMPLE 266

2-[2-[[7-[(1-Methylethyl)amino]-5-[(phenylmethyl)thio]thiazolo[4,5-d]pyrimidin-2-yl]amino]ethoxy)-1-ethanol

MS (APCI) 420 (M+H$^+$, 100%).

EXAMPLE 267

(±)-2-[[2-[[2-(2-Hydroxyethoxy)ethyl]amino]-5-[(phenylmethyl)thio]thiazolo[4,5-d]pyrimidin-7-yl]amino]-1-butanol

MS (APCI) 450 (M+H$^+$, 100%).

EXAMPLE 268

2-[[2-[[2-(2-Hydroxyethoxy)ethyl]amino]-5-[(phenylmethyl)thio]thiazolo[4,5-d]pyrimidin-7-yl]amino]-2-methyl-1-propanol

MS (APCI) 450 (M+H$^+$, 100%).

EXAMPLE 269

(2R)-2-[[2-[[2-(2-Hydroxyethoxy)ethyl]amino]-5-[(phenylmethyl)thio]thiazolo[4,5-d]pyrimidin-7-yl]amino]-4-methyl-1-pentanol

MS (APCI) 478 (M+H$^+$, 100%).

EXAMPLE 270

2-[Cyclohexyl-[2-[[2-(2-hydroxyethoxy)ethyl]
amino]-5-[(phenylmethyl)thio]thiazolo[4,5-d]
pyrimidin-7-yl]amino]ethanol

MS (APCI) 504 (M+H+, 100%).

EXAMPLE 271

(±)-2-[[5-[(Phenylmethyl)thio]-2-(4-
piperidinylamino)thiazolo[4,5-d]pyrimidin-7-yl]
amino]-1-propanol a) 7-Chloro-5-[(phenylmethyl)thio]-N-(4-piperidinyl)-
thiazolo[4,5-d]pyrimidin-2-amine A solution of the product from Example 219 (0.3 g) in tetrahydrofuran (2 ml) containing 4 amino-1-piperidinecarboxylic acid, 1,1-dimethylethyl ester (0. 161 g) and N-ethyldiisopropylamine (0.5 ml) was stirred for 16 hours before evaporating to dryness. The residue was taken into dichloromethane (30 ml) and trifluoroacetic acid (3 ml) added. The solution was stirred for 30 minutes then concentrated to give the title compound (310 mg).

MS (APCI) 392 (M+H+, 100%).

NMR δH (d$_6$-DMSO) 9.47 (1H, s), 8.64–8.48 (2H, s), 7.46–7.23 (5H, s), 4.41 (2H, s), 4,21 (1H, s), 3.34 (2H, m), 3.09 (2H, m), 2.18 (2H, m), 1.69 (2H, m).

b) (±)-2-[[5-[(Phenylmethyl)thio]-2-(4-piperidinylamino)
thiazolo[4,5-d]pyrimidin-7-yl]amino]-1-propanol Prepared by the method of Example 221, using the product of step a).

MS (APCI) 431 (M+H+, 100%).

EXAMPLE 272

N-[2-[[7-Chloro-5-[(phenylmethyl)thio]thiazolo[4,5-
d]pyrimidin-2-yl]amino]ethyl]-acetamide Prepared according to the method of Example 231 using the product of Example 219.

MS (APCI) 396, 394 (M+H+), 394 (100%).

EXAMPLES 273–276

Examples 273–276 were prepared by the method of Example 221 using the product of Example 272.

EXAMPLE 273

(±)-N-[2-[[7-[[1-(Hydroxymethyl)propyl]amino]-5-
[(phenylmethyl)thio]thiazolo[4,5-d]pyrimidin-2-yl]
amino]ethyl]-acetamide

MS (APCI) 447 (M+H+, 100%).

EXAMPLE 274

(±)-N-[2-[[7-[(2-Hydroxy-1-methylethyl)amino]-5-
[(phenylmethyl)thio]thiazolo[4,5-d]pyrimidin-2-yl]
amino]ethyl]acetamide

MS (APCI) 433 (M+H+, 100%).

EXAMPLE 275

N-[2-[[7-[(2-Hydroxyethyl)amino]-5-
[(phenylmethyl)thio]thiazolo[4,5-d]pyrimidin-2-yl]
amino]ethyl]-acetamide

MS (APCI) 419 (M+H+, 100%).

EXAMPLE 276

N-[2-[[7-[[(1R)-1-(Hydroxymethyl)-3-methylbutyl]
amino]-5-[(phenylmethyl)thio]thiazolo[4,5-d]
pyrimidin-2-yl]amino]ethyl]-acetamide

MS (APCI) 475 (M+H+, 100%).

EXAMPLE 277

7-Chloro-5-[(phenylmethyl)thio]-N-[2-(2-thienyl)
ethyl]thiazolo[4,5-d]pyrimidin-2-amine Prepared by the method of Example 231, using the product of Example 219 and 2-(2-thienyl)ethylamine.

MS (APCI), 420, 418 (M+H+), 418 (100%).

NMR δH (d$_6$-DMSO) 7.45–7.32 (5H, m), 6.96 (2H, m), 4.40 (2H, s), 3.78 (2H, s), 3.16 (2H, t).

EXAMPLES 278–284

Examples 276 to 284 were prepared by the method of Example 221 using the product of Example 277.

EXAMPLE 278

$N^7$-(2-Methoxyethyl)-5-[(phenylmethyl)thio]-$N^2$-[2-
(2-thienyl)ethyl]thiazolo[4,5-d]pyrimidine-2,7-
diamine

MS (APCI) 457 (M+H+, 100%).

EXAMPLE 279

$N^7$-(2-Ethoxyethyl)-5-[(phenylmethyl)thio]-$N^2$-[2-
(2-thienyl)ethyl]thiazolo[4,5-d]pyrimidine-2,7-
diamine

MS (APCI) 471 (M+H+, 100%).

EXAMPLE 280

$N^7$-(2,2-Dimethylpropyl)-5-[(phenylmethyl)thio]-
$N^2$-[2-(2-thienyl)ethyl]thiazolo[4,5-d]pyrimidine-2,
7-diamine

MS (APCI) 469 (M+H+, 100%).

EXAMPLE 281

(2R)-4-Methyl-2-[[5-[(phenylmethyl)thio]-2-[[2-
thienyl)ethyl]thiazolo[4,5-d]pyrimidine-7-yl]amino]-
1-pentanol

MS (APCI) 499 (M+H+, 100%).

EXAMPLE 282

(±)-1-[[5-[(Phenylmethyl)thio]-2-[[2-(2-thienyl)
ethyl]amino]thiazolo[4,5-d]pyrimidin-7-yl]amino]-
2-propanol

MS (APCI) 457 (M+H+, 100%).

EXAMPLE 283

(±)-2-[[5-[(Phenylmethyl)thio]-2-[[2-(2-thienyl)
ethyl]amino]thiazolo[4,5-d]pyrimidin-7-yl]amino]-
1-butanol

MS (APCI) 471 (M+H+, 100%).

EXAMPLE 284

(±)-2-[[5-[(Phenylmethyl)thio]-2-[[2-(2-thienyl)
ethyl]amino]thiazolo[4,5-d]pyrimidin-7-yl]amino]-
1-propanol

MS (APCI) 457 (M+H+, 100%).

EXAMPLE 285

2-[[7-Chloro-5-[(phenylmethyl)thio]thiazolo[4,5-d]
pyrimidin-2-yl]amino]-1-ethanol Prepared by the method of Example 231, using the product of Example 219 and 2-aminoethanol.

MS (APCI) 355, 353 (M+H⁺), 353 (100%).

NMR δH (d₆-DMSO) 9.48 (1H, s), 7.45–7.30 (5H, m), 4.95 (1H, t), 4.40 (2H, s), 3.60 (4H, m).

EXAMPLES 286–287

Examples 286 to 287 were prepared by the method of Example 221 using the product of Example 285.

EXAMPLE 286

(2R)-2-[[2-[(2-Hydroxyethyl)amino]-5-[(phenylmethyl)thio]thiazolo[4,5-d]pyrimidin-7-yl]amino]-4-methyl-1-pentanol

MS (APCI) 433 (M+H⁺, 100%).

EXAMPLE 287

(±)-N,N-Diethyl-1-[2-[(2-hydroxyethyl)amino]-5-[(phenylmethyl)thio]thiazolo[4,5-d]pyrimidin-7-yl]-3-piperidinecarboxamide

MS (APCI) 500 (M+H⁺, 100%).

EXAMPLE 288

3-[[7-Chloro-5-[(phenylmethyl)thio]thiazolo[4,5-d]pyrimidin-2-yl]amino]-1-propanol Prepared by the method of Example 231, using the product of Example 219 and 3-aminopropanol.

MS (APCI) 369, 367 (M+H⁺), 367 (100%).

NMR δH (d₆-DMSO) 9.36 (1H, s), 7.43–7.27 (5H, m), 4.57 (1H, t), 4.40 (2H, s), 3.49 (4H, m), 1.75 (2H, m).

EXAMPLES 289–291

Examples 289–291 were prepared by the method of Example 221 using the product of Example 288.

EXAMPLE 289

(2R)-2-[[2-[(3-Hydroxypropyl)amino]-5-[(phenylmethyl)thio]thiazolo[4,5-d]pyrimidin-7-yl]amino]-4-methyl-1-pentanol

MS (APCI) 447 (M+H⁺, 100%).

EXAMPLE 290

(±)-2-[[2-[(3-Hydroxypropyl)amino]-5-[(phenylmethyl)thio]thiazolo[4,5-d]pyrimidin-7-yl]amino]-1-butanol

MS (APCI) 419 (M+H⁺, 100%).

EXAMPLE 291

(±)-2-[[2-[(3-Hydroxypropyl)amino]-5-[(phenylmethyl)thio]thiazolo[4,5-d]pyrimidin-7-yl]amino]-1-propanol

MS (APCI) 405 (M+H⁺, 100%).

EXAMPLE 292

2-[[7-Chloro-5-[(phenylmethyl)thio]thiazolo[4,5-d]pyrimidin-2-yl]amino]-acetamide Prepared by the method of Example 231, using the product of Example 219 and glycinamide hydrochloride.

MS (APCI) 368, 66 (M+H⁺), 366 (100%).

NMR δH (d₆-DMSO) 7.61 (1H, s), 7.45–7.24 (6H, m), 4.40 (2H, s), 4.14–4.12 (2H, m), 9.57 (1H, s).

EXAMPLE 293

2-[[7-[(2-Hydroxy-1-methylethyl)amino]-5-[(phenylmethyl)thio]thiazolo[4,5-d]pyrimidin-2-yl]amino-acetamide Prepared according to the method of Example 221 using the product of Example 292.

MS (APCI) 404 (M+H⁺, 100%).

EXAMPLE 294

4-[[7-Chloro-5-[(phenylmethyl)thio]thiazolo[4,5-d]pyrimidin-2-yl]-3-azetidinyl]-1-piperazinesulfonamide Prepared by the method of Example 231, using the product of Example 219 and 3-azetidinyl-1-piperazinesulfonamide.

MS (APCI), 512, 514 (M+H⁺), 512 (100%).

NMR δH (d₆-DMSO) 7.69–7.22 (5H, m), 6.80 (2H, s), 4.40 (2H, s), 4.34–4.12 (4H, m), 3.56–3.50 (1H, m), 3.40 (4H, s), 3.00 (4H, s).

EXAMPLE 295

4-[1-[7-[(4-Methylcyclohexyl)amino]-5-[(phenylmethyl)thio]thiazolo[4,5-d]pyrimidin-2-yl]-3-azetidinyl]-1-piperazinesulfonamide, Prepared by the method of Example 221, using the product of Example 294.

MS (APCI) 588 (M+H⁺, 100%).

EXAMPLE 296

7-Chloro-N-[[2-(4-morpholinyl)ethyl]-5-[(phenylmethyl)thio]-thiazolo[4,5-d]pyrimidin-2-amine Prepared by the method of Example 231, using the product of Example 219 and 2-(4-morpholinyl)ethyl]amine.

MS (APCI) 424, 422 (M+H⁺), 422 (100%).

NMR δH (d₆-DMSO) 9.34 (1H, s), 7.68–7.23 (5H, m), 4.40 (2H, s), 3.59–3.56 (6H, m), 2.54 (2H, t), 2.44–2.41 (4H, m).

EXAMPLES 297–300

Examples 297–300 were prepared according to the method of Example 221 using the product of Example 296.

EXAMPLE 297

3-[[2-[[2-(4-Morpholinyl)ethyl]amino]-5-[(phenylmethyl)thio]thiazolo[4,5-d]pyrimidin-7-yl]amino]-1-propanol

MS (APCI) 460 (M+H⁺, 100%).

EXAMPLE 298

2-Methyl-2-[[2-[[2-(4-morpholinyl)ethyl]amino]-5-[(phenylmethyl)thio]thiazolo[4,5-d]pyrimidin-7-yl]amino]-1-propanol

MS (APCI) 464 (M+H⁺, 100%).

EXAMPLE 299

(±)-2-[[2-[[2-(4-Morpholinyl)ethyl]amino]-5-[(phenylmethyl)thio]thiazolo[4,5-d]pyrimidin-7-yl]amino]-1-propanol

MS (APCI) 460 (M+H$^+$, 100%).

EXAMPLE 300

(2R)-4-Methyl-2-[[2-[[2-(4-morpholinyl)ethyl]amino]-5-[(phenylmethyl)thio]thiazolo[4,5-d]pyrimidin-7-yl]amino]-1-pentanol

MS (APCI) 502 (M+H$^+$, 100%).

EXAMPLES 301–302

Examples 301–302 were prepared by the method of Example 12 using the product of Example 140.

EXAMPLE 301

2-[[2-(3,4-Dihydroxyphenyl)ethyl]amino]-5-[(phenylmethyl)thio]-thiazolo[4,5-d]pyrimidin-7(4H)-one

MS (APCI) 427 (M+H$^+$, 100%).

EXAMPLE 302

(±)-2-[(2-Hydroxy-1-methylethyl)amino]-5-[(phenylmethyl)thio]-thiazolo-4,5-d]pyrimidin-7(4H)-one

MS (APCI) 349 (M+H$^+$, 100%).

Pharmacological Data
Ligand Binding Assay

[$^{125}$-]IL-8 (human, recombinant) was purchased from Amersham, U.K with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp 16283–16291). hrCXCR2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 µg/ml soybean trypsin inhibitor, 3 mM benzamidine, 0.5 µg/ml leupeptin and 100 µg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at −70° C. in homogenisation buffer supplemented with Tyrode's salt solution (137 mM NaCl, 2.7 mM KCl, 0.4 mM NaH$_2$PO$_4$), 0.1% (w/v) gelatin and 10% (v/v) glycerol.

All assays were performed in a 96-well MultiScreen 0.45 µm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM CaCl$_2$, 1 mM MgCl$_2$, 0.125 mg/ml bacitracin and 0.1% (w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter.

The compounds of formula (I) according to the Examples were found to have IC$_{50}$ values of less than (<) 10 µM.

Intracellular Calcium Mobilisation Assay

Human neutrophils were prepared from EDTA-treated peripheral blood, as previously described (Baly et al. (1997) Methods in Enzymology 287 pp 70–72), in storage buffer [Tyrode's salt solution (137 mM NaCl, 2.7 mM KCl, 0.4 mM NaH$_2$PO$_4$) supplemented with 5.7 mM glucose and 10 mM HEPES (pH 7.4)].

The chemokine GROα (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al (1990) Biochem. J. 269, pp 513–519). Cells were loaded for 1 hour at 37° C. in loading buffer (storage buffer with 0.1% (w/v) gelatin) containing 5 µM fluo-3 AM ester, washed with loading buffer and then resuspended in Tyrode's salt solution supplemented with 5.7 mM glucose, 0.1% (w/v) bovine serum albumin (BSA), 1.8 mM CaCl$_2$ and 1 mM MgCl$_2$. The cells were pipetted into black walled, clear bottom, 96 well micro plates (Costar, Boston, U.S.A.) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an A$_{50}$ concentration of GROα and the transient increase in fluo-3 fluorescence ($\lambda_{Ex}$=490 nm and $\lambda_{EM}$=520 nm) monitored using a FLIPR (Fluorometric Imaging Plate Reader, Molecular Devices, Sunnyvale, U.S.A.).

The compounds of formula (i) according to the examples were tested and found to be antagonists of the CXCR2 receptor in human neutrophils.

What is claimed is:

1. A compound of general formula (I)

[Structure: thiazolo[4,5-d]pyrimidine with X at position 7, R$^1$ on thiazole, and S—R$^2$ on pyrimidine]

wherein R$^1$ represents a hydrogen atom, or a group —NR$^3$R$^4$;

R$^3$ and R$^4$ each independently represent a hydrogen atom, or a 4-piperidinyl, C$_3$–C$_6$ cycloalkyl or C$_1$–C$_8$ alkyl group, which latter two groups are optionally substituted by one or more substituent groups independently selected from halogen atoms and —NR$^5$R$^6$, —CONR$^5$R$^6$, —OR$^7$, —COOR$^7$, —NR$^8$COR$^9$, —SR$^{10}$, —SO$_2$R$^{10}$, —SO$_2$NR$^5$R$^6$, —NR$^8$SO$_2$R$^9$, morpholinyl, C$_1$–C$_4$ alkyl, C$_3$–C$_8$ cycloalkyl, tetrahydrofuranyl and aryl groups, wherein an aryl substituent group is optionally a phenyl, naphthyl, thienyl, pyridinyl, imidazolyl or indolyl group, each of which is optionally substituted by one or more substituents independently selected from halogen atoms and cyano, nitro, —NR$^5$R$^6$, —CONR$^5$R$^6$, —OR$^7$, —NR$^8$COR$^9$, —SO$_2$NR$^5$R$^6$, —NR$^8$SO$_2$R$^9$, C$_1$–C$_6$ alkyl and trifluoromethyl groups, or R$^3$ and R$^4$ together with the nitrogen atom to which they are attached form a 4- to 7-membered saturated heterocyclic ring system, which ring system is optionally substituted by one or more substituent groups independently selected from

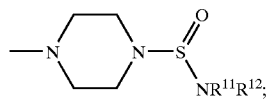

—NR$^5$R$^6$, —CONR$^5$R$^6$, —OR$^7$, —COOR$^{10}$, —NR$^8$COR$^9$, and C$_1$–C$_6$ alkyl optionally substituted by one or more substituents independently selected from halogen atoms and —NR$^{11}$R$^{12}$ and —OR$^7$ groups;

X represents a group —OH or —NR$^{13}$R$^{14}$;

R$^{13}$ and R$^{14}$ each independently represent a hydrogen atom, a 4-piperidinyl group optionally substituted by a C$_1$–C$_4$ alkylphenyl substituent group, or a C$_3$–C$_7$ carbocyclic, C$_1$–C$_8$ alkyl, C$_2$–C$_6$ alkenyl or C$_2$–C$_6$ alkynyl group, which latter four groups are optionally substituted by one or more substituent groups independently selected from halogen atoms and —NR$^5$R$^6$, —CONR$^5$R$^6$, —OR$^7$, —COOR$^7$, —NR$^8$COR$^9$, SR$^{10}$, —SO$_2$R$^{10}$, —SO$_2$NR$^5$R$^6$, —NR$^8$SO$_2$R$^9$, morpholinyl, C$_1$–C$_4$ alkyl, C$_3$–C$_6$ cycloalkyl and aryl groups, wherein an aryl substituent group is optionally a phenyl, naphthyl, thienyl, pyridinyl, imidazolyl or indolyl group, each of which is optionally substituted by one or more substituents independently selected from halogen atoms and cyano, nitro, —NR$^5$R$^6$, —CONR$^5$R$^6$, —OR$^7$, —NR$^8$COR$^9$, —SO$_2$NR$^5$R$^6$, NR$^8$SO$_2$R$^9$, C$_1$–C$_6$ alkyl and trifluoromethyl groups, or R$^{13}$ and R$^{14}$ together with the nitrogen atom to which they are attached form a 4- to 7-membered saturated heterocyclic ring system, which ring system is optionally substituted by one or more substituent groups independently selected from —NR$^5$R$^6$, —CONR$^5$R$^6$, —OR$^7$, —COOR$^7$, —NR$^8$COR$^9$, and C$_1$–C$_6$ alkyl optionally substituted by one or more substituents independently selected from halogen atoms and phenyl, —NR$^{11}$R$^{12}$ and —OR$^7$ groups;

R$^2$ represents a C$_1$–C$_6$ alkyl or C$_2$–C$_6$ alkenyl group optionally substituted by a phenyl or phenoxy group, wherein the phenyl or phenoxy group is itself optionally substituted by one or more substituents independently selected from halogen atoms and nitro, C$_1$–C$_6$ alkyl, trifluoromethyl, —OR$^7$, —C(O)R$^7$, —SR$^{10}$, —NR$^{15}$R$^{16}$ and phenyl groups; R$^5$ and R$^6$ each independently represent a hydrogen atom or a C$_1$–C$_6$ alkyl or phenyl group, each of which is optionally substituted by one or more substituent groups independently selected from halogen atoms, phenyl, —OR$^{17}$ and —NR$^{15}$R$^{16}$, or R$^5$ and R$^6$ together with the nitrogen atom to which they are attached form a 4- to 7-membered saturated heterocyclic ring system optionally comprising a further heteroatom selected from oxygen and nitrogen atoms, which ring system is optionally substituted by one or more substituent groups independently selected from phenyl, —OR$^{17}$—COOR$^{17}$, —NR$^{15}$R$^{16}$, —CONR$^{15}$R$^{16}$, —NR$^{15}$COR$^{16}$, —SONR$^{15}$R$^{16}$, and C$_1$–C$_6$ alkyl optionally substituted by one or more substituents independently selected from halogen atoms and —NR$^{15}$R$^{16}$ and —OR$^{17}$ groups;

R$^7$ and R$^9$ each independently represent a hydrogen atom or a C$_1$–C$_6$ alkyl or phenyl group, each of which is optionally substituted by one or more substituent groups independently selected from halogen atoms, phenyl, —OR$^{17}$ and —NR$^{15}$R$^{16}$; and each of R$^8$, R$^{10}$, R$^{11}$, R$^{12}$, R$^{15}$, R$^{16}$ and R$^{17}$ independently represents a hydrogen atom or a C$_1$–C$_6$ alkyl or phenyl group; with the proviso that when R$^1$ and X both represent —NH$_2$, then R$^2$ does not represent a methyl group;

or a pharmaceutically acceptable salt or solvate or tautomer thereof.

2. A compound according to claim 1, wherein R$^1$ represents a group —NR$^3$R$^4$.

3. A compound according to claim 1, wherein R$^3$ and R$^4$ each independently represent a hydrogen atom, or a 4-piperidinyl, C$_3$–C$_6$ cycloalkyl or C$_1$–C$_6$ alkyl group, which latter two groups is optionally substituted by one, two, three or four substituent groups independently selected from halogen atoms and —NR$^5$R$^6$, —CONR$^5$R$^6$, —OR$^7$—COOR$^7$, —NR$^8$COR$^9$, —SR$^{10}$, —SO$_2$R$^{10}$, —SO$_2$NR$^5$R$^6$, —NR$^8$SO$_2$R$^9$, morpholinyl, C$_1$–C$_4$ alkyl, C$_3$–C$_6$ cycloalkyl, tetrahydrofuranyl and aryl groups, wherein an aryl substituent group is optionally a phenyl, naphthyl, thienyl, pyridinyl, imidazolyl or indolyl group, each of which is optionally substituted by one, two, three or four substituents independently selected from halogen atoms and cyano, nitro, —NR$^5$R$^6$, —CONR$^5$R$^6$—OR$^7$, —NR$^8$COR$^9$, —SO$_2$NR$^5$R$^6$, —NR$^8$SO$_2$R$^9$, C$_1$–C$_4$ alkyl and trifluoromethyl groups.

4. A compound according to claim 1, wherein R$^2$ represents a C$_1$–C$_6$ alkyl or C$_2$–C$_6$ alkenyl group optionally substituted by a phenyl or phenoxy group, wherein the phenyl or phenoxy group is itself be optionally substituted by one, two, three or four substituents independently selected from halogen atoms and nitro, C$_1$–C$_4$ alkyl, trifluoromethyl, —OR$^7$, —C(O)R$^7$, —SR$^{10}$, —NR$^{15}$R$^{16}$ and phenyl.

5. A compound according to claim 1, wherein X represents —NR$^{13}$R$^{14}$ and R$^{13}$ and R$^{14}$ each independently represent a hydrogen atom, a 4-piperidinyl group optionally substituted by a C$_1$–C$_4$ alkylphenyl substituent group, or a C$_3$–C$_7$ carbocyclic, C$_1$–C$_6$ alkyl, C$_2$–C$_6$ alkenyl or C$_2$–C$_6$ alkynyl group, which latter four groups is optionally substituted by one, two, three or four substituent groups independently selected from halogen atoms and —NR$^5$R$^6$, —CONR$^5$R$^6$, —OR$^7$, —COOR$^7$, —NR$^8$COR$^9$, —SR$^{10}$, —SO$_2$R$^{10}$, —SO$_2$NR$^5$R$^6$, —NR$^8$SO$_2$R$^9$, morpholinyl, C$_1$–C$_4$ alkyl, C$_3$–C$_6$ cycloalkyl and aryl groups, wherein an aryl substituent group is optionally a phenyl, naphthyl, thienyl, pyridinyl, imidazolyl or indolyl group, each of which is optionally substituted by one, two, three or four substituents independently selected from halogen atoms and cyano, nitro, —NR$^5$R$^6$, —CONR$^5$R$^6$, —OR$^7$, —NR$^8$COR$^9$, —SO$_2$NR$^5$R$^6$, NR$^8$SO$_2$R$^9$, C$_1$–C$_4$ alkyl and trifluoromethyl groups.

6. A compound according to claim 1 being selected from:
(2R)-2-[[2-Amino-5-[(phenylmethyl)thio]thiazolo[4,5-d]pyrimidin-7-yl]amino]-1-butanol, (S)-2-[[2-Amino-5-[(phenylmethyl)thio]thiazolo[4,5-d]pyrimidin-7-yl]amino]-1-butanol,
2-Amino-5-[[(2,3-difluorophenyl)methyl]thio]thiazolo[4,5-d]pyrimidin-7(4H)-one,
5-[[(3-Phenoxyphenyl)methyl]thio]thiazolo[4,5-d]pyrimidin-7(4H)-one,
2-Amino-5-[[(3-phenoxyphenyl)methyl]thio]thiazolo[4,5-d]pyrimidin-7(4H)-one,
(±)-2-[[2-Amino-5-(pentylthio)thiazolo[4,5-d]pyrimidin-7-yl]amino]-1-butanol,
2-[[2-Amino-5-(pentylthio)thiazolo[4,5-d]pyrimidin-7-yl]amino]ethanol,
5-(Pentylthio)thiazolo[4,5-d]pyrimidin-7(4H)-one,
2-Amino-5-[(phenylmethyl)thio]thiazolo[4,5-d]pyrimidin-7(4H)-one,
2-Amino-5-(pentylthio)thiazolo[4,5-d]pyrimidin-7(4H)-one,
2-[[3-(Dimethylamino)propyl]amino]-5-(pentylthio)thiazolo[4,5-d]pyrimidin-7(4H)-one,
2-[(2-(Diethylamino)ethyl]amino]-5-(pentylthio)thiazolo[4,5-d]pyrimidin-7(4H)-one,
2-[[2-(Dimethylamino)ethyl]amino]-5-(pentylthio)thiazolo[4,5-d]pyrimidin-7(4H)-one,
2-[(3-Hydroxypropyl)amino]-5-(pentylthio)thiazolo[4,5-d]pyrimidin-7(4H)-one,
2-[[2-(Acetylamino)ethyl]amino]-5-(pentylthio)thiazolo[4,5-d]pyrimidin-7(4H)-one,
(±)-2-[(2,3-Dihydoxypropyl)amino]-5-(pentylthio)thiazolo[4,5-d]pyrimidin-7(4H)-one,
2-[[2-(4-Morpholinyl)ethyl]amino]-5-(pentylthio)thiazolo[4,5-d]pyrimidin-7(4H)-one,
2-[(2-Methoxyethyl)amino]-5-(pentylthio)thiazolo[4,5-d]pyrimidin-7(4H)-one,
2-[(1-Methylethyl)amino]-5-(pentylthio)thiazolo[4,5-d]pyrimidin-7(4H)-one,
2-(Cyclopropylamino)-5-(pentylthio)thiazolo[4,5-d]pyrimidin-7(4H)-one,
(±)-2-[(2-Hydoxypropyl)amino]-5-(pentylthio)thiazolo[4,5-d]pyrimidin-7(4H)-one,
2-[[2-(2-Hydroxyethoxy)ethyl]amino]-5-(pentylthio)thiazolo[4,5-d]pyrimidin-7(4H)-one,
2-[(2-Hydroxy-2-methylpropyl)amino]-5-(pentylthio)thiazolo[4,5-d]pyrimidin-7(4H)-one,
2-[(2-Hydroxyethyl)amino]-5-(pentylthio)thiazolo[4,5-d]pyrimidin-7(4H)-one,
(2S,3R)-3-Hydroxy-2-[(7-oxo-5-(pentylthio)-4H-thiazolo[4,5-d]pyrimidin-2-yl]amino)butanamide, and their pharmaceutically acceptable salts and solvates.

7. A process for the preparation of a compound of formula (I) as defined in claim 1 which comprises:

(a) when X represents —OH and $R^1$ is $NH_2$, heating a compound of general formula

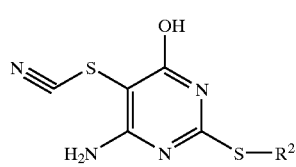
(II)

wherein $R^2$ is as defined in formula (I); or (b) when X represents —OH and $R^1$ is $NH_2$, reacting a compound of formula

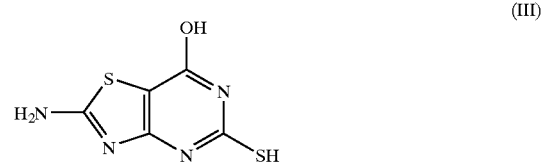
(III)

with a compound of general formula (IV), $R^2—L^1$, wherein $L^1$ represents a leaving group and $R^2$ is as defined in formula (I); or (c) when X represents —OH or —$NR^{13}R^{14}$ and $R^1$ is a hydrogen atom, reacting a corresponding compound of formula (I) in which $R^1$ is $NH_2$, with a diazotizing agent; or (d) when X represents —OH and $R^1$ is a group —$NR^3R^4$, reacting a compound of general formula

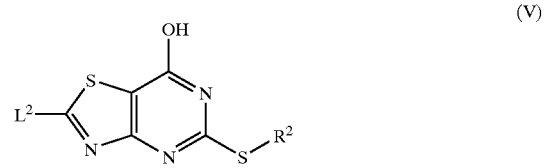
(V)

wherein $L^2$ represents a leaving group and $R^2$ is as defined in formula (I), with a compound of general formula (VI), $R^3R^4NH$, wherein $R^3$ and $R^4$ are as defined in formula (1); or (e) when X represents —$NR^{13}R^{14}$ and $R^1$ represents —$NR^3R^4$, reacting a compound of general formula

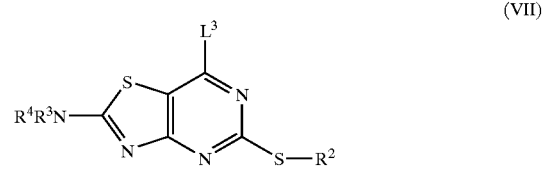
(VII)

wherein $L^3$ represents a leaving group and $R^2$, $R^3$ and $R^4$ are as defined in formula (I), with a compound of general formula (VIII), $NHR^{13}R^{14}$, wherein $R^{13}$ and $R^{14}$ are as defined in formula (I); or (f) when X represents —$NR^{13}R^{14}$ and $R^1$ represents —$NR^3R^4$, reacting a compound of general formula

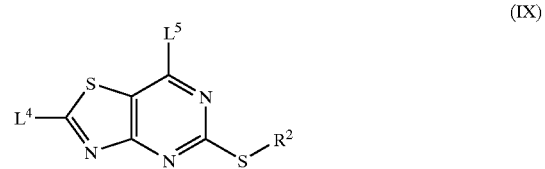
(IX)

wherein $L^4$ is a leaving group, $L^5$ is a leaving group and $R^2$ is as defined in formula (I), initially with a compound of formula (VI) as defined in (d) above followed by reaction with a compound of formula (VIII) as defined in (e) above;

and optionally after (a), (b), (c), (d), (e) or (f) forming a pharmaceutically acceptable salt or solvate of the compound of formula (I).

8. An intermediate compound of formula (V);

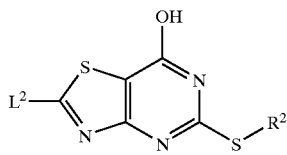

(V)

wherein $L^2$ represents halogen and $R^2$ represents a $C_1$–$C_6$ alkyl or $C_2$–$C_6$ alkenyl group optionally substituted by a phenyl or phenoxy group, wherein the phenyl or phenoxy group is itself optionally substituted by one or more substituents independently selected from halogen atoms and nitro, $C_1$–$C_6$ alkyl, trifluoromethyl, —$OR^7$, $C(O)R^7$, —$SR^{10}$, —$NR^{15}R^{16}$ and phenyl groups, wherein $R^7$ is a hydrogen atom or a $C_1$–$C_6$ alkyl or phenyl group which is optionally substituted by one or more substituent groups independently selected from halogen atoms, phenyl, —$OR^{17}$ and —$NR^{15}R^{16}$, wherein each of $R^{10}$, $R^{15}$, $R^{16}$, and $R^{17}$ independently represent a hydrogen atom or a $C_1$–$C_6$ alkyl or phenyl group.

9. An intermediate compound of formula (VII)

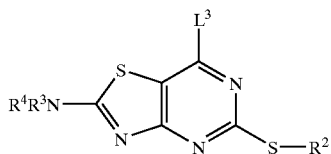

(VII)

wherein $L^3$ represents hydrogen, $R^2$ represents a $C_1$–$C_6$ alkyl or $C_2$–$C_6$ alkenyl group optionally substituted by a phenyl or phenoxy group, wherein the phenyl or phenoxy group is itself optionally substituted by one or more substituents independently selected from halogen atoms and nitro, $C_1$–$C_6$ alkyl, trifluoromethyl, —$OR^7$, $C(O)R^7$, —$SR^{10}$, —$NR^{15}R^{16}$ and phenyl groups, wherein $R^7$ is a hydrogen atom or a $C_1$–$C_6$ alkyl or phenyl group which is optionally substituted by one or more substituent groups independently selected from halogen atoms, phenyl, —$OR^{17}$ and —$NR^{15}R^{16}$, wherein each of $R^{10}$, $R^{15}$, $R^{16}$, and $R^{17}$ independently represent a hydrogen atom or a $C_1$–$C_6$ alkyl or phenyl group, and $R^3$ and $R^4$ each independently represent a hydrogen atom, or a 4-piperidinyl, $C_3$–$C_6$ cycloalkyl or $C_1$–$C_8$ alkyl group, which latter two groups are optionally substituted by one or more substituent groups independently selected from halogen atoms and —$NR^5R^6$, —$CONR^5R^6$, —$OR^7$, —$COOR^7$, —$NR^8COR^9$, —$SR^{10}$, —$SO_2R^{10}$, —$SO_2NR^5R^6$, —$NR^8SO_2R^9$, morpholinyl, $C_1$–$C_4$ alkyl, $C_3$–$C_6$ cycloalkyl, tetrahydrofuranyl and aryl groups, wherein an aryl substituent group may be a phenyl, naphthyl, thienyl, pyridinyl, imidazolyl or indolyl group, each of which may be optionally substituted by one or more substituents independently selected from halogen atoms and cyano, nitro, —$NR^5R^6$, —$CONR^5R^6$, —$OR^7$, —$NR^8COR^9$, —$SO_2NR^5R^6$, —$NR^8SO_2R^9$, $C_1$–$C_6$ alkyl and trifluoromethyl groups, or $R^3$ and $R^4$ together with the nitrogen atom to which they are attached form a 4- to 7-membered saturated heterocyclic ring system, which ring system is optionally substituted by one or more substituent groups independently selected from

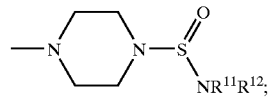

—$NR^5R^6$, —$CONR^5R^6$, —$OR^7$, —$COOR^{10}$, —$NR^8COR^9$, and $C_1$–$C_6$ alkyl optionally substituted by one or more substituents independently selected from halogen atoms and —$NR^{11}R^{12}$ and —$OR^7$ groups;

X represents a group —OH or —$NR^{13}R^{14}$;

$R^{13}$ and $R^{14}$ each independently represent a hydrogen atom, a 4-piperidinyl group optionally substituted by a $C_1$–$C_4$ alkylphenyl substituent group, or a $C_3$–$C_7$ carbocyclic, $C_1$–$C_8$ alkyl, $C_2$–$C_6$ alkenyl or $C_2$–$C_6$ alkynyl group, which latter four groups are optionally substituted by one or more substituent groups independently selected from halogen atoms and —$NR^5R^6$, —$CONR^5R^6$, —$OR^7$, —$COOR^7$, —$NR^8COR^9$, —$SR^{10}$, —$SO_2R^{10}$, —$SO_2NR^{15}R^6$, —$NR^8SO_2R^9$, morpholinyl, $C_1$–$C_4$ alkyl, $C_3$–$C_6$ cycloalkyl aryl groups, wherein an aryl substituent group is optionally a phenyl, naphthyl, thienyl, pyridinyl, imidazolyl or indolyl group, each of which is optionally substituted by one or more substituents independently selected from halogen atoms and cyano, nitro, —$NR^5R^6$, —$CONR^5R^6$, —$OR^7$, —$NR^8COR^9$, —$SO_2NR^5R^6$, $NR^8SO_2R^9$, $C_1$–$C_6$ alkyl and trifluoromethyl groups, or $R^{13}$ and $R^{14}$ together with the nitrogen atom to which they are attached form a 4- to 7-membered saturated heterocyclic ring system, which ring system is optionally substituted by one or more substituent groups independently selected from —$NR^5R^6$, —$CONR^5R^6$, —$OR^7$, —$COOR^7$, —$NR^8COR^9$, and $C_1$–$C_6$ alkyl optionally substituted by one or more substituents independently selected from halogen atoms and phenyl, —$NR^{11}R^{12}$ and —$OR^7$ groups.

10. An intermediate compound of formula (IX)

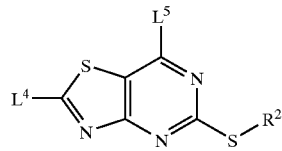

(IX)

wherein $L^4$ is halogen, $L^5$ is halogen and $R^2$ represents a $C_1$–$C_6$ alkyl or $C_2$–$C_6$ alkenyl group optionally substituted by a phenyl or phenoxy group, wherein the phenyl or phenoxy group is itself optionally substituted by one or more substituents independently selected from halogen atoms and nitro, $C_1$–$C_6$ alkyl, trifluoromethyl, —$OR^7$, $C(O)R^7$, —$SR^{10}$, —$NR^{15}R^{16}$ and phenyl groups, wherein $R^7$ is a hydrogen atom or a $C_1$–$C_6$ alkyl or phenyl group which is optionally substituted by one or more substituent groups independently selected from halogen atoms, phenyl, —$OR^{17}$ and —$NR^{15}R^{16}$, wherein each of $R^{10}$, $R^{15}$, $R^{16}$, and $R^{17}$ independently represent a hydrogen atom or a $C_1$–$C_6$ alkyl or phenyl group.

11. A pharmaceutical composition comprising a compound of formula (I), or a pharmaceutically acceptable salt or solvate thereof, as claimed in claim 1 in association with a pharmaceutically acceptable adjuvant, diluent or carrier.

12. A process for the preparation of a pharmaceutical composition comprising a compound of formula (I), or a pharmaceutically acceptable salt or solvate thereof, as claimed in claim 1 in association with a pharmaceutically acceptable adjuvant, diluent or carrier, which comprises mixing a compound of formula (I), or a pharmaceutically acceptable salt or solvate thereof, as claimed in claim 1 with a pharmaceutically acceptable adjuvant, diluent or carrier.

13. A method of treating a gastrointestinal tract disease, which comprises administering to a patent a therapeutically effective amount of a compound of formula (I), or a pharmaceutically acceptable salt or solvate thereof, as claimed in claim 1.

14. A method of treating an inflammatory disease in a patient suffering from, or at risk of, said disease, which comprises administering to the patient a therapeutically effective amount of a compound of formula (I), or a pharmaceutically acceptable salt or solvate thereof, as claimed in claim 1.

15. A method according to claim 14, wherein the disease is psoriasis.

16. A compound according to claim 1 being selected from:
$N^7$-[3-(Diethylamino)ethyl]-5-(pentylthio)thiazolo[4,5-d]pyrimidine-2,7-diamine,
$N^7$-[2-(Dimethylamino)ethyl]-5-(pentylthio)thiazolo[4,5-d]pyrimidine-2,7-diamine,
3-[(2-Amino-5-(pentylthio)thiazolo[4,5-d]pyrimidin-7-yl)amino]-1-propanol,
$N^7$-Cyclohexyl-5-(pentylthio)thiazolo[4,5-d]pyrimidine-2,7-diamine,
(±)-3-[(2-Amino-5-((phenylmethyl)thio)thiazolo[4,5-d]pyrimidin-7-yl)amino]-1,2-propanediol,
$N^7$-(2-Methoxyethyl)-5-(pentylthio)thiazolo[4,5-d]pyrimidine-2,7-diamine,
5-(Pentylthio)-$N^7$-propylthiazolo[4,5-d]pyrimidine-2,7-diamine,
$N^7$-Cyclopentyl-5-(pentylthio)thiazolo[4,5-d]pyrimidine-2,7-diamine,
$N^7$-Cyclopropyl-5-(pentylthio)thiazolo[4,5-d]pyrimidine-2,7-diamine,
$N^7$-(2-Methylpropyl)-5-(pentylthio)thiazolo[4,5-d]pyrimidine-2,7-diamine,
(±)-1-[(2-Amino-5-(pentylthio)thiazolo[4,5-d]pyrimidin-7-yl)amino]-2-propanol,
(exo)-$N^7$-Bicyclo[2.2.1]hept-2-yl-5-(pentylthio)thiazolo[4,5-d]pyrimidine-2,7-diamine,
2-[2-[[2-Amino-5-(pentylthio)thiazolo[4,5-d]pyrimidin-7-yl]amino]ethoxy]ethanol,
(±)-$N^7$-(2-Methylbutyl)-5-(pentylthio)thiazolo[4,5-d]pyrimidine-2,7-diamine,
1-[[2-Amino-5-(pentylthio)thiazolo[4,5-d]pyrimidin-7-yl]amino]-2-methyl-2-propanol,
$N^7$-[(2-Aminophenyl)methyl]-5-(pentylthio)thiazolo[4,5-d]pyrimidine-2,7-diamine,
2-Amino-5-[(2-phenoxyethyl)thio]thiazolo[4,5-d]pyrimidin-7(4H)-one,
(E)-2-Amino-5-((3-phenyl-2-propenyl)thio)thiazolo[4,5-d]pyrimidin-7(4H)-one,
2-Amino-5-[(3-[2,4-bis(1,1-dimethylethyl)phenoxy]propyl]thio]thiazolo[4,5-d]pyrimidin-7(4H)-one, and their pharmaceutically acceptable salts and solvates.

17. A compound according to claim 1 being selected from:
2-Amino-5-[[(3,5-dichlorophenyl)methyl]thio]thiazolo[4,5-d]pyrimidin-7(4H)-one,
2-Amino-5-[[(2,4-dichlorophenyl)methyl]thio]thiazolo[4,5-d]pyrimidin-7(4H)-one,
2-Amino-5-[[(3,4-dichlorophenyl)methyl]thio]thiazolo[4,5-d]pyrimidin-7(4H)-one,
2-Amino-5-[[(3,5-dibromophenyl)methyl]thio]thiazolo[4,5-d]pyrimidin-7(4H)-one,
2-Amino-5-[[(2-nitrophenyl)methyl]thio]thiazolo[4,5-d]pyrimidin-7(4H)-one,
2-Amino-5-[[(2-fluorophenyl)methyl]thio]thiazolo[4,5-d]pyrimidin-7(4H)-one,
2-Amino-5-[[(2-iodophenyl)methyl]thio]thiazolo[4,5-d]pyrimidin-7(4H)-one,
2-Amino-5-[[(3-chlorophenyl)methyl]thio]thiazolo[4,5-d]pyrimidin-7(4H)-one,
2-Amino-5-[[(2-chlorophenyl)methyl]thio]thiazolo[4,5-d]pyrimidin-7(4H)-one,
2-Amino-5-[[(4-chloro-2-nitrophenyl)methyl]thio]thiazolo[4,5-d]pyrimidin-7(4H)-one,
2-Amino-5-[[(3-chloro-4-methoxyphenyl)methyl]thio]thiazolo[4,5-d]pyrimidin-7(4H)-one,
2-Amino-5-[[(2,3-dichlorophenyl)methyl]thio]thiazolo[4,5-d]pyrimidin-7(4H)-one,
2-Amino-5-[[(3,5-difluorophenyl)methyl]thio]thiazolo[4,5-d]pyrimidin-7(4)-one,
2-Amino-5-[[[(2,4-bis(trifluoromethyl)phenyl]methyl]thio]thiazolo[4,5-d]pyrimidin-7(4H)-one,
2-Amino-5-[[(2-bromophonyl)methyl]thio]thiazolo[4,5-d]pyrimidin-7(4H)-one,
2-Amino-5-[[(2,3,4-trifluorophenyl)methyl]thio]thiazolo[4,5-d]pyrimidin-7(4H)-one,
and their pharmaceutically acceptable salts and solvates.

18. A compound according to claim 1 being selected from:
2-Amino-5-[[(3-bromophenyl)methyl]thio]thiazolo[4,5-d]pyrimidin-7(4H)-one,
2-Amino-5-[[(2-fluoro-3-methylphenyl)methyl]thio]thiazolo[4,5-d]pyrimidin-7(4H)-one,
3-[[2-Amino-5-[(phenylmethyl)thio]thiazolo[4,5-d]pyrimidin-7-yl]amino]-2,2-dimethyl-1-propanol,
(±)-α-[[[2-Amino-5-[(phenylmethyl)thio]thiazolo[4,5-d]pyrimidin-7-yl]amino]methyl]benzenemethanol,
(R)-β-[[2-Amino-5-[(phenylmethyl)thio]thiazolo[4,5-d]pyrimidin-7-yl]amino]benzenepropanol,
2-[[2-Amino-5-[(phenylmethyl)thio]thiazolo[4,5-d]pyrimidin-7-yl]amino]ethanol,
(2R)-2-[[2-Amino-5-[(phenylmethyl)thio]thiazolo[4,5-d]pyrimidin-7-yl]amino]-4-methylpentanol,
(±)-1-[[2-Amino-5-[(phenylmethyl)thio]thiazolo[4,5-d]pyrimidin-7-yl]amino]-2-propanol,
(±)-β-[[2-Amino-5-[(phenylmethyl)thio]thiazolo[4,5-d]pyrimidin-7-yl]amino]-4-chlorobenzenepropanol,
(±)-3-[[2-Amino-5-[(phenylmethyl)thio]thiazolo[4,5-d]pyrimidin-7-yl]amino]-1,2-propanediol,
2-[[2-Amino-5-[(phenylmethyl)thio]thiazolo[4,5-d]pyrimidin-7-yl]propylamino]ethanol,
(±)-1-[2-Amino-5-[(phenylmethyl)thio]thiazolo[4,5-d]pyrimidin-7-yl]-3-pyrrolidinol,
(±)-1-[2-Amino-5-[(phenylmethyl)thio]thiazolo[4,5-d]pyrimidin-7-yl]-3-piperidinol,
and their pharmaceutically acceptable salts and solvates.

19. A compound according to claim 1 being selected from:
1-[2-Amino-5-[(phenylmethyl)thio]thiazolo[4,5-d]pyrimidin-7-yl]-4-piperidinol, 3-[[2-Amino-5-[[(3-phenoxyphenyl)methyl]thio]thiazolo[4,5-d]pyrimidin-7-yl]amino]-2,2-dimethyl-1-propanol, (±)-2-[[2-Amino-5-[[(3-phenoxyphenyl)methyl]thio]thiazolo[4,5-d]pyrimidin-7-yl]amino]butanol, (±)-α1-[[[2-Amino-5-[[(3-phenoxyphenyl)methyl]thio]thiazolo[4,5-d]pyrimidin-7-yl]amino]methyl]benzenemethanol, 4-[[2-Amino-5-[[(3-phenoxyphenyl)methyl]thio]thiazolo[4,5-d]pyrimidin-7-yl]amino]-1-butanol, 6-[[2-Amino-5-[[(3-phenoxyphenyl)methyl]thio]thiazolo[4,5-d]pyrimidin-7-yl]amino]-1-hexanol, 4-[[2-Amino-5-[[(3-phenoxyphenyl)methyl]thio]thiazolo[4,5-d]pyrimidin-7-yl]amino]cyclohexanol, (R)-β-[[2-Amino-5-[[(3-phenoxypheny)methyl]thio]thiazolo[4,5-d]pyrimidin-7-yl]amino]benzenepropanol, (±)-2-[[2-Amino-5-[[(3-phenoxyphenyl)methyl]thio]thiazolo[4,5-d]pyrimidin-7-yl]amino]-1-propanol, 2-[[2-Amino-5-[[(3-phenoxyphenyl)methyl]thio]thiazolo[4,5-d]pyrimidin-7-yl]amino]ethanol, (2R)-2-[[2-Amino-5-[[(3-phenoxyphenyl)methyl]thio]thiazolo[4,5-d]pyrimidin-7-yl]-amino]-4-methylpentanol, and their pharmaceutically acceptable salts and solvates.

20. A compound according to claim 1 being selected from:

(±)-1-Amino-3-[[2-Amino-5-[[(3-phenoxyphenyl)methyl]thio]thiazolo[4,5-d]pyrimidin-7-yl]amino]-2-propanol, (±)-1-[[2-Amino-5-[[(3-phenoxyphenyl)methyl]thio]thiazolo[4,5-d]pyrimidin-7-yl]amino]-2-propanol, 2-[[[2-Amino-5-[[(3-phenoxyphenyl)methyl]thio]thiazolo[4,5-d]pyrimidin-7-yl]amino]methyl]-2-ethyl-1,3-propanediol, (±)-β-[[2-Amino-5-[[(3-phenoxyphenyl)methyl]thio]thiazolo[4,5-d]pyrimidin-7-yl]amino]-4-chlorobenzenepropanol, (±)-3-[[2-Amino-5-[[(3-phenoxyphenyl)methyl]thio]thiazolo[4,5-d]pyrimidin-7-yl]amino]-1,2-propanediol, 2-[[2-[[2-Amino-5-[[(3-phenoxyphenyl)methyl]thio]thiazolo[4,5-d]pyrimidin-7-yl]amino]ethyl]amino]ethanol, 3-[[2-Amino-5-[[(3-phenoxyphenyl)methyl]thio]thiazolo[4,5-d]pyrimidin-7-yl]amino]-1-propanol, (±)-α-[[[2-Amino-5-[[(3-phenoxyphenyl)methyl]thio]thiazolo[4,5-d]pyrimidin-7-yl]amino]methyl]-3,4-dichlorobenzenepropanol, 1-[[2-Amino-5-[[(3-phenoxyphenyl)methyl]thio]thiazolo[4,5-d]pyrimidin-7-yl]amino]-2-methyl-2-propanol, 2-[2-[[2-Amino-5-[[(3-phenoxyphenyl)methyl]thio]thiazolo[4,5-d]pyrimidin-7-yl]amino]ethoxy]ethanol, 5-[[2-Amino-5-[[(3-phenoxyphenyl)methyl]thio]thiazolo[4,5-d]pyrimidin-7-yl]amino]-1-pentanol, and their pharmaceutically acceptable salts and solvates.

21. A compound according to claim 1 being selected from:

(2S)-2-[[2-Amino-5-[[(3-phenoxyphenyl)methyl]thio]thiazolo[4,5-d]pyrimidin-7-yl]amino]-4-(methylthio)-1-butanol, 2-[[2-Amino-5-[[(3-phenoxyphenyl)methyl]thio]thiazolo[4,5-d]pyrimidin-7-yl]butylamino]ethanol, 2-[[2-Amino-5-[[(3-phenoxyphenyl)methyl]thio]thiazolo[4,5-d]pyrimidin-7-yl]propylamino]ethanol, 2,2'-[[2-Amino-5-[[(3-phonoxyphenyl)methyl]thio]thiazolo[4,5-d]pyrimidin-7-yl]imino]bisethanol, 2-[[[2-Amino-5-[[(3-phenoxyphenyl)methyl]thio]thiazolo[4,5-d]pyrimidin-7-yl]-(2-hydroxyethyl)amino]methyl]phenol, 3-[[2-Amino-5-[[(3-phenoxyphenyl)methyl]thio]thiazolo[4,5-d]pyrimidin-7-yl]-(2-hydroxyethyl)amino]-1-propanol, (±)-1-[2-Amino-5-[[(3-phenoxyphenyl)methyl]thio]thiazolo[4,5-d]pyrimidin-7-yl]-3-pyrrolidinol, (trans)-1-[2-Amino-5-[[(3-phenoxyphenyl)methyl]thio]thiazolo[4,5-d]pyrimidin-7-yl]-4-hydroxy-L-proline phenylmethyl ester, (±)-1-[2-Amino-5-[[(3-phenoxyphenyl)methyl]thio]thiazolo[4,5-d]pyrimidin-7-yl]-3-piperidinemethanol, (±)-1-[2-Amino-5-[[(3-phenoxyphenyl)methyl]thio]thiazolo[4,5-d]pyrimidin-7-yl]-3-piperidinol, and their pharmaceutically acceptable salts and solvates.

22. A compound according to claim 1 being selected from:

(2S)-1-[2-Amino-5-[[(3-phenoxyphenyl)methyl]thio]thiazolo[4,5-d]pyrimidin-7-yl]-2-pyrrolidinemethanol, 1-[2-Amino-5-[[(3-phenoxyphenyl)methyl]thio]thiazolo[4,5-d]pyrimidin-7-yl]-4-piperidinol, (2R)-2-[[2-Amino-5-[[(3-phenoxyphenyl)methyl]thio]thiazolo[4,5-d]pyrimidin-7-yl]amino]-1-butanol, (2S)-2-[[2-Amino-5-[[(3-phenoxyphenyl)methyl]thio]thiazolo[4,5-d]pyrimidin-7-yl]amino]-1-butanol, (2R)-2-[[2-Amino-5-[[(2,3-difluorophenyl)methyl]thio]thiazolo[4,5-d]pyrimidin-7-yl]amino]-1-butanol, 2-[[2-Amino-5-[[(3-phenoxyphenyl)methyl]thio]thiazolo[4,5-d]pyrimidin-7-yl]amino]-1,3-propanediol, 2-[[2-Amino-5-[[(3-phenoxyphenyl)methyl]thio]thiazolo[4,5-d]pyrimidin-7-yl]amino]-2-methyl-1-propanol, 2-[[2-Amino-5-[[(2,3-difluorophenyl)methyl]thio]thiazolo[4,5-d]pyrimidin-7-yl]amino]-2-methyl-1-propanol, 1-[[2-Amino-5-[[(2,3-difluorophenyl)methyl]thio]thiazolo[4,5-d]pyrimidin-7-yl]amino]-2-methyl-2-propanol, 5-[[(2,3-Difluorophenyl)methyl]thio]-W-(2-fluoroethyl)thiazolo[4,5-d]pyrimidine-2,7-diamine, (1R-trans) 2-[[2-Amino-5-[[(2,3-difluorophenyl)methyl]thio]thiazolo[4,5-d]pyrimidin-7-yl]amino]-cyclopentanol, and their pharmaceutically acceptable salts and solvates.

23. A compound according to claim 1 being selected from:

(1S-trans) 2-[[2-Amino-5-[[(2,3-difluorophenyl)methyl]thio]thiazolo[4,5-d]pyrimidin-7-yl]amino]-cyclopentanol, 2-[[2-Amino-5-[(phenylmethyl)thio]thiazolo[4,5-d]pyrimidin-7-yl]amino]-2-methyl-1-propanol, 2-Methyl-2-[[2-(methylamino)-5-[(phenylmethyl)thio]thiazolo[4,5-d]pyrimidin-7-yl]amino]-1-propanol, 2-[[2-[[5-[((2,3-Difluorophenyl)methyl]thio]-2-[(phenylmethyl)amino]thiazolo[4,5-d]pyrimidin-7-yl]amino]-2-methyl-1-propanol, 5-[[(2,3-Difluorophenyl)methyl]thio]thiazolo[4,5-d]pyrimidin-7(4H)-one, (±)-2-[[2-Amino-5-[[(2,3-difluorophenyl)methyl]thio]thiazolo[4,5-d]pyrimidin-7-yl]amino]-1-butanol, (1S,2S)-2-[[2-Amino-5-[[(2,3-difluorophenyl)methyl]thio]thiazolo[4,5-d]pyrimidin-7-yl]amino]-cyclohexanol, (±)-2-[[2-Amino-5-[((2,3-difluorophenyl)methyl]thio]thiazolo[4,5-d]pyrimidin-7-yl]amino]-1-propanol, 2-[[2-Amino-5-[[(2,3-difluorophenyl)methyl]thio]
thiazolo[4,5-d]pyrimidin-7-yl]amino]-1-ethanol, (2R)-2-[[2-Amino-5-[[(2,3-difluorophenyl)methyl]thio]
thiazolo[4,5-d]pyrimidin-7-yl]amino]-4-methyl-1-pentanol, (±)-1-[[2-Amino-5-[[(2,3-difluorophenyl)methyl]thio]
thiazolo[4,5-d]pyrimidin-7-yl]amino]-2-propanol, and
their pharmaceutically acceptable salts and solvates.

24. A compound according to claim 1 being selected from:

2-[[2-Amino-5-[[(2,3-difluorophenyl)methyl]thio]
thiazolo[4,5-d]pyrimidin-7-yl]amino]-2-methyl-1,3-propanediol, 1-[[[2-Amino-5-[[(2,3-difluorophenyl)methyl]thio]
thiazolo[4,5-d]pyrimidin-7-yl]amino]methyl]-cyclohexanol, (2R)-2-[[2-Amino-5-[[(2,3-difluorophenyl)methyl]thio]
thiazolo[4,5-d]pyrimidin-7-yl]amino]-1-butanol, 2-[[2-Amino-5-[[(2,3-difluorophenyl)methyl]thio]
thiazolo[4,5-d]pyrimidin-7-yl]-(2-aminoethyl)amino]-1-ethanol, 2-[2-[[2-Amino-5-[[(2,3-difluorophenyl)methyl]thio]
thiazolo[4,5-d]pyrimidin-7-yl]amino]ethoxy]-1-ethanol, (αS)-α-[(1R)-1-[[2-Amino-5-[[(2,3-difluorophenyl)
methyl]thio]thiazolo[4,5-d]pyrimidin-7-yl]
methylamino]ethyl]-benzenemethanol, 1-[2-Amino-5-[[(2,3-difluorophenyl)methyl]thio]
thiazolo[4,5-d]pyrimidin-7-yl]-4-piperidinol, 5-[[(2,3-Difluorophenyl)methyl]thio]-$N^7$-ethyl-thiazolo
[4,5-d]pyrimidine-2,7-diamine, 5-[[(2,3-Difluorophenyl)methyl]thio]-$N^7$-(2-propenyl)-
thiazolo[4,5-d]pyrimidine-2,7-diamine, (1S,2S)-2-[[2-Amino-5-[[(2,3-difluorophenyl)methyl]
thio]thiazolo[4,5-d]pyrimidin-7-yl]amino]-1-phenyl-1,3-propanediol, 2-[[2-Amino-5-[[(2,3-difluorophonyl)methyl]thio]
thiazolo[4,5-d]pyrimidin-7-yl]amino]-1,3-propanediol,
and their pharmaceutically acceptable salts and solvates.

25. A compound according to claim 1 being selected from:

2-[[2-Amino-5-[[(2,3-difluorophenyl)methyl]thio]
thiazolo[4,5-d]pyrimidin-7-yl]amino]-1-ethanol, (±)-5-[[(2,3-Difluorophenyl)methyl]thio]-$N^7$-(2-methoxy-1-methylethyl)-thiazolo[4,5-d]pyrimidine-2,7-diamine, $N^7$-Cyclopropyl-5-[[(2,3-difluorophenyl)methyl]thio]-
thiazolo[4,5-d]pyrimidine-2,7-diamine, (±)-2-[[2-Amino-5-[[(2,3-difluorophenyl)methyl]thio)-
thiazolo[4,5-d]pyrimidin-7-yl]amino]-1-propanol, 4-[[(2-Amino-5-[[(2,3-difluorophenyl)methyl]thio]-
thiazolo[4,5-d]pyrimidin-7-yl]amino]-1-butanol, 5-[[(2,3-Difluorophenyl)methyl]thio]-$N^7$-[2-(Imidazol-4-yl)ethyl]-thiazolo[4,5-d]pyrimidine-2,7-diamine, (±)-N-[5-[[(2,3-Difluorophenyl)methyl]thio]-7-[(2-hydroxy-1,1-dimethylethyl)amino]thiazolo[4,5-d]
pyrimidin-2-yl]-serine, methyl ester, 2-[[5-[[(2,3-Difluorophenyl)methyl]thio]-2-[(1-methylethyl)amino]thiazolo[4,5-d]pyrimidin-7-yl]
amino]-2-methyl-1-propanol, 2-[(5-[[(2,3-Difluorophenyl)methyl]thio]-2-(ethylamino)
thiazolo[4,5-d]pyrimidin-7-yl]amino]-2-methyl-1-propanol, 2-[[5-[[(2,3-Difluorophenyl)methyl]thio]-2-[[2-(1H-indol-3-yl)ethyl]amino]thiazolo[4,5-d]pyrimidin-7-yl]
amino]-2-methyl-1-propanol, and their pharmaceutically acceptable salts and solvates.

26. A compound according to claim 1 being selected from:

2-[(5-[[(2,3-Difluorophenyl)methyl]thio]-2-[(1-naphthalenylmethyl)amino]thiazolo[4,5-d]pyrimidin-7-yl]amino]-2-methyl-1-propanol, 2-[[5-[[(2,3-Difluorophenyl)methyl]thio]-2-[(1,2-diphenylethyl)amino]thiazolo[4,5-d]pyrimidin-7-yl]
amino]-2-methyl-1-propanol, 2-[[5-[[(2,3-Difluorophenyl)methyl]thio]-2-[(2,2,2-trifluoroethyl)amino]thiazolo[4,5-d]pyrimidin-7-yl]
amino]-2-methyl-1-propanol, 2-[[5-[[(2,3-Difluorophenyl)methyl]thio]-2-[[(3,4,5-trimethoxyphenyl)methyl]amino]thiazolo[4,5-d]
pyrimidin-7-yl]amino]-2-methyl-1-propanol, 2-[[5-[[(2,3-Difluorophenyl)methyl]thio]-2-[(1,1-dimethylethyl)amino]thiazolo[4,5-d]pyrimidin-7-yl]
amino]-2-methyl-1-propanol, 2-[[5-[[(2,3-Difluorophenyl)methyl]thio]-2-[[2-(2-thienyl)ethyl]amino]thiazolo[4,5-d]pyrimidin-7-yl]
amino]-2-methyl-1-propanol, 2-[[5-[[(2,3-Difluorophenyl)methyl]thio]-2-[(4-methylcyclohexyl)amino]thiazolo[4,5-d]pyrimidin-7-yl]amino]-2-methyl-1-propanol, 2-[[5-[[(2,3-Difluorophenyl)methyl]thio]-7-[(2-hydroxy-1,1-dimethylethyl)amino]thiazolo[4,5-d]pyrimidin-2-yl]amino]-acetamide, 2-[[2-[[2-(4-Aminophenyl)ethyl]amino]-5-[[(2,3-difluorophenyl)methyl]thio]thiazolo[4,5-d]pyrimidin-7-yl]amino]-2-methyl-1-propanol, and their pharmaceutically acceptable salts and solvates.

27. A compound according to claim 1 being selected from:

2-[[5-[[2,3-Difluorophenyl)methyl]thio]-2-[(2-fluoroethyl)amino]thiazolo[4,5-d]pyrimidin-7-yl]
amino]-2-methyl-1-propanol, 2-[[2-(Cyclopropylamino)-5-[[(2,3-difluorophenyl)
methyl]thio]thiazolo[4,5-d]pyrimidin-7-yl]amino]-2-methyl-1-propanol, (±)-2-[[5-[[(2,3-Difluorophenyl)methyl]thio]-7-[(2-hydroxy-1,1-dimethylethyl)amino]thiazolo[4,5-d]
pyrimidin-2-yl]amino]-1-pentanol, 2-[[5-[[(2,3-Difluorophenyl)methyl]thio]-2-[[2-(2-hydroxyethoxy)ethyl]amino]thiazolo[4,5-d]pyrimidin-7-yl]amino]-2-methyl-1-propanol, N-[5-[[(2,3-Difluorophenyl)methyl]thio]-6,7-dihydro-7-oxo-thiazolo[4,5-d]pyrimidin-2-yl]-DL-serine, methyl ester, 5-[[(2,3-Difluorophenyl)methyl]thio]-2-[(1-methylethyl)
amino]-thiazolo[4,5-d]pyrimidin-7(4H)-one, 5-[[(2,3-Difluorophenyl)methyl]thio]-2-[[2-(1H-indol-3-yl)ethyl]amino]-thiazolo[4,5-d]pyrimidin-7(4H)-one, 2-[[5-[[(2,3-Difluorophenyl)methyl]thio]-6,7-dihydro-7-oxo-thiazolo[4,5-d]pyrimidin-2-yl]amino]-acetamide, 2-[[2-(4-Aminophenyl)ethyl]amino]-5-[[(2,3-difluorophenyl)methyl]thio-thiazolo[4,5-d]pyrimidin-7(4H)-one, 5-[[(2,3-Difluorophenyl)methyl]thio]-2-[(2-fluoroethyl)
amino]-thiazolo[4,5-d]pyrimidin-7(4H)-one, 5-[[(2,3-Difluorophenyl)methyl]thio]-2-[[2-(2-hydroxyethoxy)ethyl]amino]-thiazolo[4,5-d]
pyrimidin-7(4H)-one, 2-[[2-(Cyclohexylamino)-5-[(phenylmethyl)thio]thiazolo
[4,5-d]pyrimidin-7-yl]amino]-2-methyl-1-propanol,
and their pharmaceutically acceptable salts and solvates.

28. A compound according to claim 1 being selected from:

2-[[2-[(1,1-Dimethylethyl)amino]-5-[(phenylmethyl) thio]thiazolo[4,5-d]pyrimidin-7-yl]amino]-2-methyl-1-propanol, N-[7-[(2-Hydroxy-1,1-dimethylethyl)amino]-5-[(phenylmethyl)thio]thiazolo[4,5-d]pyrimidin-2-yl]-DL-alanine, methyl ester, 4-[[7-[(2-Hydroxy-1,1-dimethylethyl)amino]-5-[(phenylmethyl)thio]thiazolo[4,5-d]pyrimidin-2-yl]amino]-cyclohexanol, 2-Methyl-2-[[2-[(4-phenylbutyl)amino]-5-[(phenylmethyl)thio]thiazolo[4,5-d]pyrimidin-7-yl]amino]-1-propanol, 2-Methyl-2-[[5-[(phenylmethyl)thio]-2-[[(tetrahydro-2-furanyl)methyl]amino]thiazolo[4,5-d]pyrimidin-7-yl]amino]-1-propanol, 2-Methyl-2-[[2-[(1-methylethyl)amino]-5-[(phenylmethyl)thio]thiazolo[4,5-d]pyrimidin-7-yl]amino]-1-propanol, 2-[[2-[[2-(4-Aminophenyl)ethyl]amino]-5-[(phenylmethyl)thio]thiazolo[4,5-d]pyrimidin-7-yl]amino]-2-methyl-1-propanol, N-[7-[(2-Hydroxy-1,1-dimethylethyl)amino]-5-[(phenylmethyl)thio]thiazolo[4,5-d]pyrimidin-2-yl]-L-valine, ethyl ester, (2S)-2-[[7-[(2-Hydroxy-1,1-dimethylethyl)amino]-5-[(phenylmethyl)thio]thiazolo[4,5-d]pyrimidin-2-yl]amino]-4-methyl-pentanamide, 2-Methyl-2-[[2-[(2-phenylethyl)amino]-5-[(phenylmethyl)thio]thiazolo[4,5-d]pyrimidin-7-yl]amino]-1-propanol, 2-[[2-[[(4-Aminophenyl)methyl]amino]-5-[(phenylmethyl)thio]thiazolo[4,5-d]pyrimidin-7-yl]amino]-2-methyl-1-propanol, and their pharmaceutically acceptable salts and solvates.

29. A compound according to claim 1 being selected from:

2-Methyl-2-[[5-[(phenylmethyl)thio]-2-[[2-(2-thienyl)ethyl]amino]thiazolo[4,5-d]pyrimidin-7-yl]amino]-1-propanol, 2-[[2-[(2-Fluoroethyl)amino]-5-[(phenylmethyl)thio]thiazolo[4,5-d]pyrimidin-7-yl]amino]-2-methyl-1-propanol, 2-Methyl-2-[[2-[[(3-nitrophenyl)methyl]amino]-5-[(phenylmethyl)thio]thiazolo[4,5-d]pyrimidin-7-yl]amino]-1-propanol, ($\alpha$R)-$\alpha$-[(1S)-1-[[7-[(2-Hydroxy-1,1-dimethylethyl)amino]-5-[(phenylmethyl)thio]thiazolo[4,5-d]pyrimidin-2-yl]amino]ethyl]-benzenemethanol, 2-Methyl-2-[[5-[(phenylmethyl)thio]-2-[[(3,4,5-trimethoxyphenyl)methyl]amino]thiazolo[4,5-d]pyrimidin-7-yl]amino]-1-propanol, 2-Methyl-2-[[2-[(1R-trans)-(2-phenylcyclopropyl)amino]-5-[(phenylmethyl)thio]thiazolo[4,5-d]pyrimidin-7-yl]amino]-1-propanol, 2-[[2-[[2-(1H-indol-3-yl)ethyl]amino]-5-[(phenylmethyl)thio]thiazolo[4,5-d]pyrimidin-7-yl]amino]-2-methyl-1-propanol, 2-[[2-[(1,1-Dimethylpropyl)amino]-5-[(phenylmethyl)thio]thiazolo[4,5-d]pyrimidin-7-yl]amino]-2-methyl-1-propanol, ($\pm$)-2-Methyl-2-[[2-[(1-methylbutyl)amino]-5-[(phenylmethyl)thio]thiazolo[4,5-d]pyrimidin-7-yl]amino]-1-propanol, ($\pm$)-2-Methyl-2-[[2-[(1-methylhexyl)amino]-5-[(phenylmethyl)thio]thiazolo[4,5-d]pyrimidin-7-yl]amino]-1-propanol, 2-[[2-[[(2-Aminophenyl)methyl]amino]-5-[(phenylmethyl)thio]thiazolo[4,5-d]pyrimidin-7-yl]amino]-2-methyl-1-propanol, 2-[[7-[(2-Hydroxy-1,1-dimethylethyl)amino]-5-[(phenylmethyl)thio]thiazolo[4,5-d]pyrimidin-2-yl]amino]-1,3-propanediol, and their pharmaceutically acceptable salts and solvates.

30. A compound according to claim 1 being selected from:

2-[[2-[[2-(Ethylthio)ethyl]amino]-5-[(phenylmethyl)thio]thiazolo[4,5-d]pyrimidin-7-yl]amino]-2-methyl-1-propanol, (2S)-2-[[7-[(2-Hydroxy-1,1-dimethylethyl)amino]-5-[(phenylmethyl)thio]thiazolo[4,5-d]pyrimidin-2-yl]amino]-3,3-dimethyl-1-butanol, ($\alpha$S)-$\alpha$-[(1R)-1-[[7-[(2-Hydroxy-1,1-dimethylethyl)amino]-5-[(phenylmethyl)thio]thiazolo[4,5-d]pyrimidin-2-yl]amino]-2-methoxyethyl]benzenemethanol, 2-[[2-(Ethylamino)-5-[(phenylmethyl)thio]thiazolo[4,5-d]pyrimidin-7-yl]amino]-2-methyl-1-propanol, 2-[[2-[[[3-Fluoro-5-(trifluoromethyl)phenyl]methyl]amino]-5-[(phenylmethyl)thio]thiazolo[4,5-d]pyrimidin-7-yl]amino]-2-methyl-1-propanol, ($\pm$)-2-Methyl-2-[[2-[(1-methylpropyl)amino]-5-[(phenylmethyl)thio]thiazolo[4,5-d]pyrimidin-7-yl]amino]-1-propanol, 2-[[2-[[(4-Methoxyphenyl)methyl]amino]-5-[(phenylmethyl)thio]thiazolo[4,5-d]pyrimidin-7-yl]amino]-2-methyl-1-propanol, 2-[[2-[(2-Hydroxyethyl)amino]-5-[(phenylmethyl)thio]thiazolo[4,5-d]pyrimidin-7-yl]amino]-2-methyl-1-propanol, 2-[[2-[[2-(1H-imidazol-4-yl)ethyl]amino]-5-[(phenylmethyl)thio]thiazolo[4,5-d]pyrimidin-7-yl]amino]-2-methyl-1-propanol, 2-[[2-[(Diphenylmethyl)amino]-5-[(phenylmethyl)thio]thiazolo[4,5-d]pyrimidin-7-yl]amino]-2-methyl-1-propanol, (2S)-2-[[7-[(2-Hydroxy-1,1-dimethylethyl)amino]-5-[(phenylmethyl)thio]thiazolo[4,5-d]pyrimidin-2-yl]amino]-1-butanol, and their pharmaceutically acceptable salts and solvates.

31. A compound according to claim 1 being selected from:

2-[[2-[(2,2-Diethoxyethyl)amino]-5-[(phenylmethyl)thio]thiazolo[4,5-d]pyrimidin-7-yl]amino]-2-methyl-1-propanol, 4-[[7-[(2-Hydroxy-1,1-dimethylethyl)amino]-5-[(phenylmethyl)thio]thiazolo[4,5-d]pyrimidin-2-yl]amino]-1-butanol, (1S,2S)-2-[[7-[(2-Hydroxy-1,1-dimethylethyl)amino]-5-[(phenylmethyl)thio]thiazolo[4,5-d]pyrimidin-2-yl]amino]-cyclohexanol, ($\pm$)-2-[[2-[(2-Hydroxy-1-methylethyl)amino]-5-[(phenylmethyl)thio]thiazolo[4,5-d]pyrimidin-7-yl]amino]-2-methyl-1-propanol, 2-[[2-[[2-(2-Hydroxyethoxy)ethyl]amino]-5-[(phenylmethyl)thio]thiazolo[4,5-d]pyrimidin-7-yl]amino]-2-methyl-1-propanol, ($\pm$)-2-[[7-[(2-Hydroxy-1,1-dimethylethyl)amino]-5-[(phenylmethyl)thio]thiazolo[4,5-d]pyrimidin-2-yl]amino]-1-pentanol, 2-[[7-[(2-Hydroxy-1,1-dimethylethyl)amino]-5-[(phenylmethyl)thio]thiazolo[4,5-d]pyrimidin-2-yl]amino]-acetamide, (±)-2-[[2-[[1-(4-Fluorophenyl)ethyl]amino]-5-[(phenylmethyl)thio]thiazolo[4,5-d]pyrimidin-7-yl]amino]-2-methyl-propanol, (1R,2S)-2-[[7-[(2-Hydroxy-1,1-dimethylethyl)amino]-5-[(phenylmethyl)thio]thiazolo[4,5-d]pyrimidin-2-yl]amino]-cyclohexanol, (αS)-α-[(1R)-1-[[7-[(2-Hydroxy-1,1-dimethylethyl)amino]-5-[(phenylmethyl)thio]thiazolo[4,5-d]pyrimidin-2-yl]amino]ethyl]-benzenemethanol, (±)-2-[[2-(Methylamino)-5-[(phenylmethyl)thio]thiazolo[4,5-d]pyrimidin-7-yl]amino]-1-propanol, and their pharmaceutically acceptable salts and solvates.

32. A compound according to claim 1 being selected from:

(2R)-4-Methyl-2-[[2-(methylamino)-5-[(phenylmethyl)thio]thiazolo[4,5-d]pyrimidin-7-yl]amino]-1-pentanol, N-[2-(Methylamino)-5-[(phenylmethyl)thio]thiazolo[4,5-d]pyrimidin-7-yl]-L-serine, ethyl ester, (±)-2-[[5-[(Phenylmethyl)thio]-2-[[(tetrahydro-2-furanyl)methyl]amino]thiazolo[4,5-d]pyrimidin-7-yl]amino]-1-butanol, (±)-2-[[5-[(Phenylmethyl)thio]-2-[[(tetrahydro-2-furanyl)methyl]amino]thiazolo[4,5-d]pyrimidin-7-yl]amino]-1-propanol, (2R)-4-Methyl-2-[[5-[(phenylmethyl)thio]-2-[[(tetrahydro-2-furanyl)methyl]amino]thiazolo[4,5-d]pyrimidin-7-yl]amino]-1-pentanol, N-[5-[(Phenylmethyl)thio]-2-[[(tetrahydro-2-furanyl)methyl]amino]thiazolo[4,5-d]pyrimidin-7-yl]-L-serine, ethyl ester, (±)-2-[[2-[[2-(2-Hydroxyethoxy)ethyl]amino]-5-[(phenylmethyl)thio]thiazolo[4,5-d]pyrimidin-7-yl]amino]-1-propanol, (±)-4-[2-[[7-[[1-(Hydroxymethyl)propyl]amino]-5-[(phenylmethyl)thio]thiazolo[4,5-d]pyrimidin-2-yl]amino]ethyl]-benzenesulfonamide, (±)-4-[2-[[7-[(2-Hydroxy-1-methylethyl)amino]-5-[(phenylmethyl)thio]thiazolo[4,5-d]pyrimidin-2-yl]amino]ethyl]-benzenesulfonamide, 4-[2-[[7-[[(1R)-1-(Hydroxymethyl)-3-methylbutyl]amino]-5-[(phenylmethyl)thio]thiazolo[4,5-d]pyrimidin-2-yl]amino]ethyl]-benzenesulfonamide, (±)-4-[2-[[7-[(2-Hydroxypropyl)amino]-5-[(phenylmethyl)thio]thiazolo[4,5-d]pyrimidin-2-yl]amino]ethyl]-benzenesulfonamide, $N^7$-Ethyl-$N^2$-[2-(1H-imidazol-4-yl)ethyl]-5-[(phenylmethyl)thiothiazolo[4,5-d]pyrimidine-2,7-diamine, and their pharmaceutically acceptable salts and solvates.

33. A compound according to claim 1 being selected from:

$N^2$-[2-(1H-imidazol-4-yl)ethyl]-5-[(phenylmethyl)thio]-$N^7$-(3-pyridinylmethyl)-thiazolo[4,5-d]pyrimidine-2,7-diamine, (±)-2-[[2-[[2-(1H-imidazol-4-yl)ethyl]amino]-5-[(phenylmethyl)thio]thiazolo[4,5-d]pyrimidin-7-yl]amino]-1-butanol, (±)-2-[[2-[[2-(1H-imidazol-4-yl)ethyl]amino]-5-[(phenylmethyl)thio]thiazolo[4,5-d]pyrimidin-7-yl]amino]-1-propanol, (2R)-2-[[2-[[2-(1H-imidazol-4-yl)ethyl]amino]-5-[(phenylmethyl)thio]thiazolo[4,5-d]pyrimidin-7-yl]amino]-4-methyl-1-pentanol, (±)-1-[[2-[[2-(1H-imidazol-4-yl)ethyl]amino]-5-[(phenylmethyl)thio]thiazolo[4,5-d]pyrimidin-7-yl]amino]-2-propanol, 5-[[2-[[2-(1H-imidazol-4-yl)ethyl]amino]-5-[(phenylmethyl)thio]thiazolo[4,5-d]pyrimidin-7-yl]amino]-1-pentanol, 1-[2-[[2-(1H-imidazol-4-yl)ethyl]amino]-5-[(phenylmethyl)thio]thiazolo[4,5-d]pyrimidin-7-yl]-4-(phenylmethyl)-4-piperidinol, (±)-1-[2-[[2-(1H-imidazol-4-yl)ethyl]amino]-5-[(phenylmethyl)thio]thiazolo[4,5-d]pyrimidin-7-yl]-3-piperidinecarboxamide, 2-[Ethyl[2-[(2-(1H-imidazol-4-yl)ethyl]amino]-5-[(phenylmethyl)thio]thiazolo[4,5-d]pyrimidin-7-yl]amino]-1-ethanol, $N^2$-[2-(1H-imidazol-4-yl)ethyl]-$N^7$,$N^7$-dimethyl-5-[(phenylmethyl)thio]-thiazolo[4,5-d]pyrimidine-2,7-diamine, $N^7$-[2-(Diethylamino)ethyl]-$N^7$-ethyl-$N^2$-[2-(1H-imidazol-4-yl)ethyl]-5-[(phenylmethyl)thio]thiazolo[4,5-d]pyrimidine-2,7-diamine, and their pharmaceutically acceptable salts and solvates.

34. A compound according to claim 1 being selected from:

$N^2$-(2-Phenoxyethyl)-5-[(phenylmethyl)thio]-$N^7$-(3-pyridinylmethyl)-thiazolo[4,5-d]pyrimidine-2,7-diamine, $N^2$-(2-Phenoxyethyl)-$N^7$-[1-(phenylmethyl)-4-piperidinyl]-5-[(phenylmethyl)thio]thiazolo[4,5-d]pyrimidine-2,7-diamine, 2-Methyl-2-[[2-[(2-phenoxyethyl)amino]-5-[(phenylmethyl)thio]thiazolo[4,5-d]pyrimidin-7-yl]amino]-1-propanol, (±)-2-[[2-[(2-Phenoxyethyl)amino]-5-[(phenylmethyl)thio]thiazolo[4,5-d]pyrimidin-7-yl]amino]-1-propanol, (±)-4-Methyl-2-[[2-[(2-phenoxyethyl)amino]-5-[(phenylmethyl)thio]thiazolo[4,5-d]pyrimidin-7-yl]amino]-1-pentanol, 1-[2-[(2-Phenoxyethyl)amino]-5-[(phenylmethyl)thio]thiazolo[4,5-d]pyrimidin-7-yl]-4-(phenylmethyl)-4-piperidinol, 2-[[2-(Cyclopropylamino)-5-[(phenylmethyl)thio]thiazolo[4,5-d]pyrimidin-7-yl]amino]-1-butanol, 2-[[2-(Cyclopropylamino)-5-[(phenylmethyl)thio]thiazolo[4,5-d]pyrimidin-7-yl]amino]-1-propanol, (2R)-2-[[2-(Cyclopropylamino)-5-[(phenylmethyl)thio]thiazolo[4,5-d]pyrimidin-7-yl]amino]-4-methyl-1-pentanol, N-[2-(Cyclopropylamino)-5-[(phenylmethyl)thio]thiazolo[4,5-d]pyrimidin-7-yl]-L-serine, ethyl ester, (2R)-2-[[2-[[1-(Hydroxymethyl)butyl]amino]-5-[(phenylmethyl)thio]thiazolo[4,5-d]pyrimidin-7-yl]amino]-4-methyl-1-pentanol, N-[2-[[1-(Hydroxymethyl)butyl]amino]-5-[(phenylmethyl)thio]thiazolo[4,5-d]pyrimidin-7-yl]-L-serine, ethyl ester, and their pharmaceutically acceptable salts and solvates.

35. A compound according to claim 1 being selected from:

(±)-2-[[7-[Cyclohexyl(2-hydroxyethyl)amino]-5-[(phenylmethyl)thio]thiazolo[4,5-d]pyrimidin-2-yl]amino]-1-pentanol, 2-[2-[[7-(Ethylamino)-5-[(phenylmethyl)thio]thiazolo[4,5-d]pyrimidin-2-yl]amino]ethoxy-1-ethanol, 2-(2-[[7-[(1-Methylethyl)amino]-5-[(phenylmethyl)thio]thiazolo[4,5-d]pyrimidin-2-yl]amino]ethoxy]-1-ethanol, (±)-2-[[2-[[2-(2-Hydroxyethoxy)ethyl]amino]-5-[(phenylmethyl)thio]thiazolo[4,5-d]pyrimidin-7-yl]amino]-1-butanol, 2-[[2-[[2-(2-Hydroxyethoxy)ethyl]amino]-5-[(phenylmethyl)thio]thiazolo[4,5-d]pyrimidin-7-yl]amino]-2-methyl-1-propanol, (2R)-2-[[2-[[2-(2-Hydroxyethoxy)ethyl]amino]-5-[(phenylmethyl)thio]thiazolo[4,5-d]pyrimidin-7-yl]amino]-4-methyl-1-pentanol, 2-[Cyclohexyl-[2-[[2-(2-hydroxyethoxy)ethyl]amino]-5-[(phenylmethyl)thio]thiazolo[4,5-d]pyrimidin-7-yl]amino]-1-ethanol, (±)-2-[[5-[(Phenylmethyl)thio]-2-(4-piperidinylamino)thiazolo[4,5-d]pyrimidin-7-yl]amino]-1-propanol, (±)-N-[2-[[7-[[1-(Hydroxymethyl)propyl]amino]-5-[(phenylmethyl)thio]thiazolo[4,5-d]pyrimidin-2-yl]amino]ethyl]-acetamide, (±)-N-[2-[[7-[(2-Hydroxy-1-methylethyl)amino]-5-[(phenylmethyl)thio]thiazolo[4,5-d]pyrimidin-2-yl]amino]ethyl]-acetamide, N-[2-[[7-[(2-Hydroxyethyl)amino]-5-[(phenylmethyl)thio]thiazolo[4,5-d]pyrimidin-2-yl]amino]ethyl]-acetamide, and their pharmaceutically acceptable salts and solvates.

36. A compound according to claim 1 being selected from:

N[2-[[7-[[(1R)-1-(Hydroxymethyl)-3-methylbutyl]amino]-5-[(phenylmethyl)thio]thiazolo[4,5-d]pyrimidin-2-yl]amino]ethyl]-acetamide, $N^7$-(2-Methoxyethyl)-5-[(phenylmethyl)thio]-$N^2$-[2-(2-thienyl)ethyl]thiazolo[4,5-d]pyrimidine-2,7-diamine, $N^7$-(2-Ethoxyethyl)-5-[(phenylmethyl)thio]-$N^2$-[2-(2-thienyl)ethyl]thiazolo[4,5-d]pyrimidine-2,7-diamine, $N^7$-(2,2-Dimethylpropyl)-5-[(phenylmethyl)thio]-$N^2$-[2-(2-thienyl)ethyl]thiazolo[4,5-d]pyrimidine-2,7-diamine, (2R)-4-Methyl-2-[[5-[(phenylmethyl)thio]-2-[[2-(2-thienyl)ethyl]amino]thiazolo[4,5-d]pyrimidin-7-yl]amino]-1-pentanol, (±)-1-[[5-[(Phenylmethyl)thio]-2-[[2-(2-thienyl)ethyl]amino]thiazolo[4,5-d]pyrimidin-7-yl]amino]-2-propanol, (±)-2-[[5-[(Phenylmethyl)thio]-2-[[2-(2-thienyl)ethyl]amino]thiazolo[4,5-d]pyrimidin-7-yl]amino]-1-butanol, (±)-2-[[5-[(Phenylmethyl)thio]-2-[[2-(2-thienyl)ethyl]amino]thiazolo[4,5-d]pyrimidin-7-yl]amino]-1-propanol, (2R)-2-[[2-[(2-Hydroxyethyl)amino]-5-[(phenylmethyl)thio]thiazolo[4,5-d]pyrimidin-7-yl]amino]-4-methyl-1-pentanol, (±)-N,N-Diethyl-1-[2-[[2-[(2-hydroxyethyl)amino]-5-[(phenylmethyl)thio]thiazolo[4,5-d]pyrimidin-7-yl]-3-piperidinecarboxamide, (2R)-2-[[2-[(3-Hydroxypropyl)amino]-5-[(phenylmethyl)thio]thiazolo[4,5-d]pyrimidin-7-yl]amino]-4-methyl-1-pentanol, (±)-2-[[2-[(3-Hydroxypropyl)amino]-5-[(phenylmethyl)thio]thiazolo[4,5-d]pyrimidin-7-yl]amino]-1-butanol, and their pharmaceutically acceptable salts and solvates.

37. A compound according to claim 1 being selected from:

(±)-2-[[2-[(3-Hydroxypropyl)amino]-5-[(phenylmethyl)thio]thiazolo[4,5-d]pyrimidin-7-yl]amino]-1-propanol, 2-[[7-[(2-Hydroxy-1-methylethyl)amino]-5-[(phenylmethyl)thio]thiazolo[4,5-d]pyrimidin-2-yl]amino-acetamide, 4-[1-[7-[(4-Methylcyclohexyl)amino]-5-[(phenylmethyl)thio]thiazolo[4,5-d]pyrimidin-2-yl]-3-azetidinyl]-1-piperazinesulfonamide, 3-[[2-[[2-(4-Morpholinyl)ethyl]amino]-5-[(phenylmethyl)thio]thiazolo[4,5-d]pyrimidin-7-yl]amino]-1-propanol, 2-Methyl-2-[[2-[[2-(4-morpholinyl)ethyl]amino]-5-[(phenylmethyl)thio]thiazolo[4,5-d]pyrimidin-7-yl]amino]-1-propanol, (±)-2-[[2-[[2-(4-Morpholinyl)ethyl]amino]-5-[(phenylmethyl)thio]thiazolo[4,5-d]pyrimidin-7-yl]amino]-1-propanol, (2R)-4-Methyl-2-[[2-[[2-(4-morpholinyl)ethyl]amino]-5-[(phenylmethyl)thio]thiazolo[4,5-d]pyrimidin-7-yl]amino]-1-pentanol, 2-[[2-(3,4-Dihydroxyphenyl)ethyl]amino]-5-[(phenylmethyl)thio]-thiazolo[4,5-d]pyrimidin-7(4H)-one, (±)-2-[(2-Hydroxy-1-methylethyl)amino]-5-[(phenylmethy)thio]-thiazolo[4,5-d]pyrimidin-7(4H)-one, and their pharmaceutically acceptable salts and solvates.

* * * * *